United States Patent
Kastelein et al.

(10) Patent No.: US 12,297,281 B2
(45) Date of Patent: *May 13, 2025

(54) IL10RA BINDING MOLECULES AND METHODS OF USE

(71) Applicant: Synthekine, Inc., Menlo Park, CA (US)

(72) Inventors: Robert Kastelein, Menlo Park, CA (US); Deepti Rokkam, Menlo Park, CA (US); Patrick J. Lupardus, Menlo Park, CA (US); Sandro Vivona, Menlo Park, CA (US)

(73) Assignee: Synthekine, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/006,831

(22) PCT Filed: Aug. 5, 2021

(86) PCT No.: PCT/US2021/044603
§ 371 (c)(1),
(2) Date: Jan. 25, 2023

(87) PCT Pub. No.: WO2022/031885
PCT Pub. Date: Feb. 10, 2022

(65) Prior Publication Data
US 2023/0272091 A1    Aug. 31, 2023

Related U.S. Application Data

(60) Provisional application No. 63/135,884, filed on Jan. 11, 2021, provisional application No. 63/136,098, filed on Jan. 11, 2021, provisional application No. 63/078,745, filed on Sep. 15, 2020, provisional application No. 63/061,562, filed on Aug. 5, 2020.

(51) Int. Cl.
C07K 16/28        (2006.01)
A61K 45/06        (2006.01)
C12N 15/63        (2006.01)

(52) U.S. Cl.
CPC .......... C07K 16/2866 (2013.01); A61K 45/06 (2013.01); C12N 15/63 (2013.01); *C07K 2317/22* (2013.01); *C07K 2317/24* (2013.01); *C07K 2317/31* (2013.01); *C07K 2317/565* (2013.01); *C07K 2317/569* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,553,932 B1 * | 6/2009 | Von Herrath | C07K 16/2866 424/85.1 |
| 8,258,268 B2 | 9/2012 | Wu et al. | |
| 8,420,784 B2 * | 4/2013 | Kato | A61P 31/10 424/139.1 |
| 8,921,528 B2 | 12/2014 | Holt et al. | |
| 8,975,382 B2 | 3/2015 | Revets et al. | |
| 10,556,954 B2 | 2/2020 | Ting et al. | |
| 10,927,186 B2 | 2/2021 | Roobrouck et al. | |
| 2006/0024295 A1 | 2/2006 | Brunetta | |
| 2010/0297127 A1 | 11/2010 | Ghilardi et al. | |
| 2011/0028695 A1 | 2/2011 | Revets et al. | |
| 2011/0053865 A1 | 3/2011 | Saunders et al. | |
| 2011/0142831 A1 | 6/2011 | Cua et al. | |
| 2012/0201746 A1 | 8/2012 | Liu et al. | |
| 2012/0316324 A1 | 12/2012 | Adams et al. | |
| 2014/0065142 A1 | 3/2014 | Roschke et al. | |
| 2014/0154256 A1 | 6/2014 | Wu et al. | |
| 2014/0302038 A1 | 10/2014 | Dimasi et al. | |
| 2014/0363426 A1 | 12/2014 | Moore et al. | |
| 2015/0079088 A1 | 3/2015 | Lowman et al. | |
| 2016/0046730 A1 | 2/2016 | Ghayur et al. | |
| 2016/0251440 A1 | 9/2016 | Roobrouck et al. | |
| 2017/0106051 A1 | 4/2017 | Oh et al. | |
| 2017/0298149 A1 | 10/2017 | Baeuerle et al. | |
| 2018/0362655 A1 | 12/2018 | Wang et al. | |
| 2019/0315864 A1 | 10/2019 | Xu et al. | |
| 2019/0382500 A1 | 12/2019 | Abujoub et al. | |
| 2020/0071716 A1 | 3/2020 | Raab et al. | |
| 2020/0087624 A1 | 3/2020 | Wood et al. | |
| 2020/0148772 A1 | 5/2020 | Ting et al. | |
| 2020/0157237 A1 | 5/2020 | Regev et al. | |

(Continued)

FOREIGN PATENT DOCUMENTS

| | | |
|---|---|---|
| CN | 111018985 A | 6/2019 |
| WO | 2008/011081 A2 | 1/2008 |
| WO | 2009/068631 A1 | 6/2009 |

(Continued)

OTHER PUBLICATIONS

Crepaldi et al. Up-regulation of IL-10R1 expression is required to render human neutrophils fully responsive to IL-10. The Journal of Immunology. Aug. 15, 2001;167(4):2312-22.

Delgoffe et al., "Interpreting mixed signals: the cell's cytokine conundrum," Current Opinion in Immunology, vol. 23(5), pp. 632-638, Retrieved from the internet, URL: https://www.ncbi.nlm.nih.gov/pmc/articles/PMC3190023/pdf/nihms315192.pdf, (Oct. 2011).

Donnelly et al.. The expanded family of class II cytokines that share the IL-10 receptor-2 (IL-10R2) chain. Journal of leukocyte biology. Aug. 2004;76(2):314-21.

(Continued)

*Primary Examiner* — Marianne P Allen
(74) *Attorney, Agent, or Firm* — Kilpatrick Townsend & Stockton LLP

(57) ABSTRACT

The present disclosure relates to biologically active molecules comprising a single domain antibody (sdAb) that specifically binds to the extracellular domain of human IL10Ra, compositions comprising such antibodies, and methods of use thereof.

16 Claims, No Drawings
Specification includes a Sequence Listing.

(56) References Cited

U.S. PATENT DOCUMENTS

| | | | |
|---|---|---|---|
| 2023/0272091 A1 | 8/2023 | Kastelein et al. | |
| 2023/0322936 A1 | 10/2023 | Kastelein et al. | |

FOREIGN PATENT DOCUMENTS

| | | | |
|---|---|---|---|
| WO | 2010/142551 A2 | 12/2010 | |
| WO | 2013/006544 A1 | 1/2013 | |
| WO | 2013/059299 A1 | 4/2013 | |
| WO | 2015/142675 A2 | 9/2015 | |
| WO | 2016/097313 A1 | 6/2016 | |
| WO | 2017/198212 A1 | 11/2017 | |
| WO | 2018/233624 A1 | 12/2018 | |
| WO | 2019/129221 A1 | 7/2019 | |
| WO | 2020/144164 A1 | 7/2020 | |
| WO | 2020/187711 A1 | 9/2020 | |
| WO | 2022031885 A2 | 2/2022 | |
| WO | 2022032022 A2 | 2/2022 | |
| WO | 2022150788 A2 | 7/2022 | |

OTHER PUBLICATIONS

Fu et al. Comparison of Camelus Bactrianus VHH Sequences From Conventional and Heavy Chain Antibodies. Genbank Entry (online) National Center for Biotechnology Information, Sep. 21, 2013. Retrieved from the Internet www.ncbi.nlm.nih.gov/nucleotide/KF179376.1, 1 page.

Jiang et al. Regulation of interleukin-10 receptor ubiquitination and stability by beta-TrCP-containing ubiquitin E3 ligase. PloS one. Nov. 8, 2011;6(11):e27464.

Lundin, et al. "Production and partial characterization of mouse monoclonal antibodies recognizing common cytokine receptor gamma chain (γc) of human, mouse and primate origin Note." Apmis 109, No. 10 (2001): 647-655.

Pingwara et al. IFN-λ Modulates the Migratory Capacity of Canine Mammary Tumor Cells via Regulation of the Expression of Matrix Metalloproteinases and Their Inhibitors. Cells. Apr. 23, 2021;10(5):999.

Jiang et al., "Regulation of Interleukin-10 Receptor Ubiquitination and Stability by Beta-TrCP-Containing Ubiquitin E3 Ligase", PLoS One, vol. 6, No. 11, Nov. 2011, 14 pages.

Application No. PCT/US2021/044603, International Search Report and Written Opinion, Mailed On Feb. 2, 2022, 12 pages.

U.S. Appl. No. 18/260,688, filed Jan. 11, 2022, Kastelein, et al.

Application No. PCT/US2021/044603, International Preliminary Report on Patentability, Mailed On Feb. 16, 2023, 9 pages.

Application No. PCT/US2021/044834, International Preliminary Report on Patentability, Mailed On Feb. 16, 2023, 11 pages.

Application No. PCT/US2021/044834, International Search Report and Written Opinion, Mailed On Feb. 2, 2022, 15 pages.

Application No. PCT/US2021/044858, International Preliminary Report on Patentability, Mailed On Feb. 16, 2023, 7 pages.

Application No. PCT/US2021/044858, International Search Report and Written Opinion, Mailed On Dec. 20, 2021, 10 pages.

Application No. PCT/US2022/012049, International Preliminary Report on Patentability, Mailed On Jul. 20, 2023, 10 pages.

Application No. PCT/US2022/012049, International Search Report and Written Opinion, Mailed On Jun. 21, 2022, 14 pages.

PCT Application No. PCT/US2024/033162, International Search Report and Written Opinion, mailed on Jan. 23, 2025, 14 pages.

* cited by examiner

IL10RA BINDING MOLECULES AND METHODS OF USE

CROSS-REFERENCES TO RELATED APPLICATIONS

This application is a national stage application under 35 U.S.C. § 371 of International Patent Application No. PCT/US2021/044603, filed Aug. 5, 2021, which claims priority to U.S. Provisional Application No. 63/061,562, filed Aug. 5, 2020, U.S. Provisional Application No. 63/078,745, filed Sep. 15, 2020, U.S. Provisional Application No. 63/135,884, filed Jan. 11, 2021, and U.S. Provisional Application No. 63/136,098, filed Jan. 11, 2021, the disclosures of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Sep. 15, 2021, is named 106249-1258368-004800PC_SL.txt and is 61,440 bytes in size.

FIELD OF THE INVENTION

The present disclosure relates to biologically active molecules comprising a single domain antibody that specifically binds to the extracellular domain of the IL10Ra, compositions comprising such single domain antibodies, and methods of use thereof.

BACKGROUND

The anti-inflammatory cytokine interleukin-10 (IL-10), also known as human cytokine synthesis inhibitory factor (CSIF), is classified as a type(class)-2 cytokine, a set of cytokines that includes IL-19, IL-20, IL-22, IL-24 (Mda-7), and IL-26, interferons (IFN-$\alpha$, -$\beta$, -$\gamma$, -$\delta$, -$\epsilon$, $\kappa$, -$\Omega$, and –$\tau$) and interferon-like molecules (limitin, IL-28A, IL-28B, and IL-29). Human IL-10 is a homodimer with a molecular mass of 37 kDa, wherein each 18.5 kDa monomer comprises 178 amino acids, the first 18 of which comprise a signal peptide, and two cysteine residues that form two intramolecular disulfide bonds.

The human IL-10 receptor (hIL10R), a type II cytokine receptor, comprises alpha (hIL10Ra) and beta (IL10Rb) subunits, which are also referred to as hIL10R1 and hIL10R2, respectively. The hIL10Ra receptor subunit is expressed as a 578 amino acid pre-protein, the first 21 amino acids comprising a signal sequence which is post-translationally cleaved in the mature 557 amino acid protein. Amino acids 22-235 (amino acids 1-214 of the mature protein) correspond to the extracellular domain, amino acids 236-256 (amino acids 215-235 of the mature protein) correspond to the transmembrane domain and amino acids 257-578 (amino acids 236-557 of the mature protein) correspond to the intracellular domain. hIL10Ra is referenced at UniProtKB database as entry Q13651.

Activation of the IL10 receptor requires binding of the ligand to both the alpha and beta IL10R subunits. One homodimer of an IL-10 polypeptide binds to IL10Ra and the other homodimer of the same IL-10 polypeptide binds to IL10Rb.

IL-10 exhibits pleiotropic effects in immunoregulation and inflammation through actions on T cells, B cells, macrophages, and antigen presenting cells (APC). IL-10 is produced by mast cells, counteracting the inflammatory effect that these cells have at the site of an allergic reaction. Although IL-10 is predominantly expressed in macrophages, expression has also been detected in activated T cells, B cells, mast cells, and monocytes. IL-10 can suppress immune responses by inhibiting expression of IL-1$\alpha$, IL-1$\beta$, IL-6, IL8, TNF$\alpha$, GM-CSF and G-CSF in activated monocytes and activated macrophages, and it also suppresses IFN-$\gamma$ production by NK cells. IL10 can block NF-$\kappa$B activity and is involved in the regulation of the JAK-STAT signaling pathway.

Although monoclonal antibodies are the most widely used reagents for the detection and quantification of proteins, monoclonal antibodies are large molecules of about 150 kDa and it sometimes limits their use in assays with several reagents competing for close epitopes recognition. A unique class of immunoglobulin containing a heavy chain domain and lacking a light chain domain (commonly referred to as heavy chain" antibodies (HCAbs) is present in camelids, including dromedary camels, Bactrian camels, wild Bactrian camels, llamas, alpacas, vicuñas, and guanacos as well as cartilaginous fishes such as sharks. The isolated variable domain region of HCAbs is known as a VHH (an abbreviation for "variable-heavy-heavy" reflecting their architecture) or Nanobody® (Ablynx). Single domain VHH antibodies possesses the advantage of small size (~12-14 kD), approximately one-tenth the molecular weight a conventional mammalian IgG class antibody) which facilitates the binding of these VHH molecules to antigenic determinants of the target which may be inaccessible to a conventional monoclonal IgG format (Ingram et al., 2018). Furthermore, VHH single domain antibodies are frequently characterized by high thermal stability facilitating pharmaceutical distribution to geographic areas where maintenance of the cold chain is difficult or impossible. These properties, particularly in combination with simple phage display discovery methods that do not require heavy/light chain pairing (as is the case with IgG antibodies) and simple manufacture (e.g., in bacterial expression systems) make VHH single domain antibodies useful in a variety of applications including the development of imaging and therapeutic agents.

SUMMARY OF THE INVENTION

The present disclosure provides molecules that specifically bind to the extracellular domain of IL10Ra.

The present disclosure provides a IL10Ra binding molecule that specifically binds to the extracellular domain of IL10Ra (e.g., human IL10Ra).

In some embodiments, the IL10Ra binding molecule comprises a single domain antibody (sdAb) that specifically binds to the extracellular domain of the human IL10Ra.

In some embodiments, the IL10Ra binding molecule is a sdAb, the sdAb comprising a set of CDRs corresponding to CDR1, CDR2, and CDR3 as shown in a row of Table 1 below.

In some embodiments, the IL10Ra binding molecule comprises a CDR1, a CDR2, and a CDR3 as described in a row of Table 1 below, in which the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 1 below.

In some embodiments, the IL10Ra binding molecule consists of, optionally consists essentially of, or optionally comprises a single domain antibody (sdAb) having at least 80%, alternatively at least 85%, alternatively at least 90%, alternatively at least 95%, alternatively at least 98%, alternatively at least 99% identity (or being identical except for 1, 2, 3, or 4 amino acids, optionally conservative amino acid substitutions) or 100% identity to a polypeptide sequence of any one of SEQ ID NOS: SEQ ID NOS:1, 5, 9, 13, 17, 21, 25, 29, 33, 37, 41, 45, 49, 53, 57, 61, 65, 69, as shown in Table 1 below.

TABLE 1 hIL10Ra VHHs and CDRs

Table 1. hIL10Ra VHHs and CDRs

| | VHH Sequence | CDR1 | CDR2 | CDR3 |
|---|---|---|---|---|
| hIL10Ra_VHH1 | QVQLQESGGGSIQAGGSLRLSCAASRYLYSIDYMAWFRQSPGKEREPVAVIYTASGATFYPDSVKGRFTISQDNAKMTVYLQMNSLKSEDTAMYYCAAVRKTDSYLFDAQSFTYWGQGTQVTVSS (SEQ ID NO: 1) | YLYSIDYMA (SEQ ID NO: 2) | VIYTASGATFYPDSVKG (SEQ ID NO: 3) | VRKTDSYLFDAQSFTY (SEQ ID NO: 4) |
| hIL10Ra_VHH2 | QVQLQESGGGSVQAGGSLRLSCVASRYLYSTNYMAWFRQSPGKEREAVAVIYTASGATLYTDSVKGRFTISQDNAKMTVYLQMNRLKSEDTAMYYCAAVRKTDSYLFDAQSFTYWGQGTQVTVSS (SEQ ID NO: 5) | YLYSTNYMA (SEQ ID NO: 6) | VIYTASGATLYTDSVKG (SEQ ID NO: 7) | VRKTDSYLFDAQSFTY (SEQ ID NO: 8) |
| hIL10Ra_VHH3 | QVQLQESGGGSIQAGGSLRLSCVASRYLYSTNYMAWFRQSPGKEREAVAVIYTASGATLYTDSVKGRFTISQDNAKMTVYLQMNRLKSEDTAMYYCAAVRKTDSYLFDAQSFTYWGQGTQVTVSS (SEQ ID NO: 9) | YLYSTNYMA (SEQ ID NO: 10) | VIYTASGATLYTDSVKG (SEQ ID NO: 11) | VRKTDSYLFDAQSFTY (SEQ ID NO: 12) |
| hIL10Ra_VHH4 | QVQLQESGGGSIQAGGSLRLSCAASRYLYSIDYMAWFRQSPGKEREPAAVIYTASGATFYPDSVKGRFTISQDNAKMTVYLQMNSLKSEDTAMYYCAAVRKTDSYLFDAQSFTYWGQGTQVTVSS (SEQ ID NO: 13) | YLYSIDYMA (SEQ ID NO: 14) | VIYTASGATFYPDSVKG (SEQ ID NO: 15) | VRKTDSYLFDAQSFTY (SEQ ID NO: 16) |
| hIL10Ra_VHH5 | QVQLQESGGGSIQAGGSLRLSCVASKYLYSTNYMAWFRQSPGKEREAVAAIYTASGATLYSDSNKGRFTISQDNAKMTVYLQMNSLKSEDTAMYYCAAVRKTGSYLFDAQSFTYWGQGTQVTVSS (SEQ ID NO: 17) | YLYSTNYMA (SEQ ID NO: 18) | AIYTASGATLYSDSNKG (SEQ ID NO: 19) | VRKTGSYLFDAQSFTY (SEQ ID NO: 20) |
| hIL10Ra_VHH6 | QVQLQESGGGSVQAGGSLRLSCAASRFTYSSYCMGWFRQAPGKEREGVASIDSDGSTSYTDSVKGRFTISKDNAKNTLYLQMNSLKPEDTAMYYCALDLMSTVVPGFCGFLLSAGMDYWGKGTQVTVSS (SEQ ID NO: 21) | FTYSSYCMG (SEQ ID NO: 22) | SIDSDGSTSYTDSVKG (SEQ ID NO: 23) | DLMSTVVPGFCGFLLSAGMDY (SEQ ID NO: 24) |
| hIL10Ra_VHH7 | QVQLQESGGGSVQAGGSLRLSCAVSGYTFNSNCMGWFRQAPGKEREGVATIYTGVGSTYYADSVKGR | YTFNSNCMG (SEQ ID NO: 26) | TIYTGVGSTYYADSVKG (SEQ ID NO: 27) | EPLSRVYGGSCPTPTFGY (SEQ ID NO: 28) |

TABLE 1-continued hIL10Ra VHHs and CDRs

Table 1. hIL10Ra VHHs and CDRs

| | VHH Sequence | CDR1 | CDR2 | CDR3 |
|---|---|---|---|---|
| | FTISQDNAKNTVYL QMNSLKPEDTAMY YCAAEPLSRVYGGS CPTPTFGYWGQGT QVTVSS (SEQ ID NO: 25) | | | |
| hIL10Ra_VHH8 | QVQLQESGGGSVQ AGGSLRLSCAASGY TYSMYCMGWFRQ APGKEREGVAQINS DGSTSYADSVKGRF TISKDNAKNTLYLQ MNSLKPEDTAMYY CAADSRVYGGSWY ERLCGPYTYEYNY WGQGTQVTVSS (SEQ ID NO: 29) | YTYSMYC MG (SEQ ID NO: 30) | QINSDGSTSY ADSVKG (SEQ ID NO: 31) | DSRVYGGSW YERLCGPYTY EYNY (SEQ ID NO: 32) |
| hIL10Ra_VHH9 | QVQLQESGGGSVQ AGGSLRLSCAVSGY AYSTYCMGWFRQA PGKEREGVAAIDSG GSTSYADSVKGRFT ISKDNAKNTLYLR MNSLKPEDTAMYY CAAVPPPPDGGSCL FLGPEIKVSKADFR YWGQGTQVTVSS (SEQ ID NO: 33) | YAYSTYC MG (SEQ ID NO: 34) | AIDSGGSTSY ADSVKG (SEQ ID NO: 35) | VPPPPDGGSC LFLGPEIKVSK ADFRY (SEQ ID NO: 36) |
| hIL10Ra_VHH10 | QVQLQESGGGSVQ AGGSLRLSCAASRY LYSIDYMAWFRQSP GKEREPVAVIYTAS GATFYPDSVKGRFT ISQDNAKMTVYLQ MNSLKSEDTAMYY CAAVRKTDSYLFD AQSFTYWGQGTQV TVSS (SEQ ID NO: 37) | YLYSIDYM A (SEQ ID NO: 38) | VIYTASGATF YPDSVKG (SEQ ID NO: 39) | VRKTDSYLFD AQSFTY (SEQ ID NO: 40) |
| hIL10Ra_VHH11 | QVQLQESGGGSVQ AGGSLRLSCGASRY TYSSYCMGWFRQA PGKEREGVAVIDSD GSTSYADSVKGRFT ISKDNGKNTLYLQ MNSLKPEDTAMYY CAADLGHYRPPCG VLYLGMDYWGKG TQVTVSS (SEQ ID NO: 41) | YTYSSYCM G (SEQ ID NO: 42) | VIDSDGSTSY ADSVKG (SEQ ID NO: 43) | DLGHYRPPCG VLYLGMDY (SEQ ID NO: 44) |
| hIL10Ra_VHH12 | QVQLQESGGGSVQ AGGSLRLSCTVSGY TYSSNCMGWFRQA PGKEREGVATIYTG GGNTYYADSVKGR FTISQDNAKNTVYL QMNNLKPEDTAMY YCAAEPLSRVYGGS CPTPTFDYWGQGT QVTVSS (SEQ ID NO: 45) | YTYSSNCM G (SEQ ID NO: 46) | TIYTGGGNTY YADSVKG (SEQ ID NO: 47) | EPLSRVYGGS CPTPTFDY (SEQ ID NO: 48) |
| hIL10Ra_VHH13 | QVQLQESGGGSVQ AGGSLRLSCAVSGY SYSSNCMGWFRQA PGKEREGVATIHTG GGSTYYADSVKGR FTISQDNAKNTVYL QMNSLKPEDTAMY YCAAEPLSRLYGGS | YSYSSNCM G (SEQ ID NO: 50) | TIHTGGGSTY YADSVKG (SEQ ID NO: 51) | EPLSRLYGGS CPTPTFGY (SEQ ID NO: 52) |

TABLE 1-continued hIL10Ra VHHs and CDRs

| Table 1. hIL10Ra VHHs and CDRs | VHH Sequence | CDR1 | CDR2 | CDR3 |
|---|---|---|---|---|
| | CPTPTFGYWGQGT QVTVSS (SEQ ID NO: 49) | | | |
| hIL10Ra_VHH14 | QVQLQESGGGSVQ AGGSLRLSCGASGY TYSSYCMGWFRQV PGKEREGVAVIDSD GSTSYADSVKGRFT ISKDNGKNTLYLQ MNSLKPEDTAMYY CAADLGHYRPPCG VLYLGMDYWGKG TQVTVSS (SEQ ID NO: 53) | YTYSSYCM G (SEQ ID NO: 54) | VIDSDGSTSY ADSVKG (SEQ ID NO: 55) | DLGHYRPPCG VLYLGMDY (SEQ ID NO: 56) |
| hIL10Ra_VHH15 | QVQLQESGGGSVQ AGGSLRLSCGASGY TYSGYCMGWFRQA PGKEREGVAVIDSD GSTSYADSVKGRFT ISKDNGKNTLYLQ MNSLKPEDTAMYY CAADLGHYRPPCG VLYLGMDYWGKG TQVTVSS (SEQ ID NO: 57) | YTYSGYC MG (SEQ ID NO: 58) | VIDSDGSTSY ADSVKG (SEQ ID NO: 59) | DLGHYRPPCG VLYLGMDY (SEQ ID NO: 60) |
| hIL10Ra_VHH16 | QVQLQESGGGSVQ AGGSLRLACAASR YTYSNYCMGWFRQ APGKEREGVATIDS DGNTSYADSVKGR FTISRDNAKNTLYL QMNSLKPGDTAMY YCAADLGHYRPPC GAYYYGMDYWGK GTQVTVSS (SEQ ID NO: 61) | YTYSNYC MG (SEQ ID NO: 62) | TIDSDGNTSY ADSVKG (SEQ ID NO: 63) | DLGHYRPPCG AYYYGMDY (SEQ ID NO: 64) |
| hIL10Ra_VHH17 | QVQLQESGGGSVQ AGGSLRLCAASGY SNCSYDMTWYRQA PGKEREFVSAIHSD GSTRYADSVKGRFF ISQDNAKNTVYLQ MNSLKPEDTAMYY CKTDPLHCRAHGG SWYSVRANYWGQ GTQVTVSS (SEQ ID NO: 65) | YSNCSYDM T (SEQ ID NO: 66) | AIHSDGSTRY ADSVKG (SEQ ID NO: 67) | DPLHCRAHG GSWYSVRAN Y (SEQ ID NO: 68) |
| hIL10Ra_VHH18 | QVQLQESGGGSVQ AGGSLRLSCAVSGY TYNSNCMGWFRQA PGKEREGVATIYTG V GSTYYADSVKGRF TISQDNAKNTVYLQ MNSLKPEDTAMYY CAAEPLSRVYGGSC PTPTFGYWGQGTQ VTVSS (SEQ ID NO: 69) | YTYNSNC MG (SEQ ID NO: 70) | TIYTGVGSTY YADSVKG (SEQ ID NO: 71) | EPLSRVYGGS CPTPTFGY (SEQ ID NO: 72) |

In some embodiments, the foregoing sets of CDRs are incorporated in a humanized VHH framework to provide "humanized" sdAb IL10Ra binding molecules.

The disclosure further provides methods of chemical or recombinant processes for the preparation of the IL10Ra binding molecules of the present disclosure.

The disclosure further provides nucleic acids encoding the IL10Ra binding molecules. Table 2 provides examples of DNA sequences encoding IL10Ra binding molecules as described herein.

TABLE 2 hIL10Ra VHH DNA Sequences

| Name | Sequence |
|---|---|
| hIL10Ra_VHH1 | CAGGTTCAGCTTCAGGAGTCCGGTGGAGGCTCCATCCAG GCCGGGGGCTCTCTCCGCCTGTCTTGCGCCGCTTCCAGAT ACCTCTACAGTATCGACTACATGGCTTGGTTTCGTCAGAG CCCAGGAAAAGAGCGGGAACCCGTGGCAGTAATCTACAC TGCCTCAGGTGCCACATTTTACCCCGACTCTGTCAAGGGC AGGTTCACCATCTCTCAGGATAATGCCAAGATGACAGTG TACTTGCAGATGAACTCCCTGAAATCTGAGGATACCGCTA TGTATTACTGTGCGCAGTGCGCAAGACCGATTCTTACCT GTTCGACGCTCAGAGTTTTACCTACTGGGGCCAGGGCACT CAGGTCACCGTCAGCAGC (SEQ ID NO: 73) |
| hIL10Ra_VHH2 | CAGGTGCAGTTGCAGGAGTCCGGCGGGGGTTCCGTGCAA GCAGGCGGATCTCTGCGCCTGTCCTGCGTGGCCTCTCGTT ATTTGTATAGCACCAACTACATGGCTTGGTTCCGTCAGTC CCCAGGCAAAGAGCGCGAAGCCGTAGCCGTAATCTATAC GGCCTCTGGGGCAACACTCTATACCGACTCAGTGAAGGG ACGCTTCACGATTTCCCAAGACAATGCAAAGATGACCGT GTACTTGCAGATGAACCGCCTGAAGAGCGAGGACACGGC TATGTATTACTGCGCAGCCGTGCGCAAGACCGACTCCTAC TTGTTTGACGCTCAGTCCTTCACTTATTGGGGCAGGGTA CACAGGTCACCGTGAGCAGT (SEQ ID NO: 74) |
| hIL10Ra_VHH3 | CAAGTACAGCTCCAGGAGAGCGGCGGTGGATCTATCCAA GCAGGGGTAGCCTTAGGTTGTCCTGTGTGGCGTCCAGAT ACCTGTATAGCACGAACTACATGGCATGGTTCAGACAGT CCCCAGGCAAGGAACGCGAGGCAGTCGCCGTTATTTACA CTGCATCTGGGGCCACCCTCTATACGGACAGCGTGAAGG GAAGGTTTACAATCTCCCAGGACAACGCGAAGATGACCG TGTACCTTCAGATGAACCGCCTGAAGTCCGAGGACACCG CCATGTATTACTGTGCAGCGGTGCGCAAGACCGACAGCT ATCTGTTCGACGCGCAGTCATTCACTTATTGGGGCCAAGG AACCCAAGTGACCGTCAGCTCA (SEQ ID NO: 75) |
| hIL10Ra_VHH4 | CAGGTGCAGCTCCAAGAGTCCGGGGGAGGCTCTATCCAG GCGGGAGGCAGTCTGCGCTTGTCCTGCGCCGCAAGTCGTT ATCTGTACTCCATTGATTACATGGCATGGTTCCGCCAGTC CCCAGGTAAGGAACGTGAACCTGCCGCTGTGATCTACAC CGCTTCTGGAGCAACCTTTTATCCTGATAGCGTTAAGGGT CGCTTCACCATCTCTCAGGATAACGCCAAAATGACAGTGT ACCTCCAGATGAACAGCCTGAAGTCTGAGGACACTGCCA TGTACTATTGTGCGGCTGTGCGCAAGACCGACTCCTATCT GTTTGATGCACAGAGCTTTACCTATTGGGGTCAGGGCACC CAGGTGACTGTGTCTAGC (SEQ ID NO: 76) |
| hIL10Ra_VHH5 | CAGGTCCAGTTGCAGGAGTCCGTGGAGGTTCCATCCAG GCGGGTGGGTCCCTTCGTCTCTTCCTGCGTGGCCTCTAAGT ACCTGTATTCAACCAACTACATGGCATGGTTCAGACAGTC TCCCGGCAAAGAGCGTGAGGCAGTGGCCGCGATCTATAC AGCTTCTGGGGCACCCTGTACTCTGATTCCAATAAGGGA AGGTTCACTATCTCACAGGATAACGCCAAAATGACCGTC TACCTTCAGATGAACAGCCTCAAGTCTGAAGACACGGCA ATGTATTACTGTGCAGCCGTGCGCAAAACTGGGAGCTAC CTGTTTGACGCTCAGTCTTTCACTTATTGGGGCCAGGGTA CGCAGGTGACAGTCTCTTCT (SEQ ID NO: 77) |
| hIL10Ra_VHH6 | CAGGTGCAACTCCAGGAGAGCGGAGGCGGTTCTGTTCAG GCAGGAGGTTCCCTGAGACTGTCCTGTGCCGCGTCTCGCT TTACGTATTCATCCTACTGCATGGGATGGTTCAGACAAGC GCCGGGGAAAGAAAGGGAAGGCGTGGCCTCCATTGACTC CGACGGCTCAACTTCATACACTGATAGCGTGAAAGGCCG GTTCACCATCTCTAAGGACAACGCGAAGAACACCCTGTA TCTCCAGATGAACAGCCTCAAGCCTGAGGATACTGCCAT GTACTATTGCGCACTCGACCTGATGTCTACTGTGGTCCCA GGCTTCTGCGGGTTCCTGCTCTCTGCTGGCATGGACTACT GGGGGAAGGGCACTCAGGTAACGGTTAGCTCC (SEQ ID NO: 78) |
| hIL10Ra_VHH7 | CAGGTGCAGCTTCAGGAATCTGGCGGGGGCTCCGTGCAG GCCGGGGGCTCCCTCAGACTTTCCTGTGCCGTCTCCGGTT ACACATTTAACAGTAACTGTATGGGCTGGTTCCGCCAGGC ACCAGGCAAGGAGAGGGAAGGTGTGGCCACAATCTATAC TGGTGTTGGGAGTACGTACTATGCTGATTCCGTGAAAGGT CGCTTCACAATTTCCCAGGACAACGCGAAGAACACTGTG TACTTGCAGATGAATAGCCTGAAGCCTGAAGATACCGCA ATGTATTACTGCGCTGCCGAGCCACTCTCCCGCGTATATG GTGGAAGTTGCCCCACCCCCACTTTCGGTTACTGGGGCCA GGGCACTCAAGTGACCGTGTCCTCT (SEQ ID NO: 79) |
| hIL10Ra_VHH8 | CAGGTTCAGCTTCAGGAGTCTGGGGGCGGTTCAGTGCAG GCTGGCGGTTCTCTCCGCCTGTCCTGCGCTGCCAGCGGCT ATACTTACAGCATGTACTGCATGGGCTGGTTCCGGCAAGC CCCCGGCAAAGAGCGTGAAGGCGTCGCTCAAATCAACAG CGACGGGTCAACCAGCTACGCCGATTCTGTCAAGGGCAG ATTTACTATCAGCAAGGACAACGCCAAAAACACACTGTA CCTCCAGATGAACTCTTTGAAGCCTGAGGACACCGCGAT GTATTACTGCGCCGCTGACAGCCGCGTGTACGGTGGCAG CTGGTATGAGAGGCTGTGCGGCCCGTACACCTACGAGTA CAACTATTGGGACAGGGCACGCAGGTGACAGTTAGCTC C (SEQ ID NO: 80) |
| hIL10Ra_VHH9 | CAGGTGCAACTGCAAGAGAGTGGCGGAGGCTCCGTCCAG GCTGGAGGTTCCCTGCGGCTGTCTTGCGCCGTCAGCGGCT ACGCATATTCCACTTACTGTATGGGTTGGTTCCGCCAGGC CCCTGGAAAGGAACGCGAGGGTGTTGCCGCTATTGATAG CGGAGGCTCCACATCCTATGCGGACTCCGTGAAAGGTCG TTTCACCATCTCCAAGGATAACGCCAAGAACACTCTGTAC CTGCGCATGAACTCTCTGAAGCCTGAGGACACTGCCATGT ATTACTGCGCCGTGTGCCCCCTCCACCCGACGGGGCCTC TTGTCTGTTTCTTGGCCCGGAGATCAAGGTGTCCAAGGCT GATTTCCGTTATTGGGGCCAGGGAACTCAAGTCACCGTGT CTTCC (SEQ ID NO: 81) |
| hIL10Ra_VHH10 | CAGGTCCAGCTCCAGGAGTCCGGTGGAGGCTCCGTTCAG GCCGGTGGCAGCTTGCGTCTGAGCTGCGCGGCTTCAAGA TACCTGTACTCCATTGATTACATGGCATGGTTCCGTCAGT CTCCTGGCAAGGAGCGCGAGCCCGTCGTCTGTGATCTATA CCGCCAGCGGAGCCACGTTCTACCCTGATTCCGTCAAGG GCCGCTTCACCATTAGCCAAGACAACGCTAAGATGACGG TGTACCTCCAAATGAATAGCCTGAAAAGCGAGGACACAG CGATGTATTACTGCGCCGCGTGTTAGGAAAACTGATAGTTA CCTGTTCGATGCACAGTCTTTCACTTACTGGGGCAGGGC ACCCAAGTTACCGTCTCCTCT (SEQ ID NO: 82) |
| hIL10Ra_VHH11 | CAGGTGCAGCTCCAGGAATCTGGAGGGGGCAGTGTGCAG GCCGGGGGCTCCCTGCGCTTGAGCTGTGGAGCCAGCCGC TACACGTATTCCAGTTACTGTATGGGCTGGTTCAGACAAG CTCCGGGTAAGGAGAGAGGGAGTGCCGTAATTGATT CTGACGGGTCCACTAGCTATGGGATTCAGTCAAGGGCC GGTTCACCATCAGCAAGGACAATGGTAAGAACACACTGT ACCTGCAAATGAACAGCCTGAAGCCCGAGGACACCGCCA TGTACTATTGTGCCGCTGATCTCGGACATTACCGCCCTCC CTGCCGGTGTGCTCTATCTCGGGATGGACTATTGGGGTAAG GGCACCCAGGTGACCGTGTCCTCT (SEQ ID NO: 83) |
| hIL10Ra_VHH12 | CAGGTGCAGCTCCAGGAAAGCGGCGGGGGTAGCGTTCAA GCAGGTGGGTCCCTGCGCTTGAGCTGTACTGTGTCCGGCT ACACCTACTCAAGCAACTGCATGGGATGGTTCCGTCAGG CCCCTGGCAAGGAACGCGAAGGCGTGGCTACTATCTACA CCGGCGGTGGCAACACTTATTACGCCGACTCCGTTAAGG |

TABLE 2-continued hIL10Ra VHH DNA Sequences

| Name | Sequence |
|---|---|
| | GGCGTTTCACTATCAGCCAAGACAACGCCAAGAACACCG<br>TGTATCTGCAAATGAATAACCTGAAGCCTGAAGCACCG<br>CCATGTATTACTGTGCTGCCGAGCCCCTTTCCCGCGTTTA<br>CGGCGGTTCTTGTCCTACCCCTACCTTTGACTACTGGGGT<br>CAGGGAACACAGGTGACAGTGTCCAGT<br>(SEQ ID NO: 84) |
| hIL10Ra_VHH13 | CAAGTCCAACTCCAGGAATCTGGGGGAGGCTCCGTACAG<br>GCTGGCGGTTCCCTTCGTCTGTCCTGTGCTGTGTCAGGGT<br>ACTCCTACTCCAGTAACTGTATGGGCTGGTTCCGGCAAGC<br>CCCCGGAAAGGAGCGCGAGGGCGTGGCTACCATCCACAC<br>AGGGGGCGGTTCCACATATTACGCCGATAGTGTCAAGGG<br>CCGCTTCACCATTAGTCAGGACAACGCCAAGAATACCGT<br>TTACCTTCAAATGAACTCTTTGAAACCTGAGGACACTGCG<br>ATGTATTACTGTGCGGCAGAGCCTTTGTCCCGCCTGTACG<br>GGGGATCTTGTCCGACCCCGACTTTCGGGTACTGGGGAC<br>AGGGCACCCAGGTGACAGTGTCCTCC<br>(SEQ ID NO: 85) |
| hIL10Ra_VHH14 | CAGGTGCAGTTGCAGGAAAGCGGGGGTGGCAGCGTCCAA<br>GCCGGTGGCAGCCTGCGTCTGTCCTGCGGTGCCTCCGGCT<br>ATACTTACTCCAGCTATTGCATGGGTTGGTTCCGCCAAGT<br>GCCAGGAAAGGAGCGTGAGGGGGTGGCTGTAATTGATTC<br>AGATGGGTCAACAAGCTACGCTGACAGCGTTAAAGGTCG<br>CTTCACCATCAGTAAGGACAACGGCAAGAACACCCTCTA<br>CCTGCAAATGAACTCCCTGAAGCCGGAGGATACCGCAAT<br>GTATTACTGTGCCGCTGACTTGGGACACTACCGCCCTCCG<br>TGCGGTGTGCTTTATCTGGGCATGGATTACTGGGGTAAGG<br>GAACCCAAGTGACGGTGTCTTCT<br>(SEQ ID NO: 86) |
| hIL10Ra_VHH15 | CAGGTACAACTCCAGGAGTCTGGCGGTGGGTCCGTGCAG<br>GCAGGTGGCAGCCTTCGCCTCTCCTGCGGGGCCTCCGGGT<br>ACACCTATAGTGGCTACTGCATGGGGTGGTTCAGGCAAG<br>CCCCCGGTAAGGAACGTGAGGGAGTTGCTGTGATTGATT<br>CAGATGGGTCCACGAGTTACGCTGACTCCGTGAAAGGTA<br>GGTTCACAATCTCCAAAGATAATGGCAAGAACACCCTCT<br>ACCTTCAGATGAATAGCCTGAAGCCAGAAGACACCGCCA<br>TGTATTACTGTGCTGCCGACCTGGGACACTATCGCCCTCC<br>GTGCGGGTCCTGTACTTGGGCATGGACTATTGGGGCAA<br>GGGGACCCAGGTGACTGTGTCCTCT<br>(SEQ ID NO: 87) |
| hIL10Ra_VHH16 | CAGGTGCAGTTGCAGGAATCCGGTGGAGGCTCTGTTCAG<br>GCCGGGGCTCTCTCCGCCTGGCCTGCGCAGCCTCCAGGT<br>ATACTTACAGCAACTACTGCATGGGGTGGTTTCGCCAGGC<br>TCCGGGCAAAGAGCGTGAGGGAGTGGCTACTATTGATTC<br>CGATGGAAACACCAGCTACGCCGATAGCGTGAAGGGCAG<br>ATTTACTATCAGCAGAGATAACGCTAAAAACACGTTGTA<br>CCTCCAGATGAACTCACTCAAGCCGGGGGACACAGCTAT<br>GTATTACTGCGCAGCCGATCTGGGTCACTACCGCCCGCCC<br>TGCGGCGCATATTACTATGCGATGGACTACTGGGGCAAG<br>GGCACCCAGGTGACCGTGTCCAGT<br>(SEQ ID NO: 88) |
| hIL10Ra_VHH17 | CAGGTGCAGCTCCAAGAGTCTGGCGGGGGTTCCGTGCAA<br>GCCGGTGGCTCACTCAGGTTGAGTTGCGCAGCCAGCGGC<br>TATAGCAACTGTTCCTATGACATGACTTGGTATCGCCAGG<br>CCCCTGCAAAGAGCGTGAGTTCGTGTCAGCTATTCACTC<br>CGACGGCTCCACTCGTTATGCGGACTCTGTGAAGGGCCG<br>GTTTTTCATCTCCCAGGACAACGCTAAAAACACTGTCTAT<br>TTGCAGATGAACTCTCTGAAACCCGAAGATACCGCCATG<br>TACTATTGCAAAACCGATCCTCTGCATTGTCGCGCCCACG<br>GCGGGAGTTGGTACTCTGTGCGGGCCAACTATTGGGCC<br>AGGGCACCCAGGTCACCGTGTCCTCA<br>(SEQ ID NO: 89) |
| hIL10Ra_VHH18 | CAGGTACAACTCCAGGAGTCTGGCGGTGGCAGCGTGCAG<br>GCAGGCGGAAGCCTGAGGCTGTCCTGCGCTGTATCTGGC<br>TACACTTATAATTCCAACTGCATGGGTTGGTTTCGGCAGG<br>CTCCAGGTAAGGAGCGCGAGGGCGTCGCCACCATTTATA<br>CAGGTGTTGGCAGCACATATTACGCCGACAGCGTGAAGG<br>GAAGGTTCACCATCTCCCAAGACAATGCGAAAAACACAG<br>TGTATCTCCAGATGAATAGCCTGAAGCCCGAGGACACGG<br>CTATGTATTACTGCGCTGCCGAGCCACTGAGCAGAGTGTA |

| Name | Sequence |
|---|---|
| | TGGGGGCAGCTGTCCTACACCCACTTTCGGCTATTGGGGT<br>CAAGGCACCCAGGTTACAGTCAGCTCC<br>(SEQ ID NO: 90) |

The disclosure further provides recombinant viral and non-viral vectors comprising a nucleic acid encoding the IL10Ra binding molecules of the present disclosure or the CDRs of the IL10Ra binding molecules of the present disclosure.

The disclosure further provides host cells comprising recombinant viral and non-viral vectors comprising a nucleic acid the IL10Ra binding molecules of the present disclosure or the CDRs of the IL10Ra binding molecules of the present disclosure.

The disclosure further provides host cells comprising recombinant viral and non-viral vectors comprising a nucleic acid the IL10Ra binding molecules of the present disclosure or the CDRs of the IL10Ra binding molecules of the present disclosure.

The compositions of the present disclosure are useful in multiple therapeutic and/or prophylactic applications. The IL10Ra receptor subunit is the proprietary receptor subunit of the IL10Ra/IL10Rb tetrameric IL-10 receptor. In addition to forming a subunit of the IL10 receptor, the IL10Rb subunit is shared with the IL22, IL26, IL28 and IL29 receptors. Consequently, compositions of the present disclosure which selectively binding to the IL-10Ra receptor subunit leads to selective inhibition of IL10 function without substantial interference with IL22, IL26, IL28 and IL29 function.

In some embodiments, the compositions of the present disclosure are useful as inhibitors of the IL10 receptor, in particular via targeting of the IL10Ra subunit, and down-regulate the immunosuppressive effects of endogenous IL-10. The therapeutic and/or prophylactic activity of IL10R antagonists (e.g., IL10Ra binding molecules) are well established in the scientific literature.

In some embodiments, the compositions of the present invention are useful in the treatment of infectious disease, in some embodiments for the prophylaxis of chronic or acute infections. For example, Von Herrath et al (U.S. Pat. No. 7,553,932) disclose the use of IL10 receptor antagonist antibodies for the treatment of chronic acute infections, in particular chronic or acute viral infections. Kato, et al. (U.S. Pat. No. 8,420,784) describe IL10Ra antibodies are useful in the treatment and prophylaxis of pathogenic infections. Brooks, et al (J. Exp. Med. (2008) 205(3)3:533-541; Nature Medicine (2001) 12(11):1301-1309) describe that IL10 receptor antagonists are useful in T-cell recovery and prevention of viral persistence and that blocking the IL-10 activity enhances clearance of persistent viral infections.

In some embodiments, the compositions of the present invention are useful in the treatment of neoplastic disease. Inhibition of IL-10 function has been established to mitigate the immunosuppressive effects of IL-10 and may be useful in the treatment of cancer, in some embodiments, in combination with cancer immunotherapy, such as the administration of tumor vaccines (Ni, et al (2015) Cellular Immunology 293(2):126-129. Beguelin, et al (2015) Leukemia 29:1684-1694 disclose IL-10Ra is markedly elevated in diffuse large B-cell lymphomas and that inhibitors of IL10Ra function interfere with the IL-10/IL10R auto stimulatory loop and are useful in the treatment of diffuse large B cell lymphoma.

The disclosure further kits comprising the IL10Ra binding molecules of the present disclosure.

The disclosure further provides pharmaceutical formulations comprising the recombinant viral and non-viral vectors comprising a nucleic acid the IL10Ra binding molecules of the present disclosure and methods of use thereof in the treatment or prevention of diseases, disorders or conditions in a mammalian subject.

In another aspect, the present disclosure provides constructs for the targeted delivery of therapeutic agents to a cell expressing the IL10Ra receptor, wherein the IL10Ra binding molecule is conjugated to one or more therapeutic agents, optionally through a chemical or polypeptide linker. The disclosure further provides methods of use of the foregoing in the treatment of disease associated with expression of the IL10Ra in a subject, the method comprising the administration of a therapeutically effective amount of the IL10Ra binding molecule conjugated to the therapeutic agent to a subject in need to treatment, alone or in combination with one or more additional therapeutic agents.

In some embodiments, the diseases amenable to treatment are diseases, disorders or conditions associated with signaling from receptor comprising the IL10Ra. In some embodiments, the IL10Ra binding molecules of the present disclosure are useful in the treatment of diseases associated with dysregulated T cell or B cell activity. In some embodiments, the IL10Ra binding molecules of the present disclosure are useful in the treatment of autoimmune disease associated with aberrant cell activity arising from dysregulated signaling in cells expressing the IL10Ra. In some embodiments, the IL10Ra binding molecules of the present disclosure are useful in the treatment of neoplastic diseases associated with aberrant cell activity arising from dysregulated signaling in cells expressing the IL10Ra.

In another aspect, the present disclosure provides constructs for the identification of cells expressing the IL10Ra receptor wherein the IL10Ra binding molecule is conjugated to one or more imaging agents, optionally through a chemical or polypeptide linker. The disclosure further provides methods of use of the foregoing in the identification of cells expressing the IL10Ra receptor in a subject, the method comprising the administration of a effective amount of the IL10Ra binding molecule conjugated to the imaging agent to a subject in need to treatment and evaluating the subject for the presence of the imaging agent that is conjugated to the IL10Ra binding molecule.

In another aspect, the present disclosure provides IL10Ra binding molecules which have are modified for extended duration of action in vivo wherein the IL10Ra binding molecule is conjugated to one or more carrier molecules. Such IL10Ra molecules are useful in the therapeutic applications discussed above.

The present disclosure provides IL10Ra binding molecules comprising a polypeptide sequence that specifically binds to the extracellular domain of the IL10Ra and methods of use thereof in the isolation, depletion or enrichment of cells expressing the IL10Ra in a biological sample.

In some embodiments, the IL10Ra binding molecules of the present disclosure are competitive inhibitors of IL10. In some embodiments, the IL10Ra binding molecules of the present disclosure are useful in inhibiting the activity of IL10 or IL10 muteins.

DETAILED DESCRIPTION OF THE INVENTION

Introduction

In order for the present disclosure to be more readily understood, certain terms and phrases are defined below as well as throughout the specification. The definitions provided herein are non-limiting and should be read in view of the knowledge of one of skill in the art would know.

Before the present methods and compositions are described, it is to be understood that this disclosure is not limited to particular method or composition described, as such may, of course, vary.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited.

It should be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It will be appreciated that throughout this disclosure reference is made to amino acids according to the single letter or three letter codes. For the reader's convenience, the single and three letter amino acid codes are provided in below:

TABLE 3

Amino Acid Abbreviations

| Single Letter Abbreviation | Name | 3-letter abbreviation |
|---|---|---|
| G | Glycine | Gly |
| P | Proline | Pro |
| A | Alanine | Ala |
| V | Valine | Val |
| L | Leucine | Leu |
| I | Isoleucine | Ile |
| M | Methionine | Met |
| C | Cysteine | Cys |
| F | Phenylalanine | Phe |
| Y | Tyrosine | Tyr |
| W | Tryptophan | Trp |
| H | Histidine | His |
| K | Lysine | Lys |
| R | Arginine | Arg |
| Q | Glutamine | Gln |
| N | Asparagine | Asn |
| E | Glutamic Acid | Glu |
| D | Aspartic Acid | Asp |
| S | Serine | Ser |
| T | Threonine | Thr |

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)). The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Definitions

Unless otherwise indicated, the following terms are intended to have the meaning set forth below. Other terms are defined elsewhere throughout the specification.

Activate: As used herein the term "activate" is used in reference to a receptor or receptor complex to reflect a biological effect, directly and/or by participation in a multicomponent signaling cascade, arising from the binding of an agonist ligand to a receptor responsive to the binding of the ligand.

Activity: As used herein, the term "activity" is used with respect to a molecule to describe a property of the molecule with respect to a test system (e.g., an assay) or biological or chemical property (e.g., the degree of binding of the molecule to another molecule) or of a physical property of a material or cell (e.g., modification of cell membrane potential). Examples of such biological functions include but are not limited to catalytic activity of a biological agent, the ability to stimulate intracellular signaling, gene expression, cell proliferation, the ability to modulate immunological activity such as inflammatory response. "Activity" is typically expressed as a level of a biological activity per unit of agent tested such as [catalytic activity]/[mg protein], [immunological activity]/[mg protein], international units (IU) of activity, [STAT5 phosphorylation]/[mg protein], [proliferation]/[mg protein], plaque forming units (pfu), etc. As used herein, the term proliferative activity refers to an activity that promotes cell proliferation and replication, including dysregulated cell division such as that observed in neoplastic diseases, inflammatory diseases, fibrosis, dysplasia, cell transformation, metastasis, and angiogenesis.

Administer/Administration: The terms "administration" and "administer" are used interchangeably herein to refer the act of contacting a subject, including contacting a cell, tissue, organ, or biological fluid of the subject in vitro, in vivo or ex vivo with an agent (e.g., an a IL10Ra binding molecule or an engineered cell expressing an IL10Ra binding molecule, a chemotherapeutic agent, an antibody, or a pharmaceutical formulation comprising one or more of the foregoing). Administration of an agent may be achieved through any of a variety of art recognized methods including but not limited to the topical administration, intravascular injection (including intravenous or intraarterial infusion), intradermal injection, subcutaneous injection, intramuscular injection, intraperitoneal injection, intracranial injection, intratumoral injection, transdermal, transmucosal, iontophoretic delivery, intralymphatic injection, intragastric infusion, intraprostatic injection, intravesical infusion (e.g., bladder), inhalation (e.g respiratory inhalers including dry-powder inhalers), intraocular injection, intraabdominal injection, intralesional injection, intraovarian injection, intracerebral infusion or injection, intracerebroventricular injection (ICVI), and the like. The term "administration" includes contact of an agent to the cell, tissue or organ as well as the contact of an agent to a fluid, where the fluid is in contact with the cell, tissue or organ.

Affinity: As used herein the term "affinity" refers to the degree of specific binding of a first molecule (e.g., a ligand) to a second molecule (e.g., a receptor) and is measured by the equilibrium dissociation constant $K_D$, a ratio of the dissociation rate constant between the molecule and the its target ($k_{off}$) and the association rate constant between the molecule and its target ($k_{on}$).

Agonist: As used herein, the term "agonist" refers a first agent that specifically binds a second agent ("target") and interacts with the target to cause or promote an increase in the activation of the target. In some instances, agonists are activators of receptor proteins that modulate cell activation, enhance activation, sensitize cells to activation by a second agent, or up-regulate the expression of one or more genes, proteins, ligands, receptors, biological pathways, that may result in cell proliferation or pathways that result in cell cycle arrest or cell death such as by apoptosis. In some embodiments, an agonist is an agent that binds to a receptor and alters the receptor state resulting in a biological response that mimics the effect of the endogenous ligand of the receptor. The term "agonist" includes partial agonists, full agonists and superagonists. An agonist may be described as a "full agonist" when such agonist which leads to a substantially full biological response (i.e. the response associated with the naturally occurring ligand/receptor binding interaction) induced by receptor under study, or a partial agonist. A "superagonist" is a type of agonist that can produce a maximal response greater than the endogenous agonist for the target receptor, and thus has an activity of more than 100% of the native ligand. A super agonist is typically a synthetic molecule that exhibits greater than 110%, alternatively greater than 120%, alternatively greater than 130%, alternatively greater than 140%, alternatively greater than 150%, alternatively greater than 160%, or alternatively greater than 170% of the response in an evaluable quantitative or qualitative parameter of the naturally occurring form of the molecule when evaluated at similar concentrations in a comparable assay. It should be noted that the biological effects associated with the full agonist may differ in degree and/or in kind from those biological effects of partial or superagonists. In contrast to agonists, antagonists may specifically bind to a receptor but do not result the signal cascade typically initiated by the receptor and may to modify the actions of an agonist at that receptor. Inverse agonists are agents that produce a pharmacological response that is opposite in direction to that of an agonist.

Antagonist: As used herein, the term "antagonist" or "inhibitor" refers a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist. Inhibitors are molecules that decrease, block, prevent, delay activation, inactivate, desensitize, or down-regulate, e.g., a gene, protein, ligand, receptor, biological pathway including an immune checkpoint pathway, or cell.

Antibody: As used herein, the term "antibody" refers collectively to: (a) a glycosylated or non-glycosylated immunoglobulin that specifically binds to target molecule, and (b) immunoglobulin derivatives thereof, including but not limited to antibody fragments such as single domain antibodies. In some embodiments the immunoglobulin derivative competes with the immunoglobulin from which it was derived for binding to the target molecule. The term antibody is not restricted to immunoglobulins derived from any particular species and includes murine, human, equine, camelids, antibodies of cartilaginous fishes including, but not limited to, sharks. The term "antibody" encompasses antibodies isolatable from natural sources or from animals following immunization with an antigen and as well as engineered antibodies including monoclonal antibodies, bispecific antibodies, tri-specific, chimeric antibodies, humanized antibodies, human antibodies, CDR-grafted, veneered, or deimmunized (e.g., to remove T-cell epitopes) antibodies, camelized (in the case of VHHs), or molecules comprising binding domains of antibodies (e.g., CDRs) in non-immunoglobulin scaffolds. The term "antibody" should not be construed as limited to any particular means of synthesis and includes naturally occurring antibodies isolatable from natural sources and as well as engineered antibodies molecules that are prepared by "recombinant" means including antibodies isolated from transgenic animals that are transgenic for human immunoglobulin genes or a hybridoma prepared therefrom, antibodies isolated from a host cell transformed with a nucleic acid construct that results in expression of an antibody, antibodies isolated from a combinatorial antibody library including phage display libraries. In one embodiment, an "antibody" is a mammalian immunoglobulin of the IgG1, IgG2, IgG3 or IgG4 class. In some embodiments, the antibody is a "full length antibody" comprising variable and constant domains providing binding and effector functions. The term "single domain antibody" (sdAb) as used herein refers an antibody fragment consisting of a monomeric variable antibody domain that is able to bind specifically to an antigen and compete for binding with the parent antibody from which it is derived. The term "single domain antibody" includes scFv and VI-III molecules. As used herein, the term "VHH" refers to a single domain antibody derived from camelid antibody typically obtained from immunization of camelids (including camels, llamas and alpacas (see, e.g., Hamers-Casterman, et al. (1993) Nature 363:446-448). VHHs are also referred to as heavy chain antibodies or Nanobodies® as Single domain antibodies may also be derived from non-mammalian sources such as VHHs obtained from IgNAR antibodies immunization of cartilaginous fishes including, but not limited to, sharks.

Biological Sample: As used herein, the term "biological sample" or "sample" refers to a sample obtained (or derived) from a subject. By way of example, a biological sample comprises a material selected from the group consisting of body fluids, blood, whole blood, plasma, serum, mucus secretions, saliva, cerebrospinal fluid (CSF), bronchoalveolar lavage fluid (BALF), fluids of the eye (e.g., vitreous fluid, aqueous humor), lymph fluid, lymph node tissue, spleen tissue, bone marrow, tumor tissue, including immunoglobulin enriched or cell-type specific enriched fractions derived from one or more of such tissues.

IL10Ra cell: The terms "IL10Ra cell", "IL10Ra-expressing cell", "IL10Ra-positive cell" and "IL10Ra+" cell are used interchangeably herein to refer to a cell which expresses and displays the IL10Ra antigen on the extracellular surface of the cell membrane. Similarly, the terms "IL10Ra-negative cell", "IL10Ra– cells" as are used interchangeably herein to describe cells which do not express or display IL10Ra antigen on the cell surface.

CDR: As used herein, the term "CDR" or "complementarity determining region" is intended to mean the non-contiguous antigen combining sites found within the variable region of both heavy and light chain immunoglobulin polypeptides. CDRs have been described by Kabat et al., *J. Biol. Chem.* 252:6609-6616 (1977); Kabat, et al., U.S. Dept. of Health and Human Services publication entitled "Sequences of proteins of immunological interest" (1991) (also referred to herein as "Kabat 1991" or "Kabat"); by Chothia, et al. (1987) J. Mol. Biol. 196:901-917 (also referred to herein as "Chothia"); and MacCallum, et al. (1996) J. Mol. Biol. 262:732-745, where the definitions include overlapping or subsets of amino acid residues when compared against each other. Nevertheless, application of either definition to refer to a CDR of an antibody or grafted antibodies or variants thereof is intended to be within the scope of the term as defined and used herein. In the context of the present disclosure, unless otherwise specified, the numbering of the CDR positions is provided according to the Kabat numbering convention.

Comparable: As used herein, the term "comparable" is used to describe the degree of difference in two measurements of an evaluable quantitative or qualitative parameter. For example, where a first measurement of an evaluable quantitative parameter and a second measurement of the evaluable parameter do not deviate beyond a range that the skilled artisan would recognize as not producing a statistically significant difference in effect between the two results in the circumstances, the two measurements would be considered "comparable." In some instances, measurements may be considered "comparable" if one measurement deviates from another by less than 35%, alternatively by less than 30%, alternatively by less than 25%, alternatively by less than 20%, alternatively by less than 15%, alternatively by less than 10%, alternatively by less than 7%, alternatively by less than 5%, alternatively by less than 4%, alternatively by less than 3%, alternatively by less than 2%, or by less than 1%. In particular embodiments, one measurement is comparable to a reference standard if it deviates by less than 15%, alternatively by less than 10%, or alternatively by less than 5% from the reference standard.

Conservative Amino Acid Substitution: As used herein, the term "conservative amino acid substitution" refers to an amino acid replacement that changes a given amino acid to a different amino acid with similar biochemical properties (e.g., charge, hydrophobicity, and size). For example, the amino acids in each of the following groups can be considered as conservative amino acids of each other: (1) hydrophobic amino acids: alanine, isoleucine, leucine, tryptophan, phenylalanine, valine, proline, and glycine; (2) polar amino acids: glutamine, asparagine, histidine, serine, threonine, tyrosine, methionine, and cysteine; (3) basic amino acids: lysine and arginine; and (4) acidic amino acids: aspartic acid and glutamic acid.

Derived From: As used herein in the term "derived from", in the context of an amino acid sequence is meant to indicate that the polypeptide or nucleic acid has a sequence that is based on that of a reference polypeptide or nucleic acid and is not meant to be limiting as to the source or method in which the protein or nucleic acid is made. By way of example, the term "derived from" includes homologs or variants of reference amino acid or DNA sequences.

Effective Concentration (EC): As used herein, the terms "effective concentration" or its abbreviation "EC" are used interchangeably to refer to the concentration of an agent in an amount sufficient to effect a change in a given parameter in a test system. The abbreviation "E" refers to the magnitude of a given biological effect observed in a test system when that test system is exposed to a test agent. When the magnitude of the response is expressed as a factor of the concentration ("C") of the test agent, the abbreviation "EC" is used. In the context of biological systems, the term Emax refers to the maximal magnitude of a given biological effect observed in response to a saturating concentration of an activating test agent. When the abbreviation EC is provided with a subscript (e.g., $EC_{40}$, $EC_{50}$, etc.) the subscript refers to the percentage of the Emax of the biological response observed at that concentration. For example, the concentration of a test agent sufficient to result in the induction of a measurable biological parameter in a test system that is 30% of the maximal level of such measurable biological parameter in response to such test agent, this is referred to as the "$EC_{30}$" of the test agent with respect to such biological parameter. Similarly, the term "$EC_{100}$" is used to denote the effective concentration of an agent that results the maximal (100%) response of a measurable parameter in response to such agent. Similarly, the term $EC_{50}$ (which is commonly used in the field of pharmacodynamics) refers to the concentration of an agent sufficient to results in the half-maximal (about 50%) change in the measurable parameter. The term "saturating concentration" refers to the maximum possible quantity of a test agent that can dissolve in a standard volume of a specific solvent (e.g., water) under standard conditions of temperature and pressure. In pharmacodynamics, a saturating concentration of a drug is typically used to denote the concentration sufficient of the drug such that all available receptors are occupied by the drug, and $EC_{50}$ is the drug concentration to give the half-maximal effect.

Enriched: As used herein in the term "enriched" refers to a sample that is non-naturally manipulated so that a species (e.g., a molecule or cell) of interest is present in: (a) a greater concentration (e.g., at least 3-fold greater, alternatively at least 5-fold greater, alternatively at least 10-fold greater, alternatively at least 50-fold greater, alternatively at least 100-fold greater, or alternatively at least 1000-fold greater) than the concentration of the species in the starting sample, such as a biological sample (e.g., a sample in which the molecule naturally occurs or in which it is present after administration); or (b) a concentration greater than the environment in which the molecule was made (e.g., a recombinantly modified bacterial or mammalian cell).

Extracellular Domain: As used herein the term "extracellular domain" or its abbreviation "ECD" refers to the portion of a cell surface protein (e.g., a cell surface receptor) which is external to of the plasma membrane of a cell. The cell surface protein may be transmembrane protein, a cell surface or membrane associated protein.

Identity: The term "identity," as used herein in reference to polypeptide or DNA sequences, refers to the subunit sequence identity between two molecules. When a subunit position in both of the molecules is occupied by the same monomeric subunit (i.e., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as BLAST 2.0 algorithms, which are described in Altschul et al. (1990) *J Mol. Biol.* 215: 403-410 and Altschul, et al. (1977) *Nucleic Acids Res.* 25: 3389-3402. Software for performing BLAST analyses is publicly available through the National Center for Biotechnology Information (NCBI) web site. The algorithm involves first identifying high scoring sequence pairs (HSPs) by identifying short words of length W of the query sequence, which either match or satisfy some positive-valued threshold score "T" when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters "M" (the reward score for a pair of matching residues; always >0) and "N" (the penalty score for mismatching residues; always <0). For amino acid sequences, a scoring matrix is used to calculate the cumulative score. Extension of the word hits in each direction are halted when: (a) the cumulative alignment score falls off by the quantity X from its maximum achieved value; the cumulative score goes to zero or below, due to the accumulation of one or more negative-scoring residue alignments; or (b) the end of either sequence is reached. The BLAST algorithm parameters "W", "T", and "X" determine the sensitivity and speed of the alignment. The BLASTN program (for nucleotide sequences) functions similarly but uses as defaults a word size ("W") of 28, an expectation ("E") of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, (1989) PNAS (USA) 89:10915-10919).

In An Amount Sufficient to Cause a Response: As used herein the phrase "in an amount sufficient to cause a response" is used in reference to the amount of a test agent sufficient to provide a detectable change in the level of an indicator measured before (e.g., a baseline level) and after the application of a test agent to a test system. In some embodiments, the test system is a cell, tissue or organism. In some embodiments, the test system is an in vitro test system such as a fluorescent assay. In some embodiments, the test system is an in vivo system which involves the measurement of a change in the level a parameter of a cell, tissue, or organism reflective of a biological function before and after the application of the test agent to the cell, tissue, or organism. In some embodiments, the indicator is reflective of biological function or state of development of a cell evaluated in an assay in response to the administration of a quantity of the test agent. In some embodiments, the test system involves the measurement of a change in the level an indicator of a cell, tissue, or organism reflective of a biological condition before and after the application of one or more test agents to the cell, tissue, or organism. The term "in an amount sufficient to effect a response" may be sufficient to be a therapeutically effective amount but may also be more or less than a therapeutically effective amount.

Need of Treatment: The term "in need of treatment" as used herein refers to a judgment made by a physician or other caregiver with respect to a subject that the subject requires or will potentially benefit from treatment. This judgment is made based on a variety of factors that are in the realm of the physician's or caregiver's expertise.

In Need of Prevention: As used herein the term "in need of prevention" refers to a judgment made by a physician or other caregiver with respect to a subject that the subject requires or will potentially benefit from preventative care. This judgment is made based upon a variety of factors that are in the realm of a physician's or caregiver's expertise.

Inhibitor: As used herein the term "inhibitor" refers to a molecule that decreases, blocks, prevents, delays activation of, inactivates, desensitizes, or down-regulates, e.g., a gene, protein, ligand, receptor, or cell. An inhibitor can also be defined as a molecule that reduces, blocks, or inactivates a constitutive activity of a cell or organism.

Intracellular Domain: As used herein the term "intracellular domain" or its abbreviation "ICD" refers to the portion of a cell surface protein (e.g., a cell surface receptor) which is inside of the plasma membrane of a cell. The ICD may include the entire cytoplasmic portion of a transmembrane protein or membrane associated protein, or intracellular protein.

Isolated: As used herein the term "isolated" is used in reference to a polypeptide of interest that, if naturally occurring, is in an environment different from that in which it can naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was synthesized, for example isolated from a recombinant cell culture comprising cells engineered to express the polypeptide or by a solution resulting from solid phase synthetic means.

Kabat Numbering: The term "Kabat numbering" as used herein is recognized in the art and refers to a system of numbering amino acid residues which are more variable than other amino acid residues (e.g., hypervariable) in the heavy and light chain regions of immunoglobulins (Kabat, et al., (1971) *Ann. NY Acad Sci.* 190:382-93; Kabat, et al., (1991) *Sequences of Proteins of Immunological Interest*, Fifth Edition, U.S. Department of Health and Human Services, NIH Publication No. 91-3242). The term "Chothia Numbering" as used herein is recognized in the arts and refers to a system of numbering amino acid residues based on the location of the structural loop regions (Chothia et al. 1986, Science 233:755-758; Chothia & Lesk 1987, JMB 196:901-917; Chothia et al. 1992, JMB 227:799-817). For purposes of the present disclosure, unless otherwise specifically identified, the positioning of CDRs 2 and 3 in the variable region of an antibody follows Kabat numbering or simply, "Kabat." The positioning of CDR1 in the variable region of an antibody follows a hybrid of Kabat and Chothia numbering schemes.

Ligand: As used herein, the term "ligand" refers to a molecule that specifically binds a receptor and causes a change in the receptor so as to effect a change in the activity of the receptor or a response in cell that expresses that receptor. In one embodiment, the term "ligand" refers to a molecule or complex thereof that can act as an agonist or antagonist of a receptor. As used herein, the term "ligand" encompasses natural and synthetic ligands. "Ligand" also encompasses small molecules, peptide mimetics of cytokines and antibodies. The complex of a ligand and receptor is termed a "ligand-receptor complex." A ligand may comprise one domain of a polyprotein or fusion protein (e.g., either domain of an antibody/ligand fusion protein).

Modulate: As used herein, the terms "modulate", "modulation" and the like refer to the ability of a test agent to cause a response, either positive or negative or directly or indirectly, in a system, including a biological system, or biochemical pathway. The term modulator includes both agonists (including partial agonists, full agonists and superagonists) and antagonists.

Neoplastic Disease: As used herein, the term "neoplastic disease" refers to disorders or conditions in a subject arising from cellular hyper-proliferation or unregulated (or dysregulated) cell replication. The term neoplastic disease refers to disorders arising from the presence of neoplasms in the subject. Neoplasms may be classified as: (1) benign (2) pre-malignant (or "pre-cancerous"); and (3) malignant (or "cancerous"). The term "neoplastic disease" includes neoplastic-related diseases, disorders and conditions referring to conditions that are associated, directly or indirectly, with neoplastic disease, and includes, e.g., angiogenesis and precancerous conditions such as dysplasia or smoldering multiple myeloma. Examples of benign disorders arising from dysregulated cell replication include hypertrophic scars such as keloid scars.

Nucleic Acid: The terms "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Operably Linked: The term "operably linked" is used herein to refer to the relationship between molecules, typically polypeptides or nucleic acids, which are arranged in a construct such that each of the functions of the component molecules is retained although the operable linkage may result in the modulation of the activity, either positively or negatively, of the individual components of the construct. For example, the operable linkage of a polyethylene glycol (PEG) molecule to a wild-type protein may result in a construct where the biological activity of the protein is diminished relative to the to the wild-type molecule, however the two are nevertheless considered operably linked. When the term "operably linked" is applied to the relationship of multiple nucleic acid sequences encoding differing functions, the multiple nucleic acid sequences when combined into a single nucleic acid molecule that, for example, when introduced into a cell using recombinant technology, provides a nucleic acid which is capable of effecting the transcription and/or translation of a particular nucleic acid sequence in a cell. For example, the nucleic acid sequence encoding a signal sequence may be considered operably linked to DNA encoding a polypeptide if it results in the expression of a preprotein whereby the signal sequence facilitates the secretion of the polypeptide; a promoter or enhancer is considered operably linked to a coding sequence if it affects the transcription of the sequence; or a ribosome binding site is considered operably linked to a coding sequence if it is positioned so as to facilitate translation. Generally, in the context of nucleic acid molecules, the term "operably linked" means that the nucleic acid sequences being linked are contiguous, and, in the case of a secretory leader or associated subdomains of a molecule, contiguous and in reading phase. However, certain genetic elements such as enhancers may function at a distance and need not be contiguous with respect to the sequence to which they provide their effect but nevertheless may be considered operably linked.

Parent Polypeptide: As used herein, the terms "parent polypeptide" or "parent protein" are used interchangeably to designate the source of a second polypeptide (e.g., a derivative, mutein or variant) which is modified with respect to a first "parent" polypeptide. In some instances, the parent polypeptide is a wild-type or naturally occurring form of a protein. In some instance, the parent polypeptide may be a modified form a naturally occurring protein that is further modified. The term "parent polypeptide" may refer to the polypeptide itself or compositions that comprise the parent polypeptide (e.g., glycosylated or PEGylated forms and/or fusion proteins comprising the parent polypeptide).

Partial Agonist: As used herein, the term "partial agonist" refers to a molecule that specifically binds that bind to and activate a given receptor but possess only partial activation the receptor relative to a full agonist. Partial agonists may display both agonistic and antagonistic effects. For example, when both a full agonist and partial agonist are present, the partial agonist acts as a competitive antagonist by competing with the full agonist for the receptor binding resulting in net decrease in receptor activation relative to the contact of the receptor with the full agonist in the absence of the partial agonist. Partial agonists can be used to activate receptors to give a desired submaximal response in a subject when inadequate amounts of the endogenous ligand are present, or they can reduce the overstimulation of receptors when excess amounts of the endogenous ligand are present. The maximum response ($E_{max}$) produced by a partial agonist is called its intrinsic activity and may be expressed on a percentage scale where a full agonist produced a 100% response. An partial agonist may have greater than 10% but less than 100%, alternatively greater than 20% but less than 100%, alternatively greater than 30% but less than 100%, alternatively greater than 40% but less than 100%, alternatively greater than 50% but less than 100%, alternatively greater than 60% but less than 100%, alternatively greater than 70% but less than 100%, alternatively greater than 80% but less than 100%, or alternatively greater than 90% but less than 100%, of the activity of the reference polypeptide when evaluated at similar concentrations in a given assay system.

Polypeptide: As used herein the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The term polypeptide include fusion proteins, including, but not limited to, fusion proteins with a heterologous amino acid sequence; fusion proteins with heterologous and homologous leader sequences; fusion proteins with or without N-terminal methionine residues; fusion proteins with amino acid sequences that facilitate purification such as chelating peptides; fusion proteins with immunologically tagged proteins; fusion proteins comprising a peptide with immunologically active polypeptide fragment (e.g., antigenic diphtheria or tetanus toxin or toxoid fragments) and the like.

Prevent: As used herein the terms "prevent", "preventing", "prevention" and the like refer to a course of action initiated with respect to a subject prior to the onset of a disease, disorder, condition or symptom thereof so as to prevent, suppress, inhibit or reduce, either temporarily or permanently, a subject's risk of developing a disease, disorder, condition or the like (as determined by, for example, the absence of clinical symptoms) or delaying the onset thereof. A course of action to prevent a disease, disorder or condition in a subject is typically applied in the context of a subject who is predisposed to developing a disease, disorder or condition due to genetic, experiential or environmental factors of developing a particular disease, disorder or condition. In certain instances, the terms "prevent", "preventing", "prevention" are also used to refer to the slowing of the progression of a disease, disorder or condition from an existing state to a more deleterious state.

Receptor: As used herein, the term "receptor" refers to a polypeptide having a domain that specifically binds a ligand that binding of the ligand results in a change to at least one biological property of the polypeptide. In some embodiments, the receptor is a cell membrane associated protein that comprises and extracellular domain (ECD) and a membrane associated domain which serves to anchor the ECD to the cell surface. In some embodiments of cell surface receptors, the receptor is a membrane spanning polypeptide comprising an intracellular domain (ICD) and extracellular domain (ECD) linked by a membrane spanning domain typically referred to as a transmembrane domain (TM). The binding of a cognate ligand to the receptor results in a conformational change in the receptor resulting in a measurable biological effect. In some instances, where the receptor is a membrane spanning polypeptide comprising an ECD, TM and ICD, the binding of the ligand to the ECD results in a measurable intracellular biological effect mediated by one or more domains of the ICD in response to the binding of the ligand to the ECD. In some embodiments, a receptor is a component of a multi-component complex to facilitate intracellular signaling. For example, the ligand may bind a cell surface receptor that is not associated with any intracellular signaling alone but upon ligand binding facilitates the formation of a heteromultimeric (including heterodimeric, heterotrimeric, etc.) or homomultimeric (including homodimeric, homotrimeric, homotetrameric, etc.) complex that results in a measurable biological effect in the cell such as activation of an intracellular signaling cascade (e.g., the Jak/STAT pathway). In some embodiments, a receptor is a membrane spanning single chain polypeptide comprising ECD, TM and ICD domains wherein the ECD, TM and ICD domains are derived from the same or differing naturally occurring receptor variants or synthetic functional equivalents thereof Recombinant: As used herein, the term "recombinant" is used as an adjective to refer to the method by which a polypeptide, nucleic acid, or cell was modified using recombinant DNA technology. A "recombinant protein" is a protein produced using recombinant DNA technology and is frequently abbreviated with a lower case "r" preceding the protein name to denote the method by which the protein was produced (e.g., recombinantly produced human growth hormone is commonly abbreviated "rhGH"). Similarly, a cell is referred to as a "recombinant cell" if the cell has been modified by the incorporation (e.g., transfection, transduction, infection) of exogenous nucleic acids (e.g., ssDNA, dsDNA, ssRNA, dsRNA, mRNA, viral or non-viral vectors, plasmids, cosmids and the like) using recombinant DNA technology. The techniques and protocols for recombinant DNA technology are well known in the art such as those can be found in Sambrook, et al. (1989) Molecular Cloning: A Laboratory Manual (2d ed., Cold Spring Harbor Laboratory Press, Plainview, N.Y.) and other standard molecular biology laboratory manuals.

Response: The term "response," for example, of a cell, tissue, organ, or organism, encompasses a quantitative or qualitative change in a evaluable biochemical or physiological parameter, (e.g., concentration, density, adhesion, proliferation, activation, phosphorylation, migration, enzymatic activity, level of gene expression, rate of gene expression, rate of energy consumption, level of or state of differentiation) where the change is correlated with the activation, stimulation, or treatment, with or contact with exogenous agents or internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects. A "response" may be evaluated in vitro such as through the use of assay systems, surface plasmon resonance, enzymatic activity, mass spectroscopy, amino acid or protein sequencing technologies. A "response" may be evaluated in vivo quantitatively by evaluation of objective physiological parameters such as body temperature, bodyweight, tumor volume, blood pressure, results of X-ray or other imaging technology or qualitatively through changes in reported subjective feelings of well-being, depression, agitation, or pain. In some embodiments, the level of proliferation of CD3 activated primary human T-cells may be evaluated in a bioluminescent assay that generates a luminescent signal that is proportional to the amount of ATP present which is directly proportional to the number of cells present in culture as described in Crouch, et al. (1993) J. Immunol. Methods 160: 81-8 or using commercially available assays such as the CellTiter-Glo® 2.0 Cell Viability Assay or CellTiter-Glo® 3D Cell Viability kits commercially available from Promega Corporation, Madison Wis. 53711 as catalog numbers G9241 and G9681 in substantial accordance with the instructions provided by the manufacturer. In some embodiments, the level of activation of T cells in response to the administration of a test agent may be determined by flow cytometric methods as described as determined by the level of STAT (e.g., STAT1, STAT3, STAT5) phosphorylation in accordance with methods well known in the art.

Significantly Reduced Binding: As used herein, the term "exhibits significantly reduced binding" is used with respect a variant of a first molecule (e.g., a ligand or antibody) which exhibits a significant reduction in the affinity for a second molecule (e.g., receptor or antigen) relative the parent form of the first molecule. With respect to antibody variants, an antibody variant "exhibits significantly reduced binding" if the affinity of the variant antibody for an antigen if the variant binds to the native form of the receptor with and affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent antibody from which the variant was derived. Similarly, with respect to variant ligands, a variant ligand "exhibits significantly reduced binding" if the affinity of the variant ligand binds to a receptor with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent ligand from which the variant ligand was derived. Similarly, with respect to variant receptors, a variant ligand "exhibits significantly reduced binding" if the affinity of the variant receptors binds to a with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent receptor from which the variant receptor was derived.

Small Molecule(s): The term "small molecules" refers to chemical compounds (typically pharmaceutically active compounds) having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. The term "small molecule" is a term well understood to those of ordinary skill in the pharmaceutical arts and is typically used to distinguish organic chemical compounds from biologics.

Specifically Binds: As used herein the term "specifically binds" refers to the degree of affinity for which a first molecule exhibits with respect to a second molecule. In the context of binding pairs (e.g., ligand/receptor, antibody/antigen) a first molecule of a binding pair is said to specifically bind to a second molecule of a binding pair when the first molecule of the binding pair does not bind in a significant amount to other components present in the sample. A first molecule of a binding pair is said to specifically bind to a second molecule of a binding pair when the first molecule of the binding pair when the affinity of the first molecule for the second molecule is at least two-fold greater, alternatively at least five times greater, alternatively at least ten times greater, alternatively at least 20-times greater, or alternatively at least 100-times greater than the affinity of the first molecule for other components present in the sample. In a particular embodiment, where the first molecule of the binding pair is an antibody, the antibody specifically binds to the antigen (or antigenic determinant (epitope) of a protein, antigen, ligand, or receptor) if the equilibrium dissociation constant between antibody and the antigen is greater than about $10^6$ M, alternatively greater than about $10^8$ M, alternatively greater than about $10^{10}$ M, alternatively greater than about $10^{11}$ M, greater than about $10^{12}$ M as determined by, e.g., Scatchard analysis (Munsen, et al. (1980) Analyt. Biochem. 107:220-239). In one embodiment where the ligand is an IL10Ra binding sdAb and the receptor comprises an IL10Ra, the IL10Ra binding sdAb specifically binds if the equilibrium dissociation constant of the IL10Ra binding sdAb/IL10Ra ECD is greater than about $10^5$M, alternatively greater than about $10^6$ M, alternatively greater than about $10^7$M, alternatively greater than about $10^8$M, alternatively greater than about $10^9$M, alternatively greater than about $10^{10}$ M, or alternatively greater than about $10^{11}$ M. Specific binding may be assessed using techniques known in the art including but not limited to competition ELISA assays, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays)) and surface plasmon resonance assays (see, e.g., Drescher et al., (2009) Methods Mol Biol 493:323-343 with commercially available instrumentation such as the Biacore 8K, Biacore 8K+, Biacore S200, Biacore T200 (Cytiva, 100 Results Way, Marlborough Mass. 01752). In some embodiments, the present disclosure provides molecules (e.g., IL10Ra binding sdAbs) that specifically bind to hIL10Ra.

As used herein, the binding affinity of an IL10Ra binding molecule for hIL10Ra, the binding affinity may be determined and/or quantified by surface plasmon resonance ("SPR"). In evaluating binding affinity of an IL10Ra binding molecule for IL10Ra, either member of the binding pair may be immobilized, and the other element of the binding pair be provided in the mobile phase. In some embodiments, the sensor chip on which the protein of interest is to be immobilized is conjugated with a substance to facilitate binding of the protein of interest such as nitrilotriacetic acid (NTA) derivatized surface plasmon resonance sensor chips (e.g., Sensor Chip NTA available from Cytiva Global Life Science Solutions USA LLC, Marlborough Mass. as catalog number BR100407), as anti-His tag antibodies (e.g. anti-histidine CM5 chips commercially available from Cytiva, Marlborough Mass.), protein A or biotin. Consequently, to evaluate binding, it is frequently necessary to modify the protein to provide for binding to the substance conjugated to the surface of the chip. For example, the one member of the binding pair to be evaluated by incorporation of a chelating peptide comprising poly-histidine sequence (e.g., 6×His (SEQ ID NO: 93) or 8×His (SEQ ID NO: 94)) for retention on a chip conjugated with NTA. In some embodiments, the IL10Ra binding molecule may be immobilized on the chip and IL10Ra (or ECD fragment thereof) be provided in the mobile phase. Alternatively, the IL10Ra (or ECD fragment thereof) may be immobilized on the chip and the IL10Ra binding molecule be provided in the mobile phase. In either circumstance, it should be noted that modifications of some proteins for immobilization on a coated SPR chip may interfere with the binding properties of one or both components of the binding pair to be evaluated by SPR. In such cases, it may be necessary to switch the mobile and bound elements of the binding pair or use a chip with a binding agent that facilitates non-interfering conjugation of the protein to be evaluated. Alternatively, when evaluating the binding affinity of IL10Ra binding molecule for IL10Ra using SPR, the IL10Ra binding molecule may be derivatized by the C-terminal addition of a poly-His sequence (e.g., 6×His (SEQ ID NO: 93) or 8×His (SEQ ID NO: 94)) and immobilized on the anti-histidine sensor chip and the hIL10 receptor subunit for which the binding affinity is being evaluated is provided in the mobile phase. The means for incorporation of a poly-His sequence into the C-terminus of the IL10Ra binding molecule produced by recombinant DNA technology is well known to those of skill in the relevant art of biotechnology. In some embodiments, the binding affinity of IL10Ra binding molecule for a IL10Ra using SPR substantial accordance with the teaching of the Examples.

Subject: The terms "recipient", "individual", "subject", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is a human being.

Substantially Pure: As used herein, the term "substantially pure" indicates that a component of a composition makes up greater than about 50%, alternatively greater than about 60%, alternatively greater than about 70%, alternatively greater than about 80%, alternatively greater than about 90%, alternatively greater than about 95% of the total content of the composition. A protein that is "substantially pure" comprises greater than about 50%, alternatively greater than about 60%, alternatively greater than about 70%, alternatively greater than about 80%, alternatively greater than about 90%, alternatively greater than about 95% of the total content of the composition.

Suffering From: As used herein, the term "suffering from" refers to a determination made by a physician with respect to a subject based on the available objective or subjective information accepted in the field for the identification of a disease, disorder or condition including but not limited to X-ray, CT-scans, conventional laboratory diagnostic tests (e.g., blood count, etc.), genomic data, protein expression data, immunohistochemistry, that the subject requires or will benefit from treatment. The term suffering from is typically used in conjunction with a particular disease state such as "suffering from a neoplastic disease" refers to a subject which has been diagnosed with the presence of a neoplasm.

T-cell: As used herein the term "T-cell" or "T cell" is used in its conventional sense to refer to a lymphocyte that differentiates in the thymus, possess specific cell-surface antigen receptors, and include some that control the initiation or suppression of cell-mediated and humoral immunity and others that lyse antigen-bearing cells. In some embodiments the T cell includes without limitation naïve CD8$^+$ T cells, cytotoxic CD8$^+$ T cells, naïve CD4$^+$ T cells, helper T cells, e.g., $T_H1$, $T_H2$, $T_H9$, $T_H11$, $T_H22$, $T_{FH}$; regulatory T cells, e.g., $T_R1$, Tregs, inducible Tregs; memory T cells, e.g., central memory T cells, effector memory T cells, NKT cells, tumor infiltrating lymphocytes (TILs) and engineered variants of such T-cells including but not limited to CAR-T cells, recombinantly modified TILs and TCR-engineered cells. In some embodiments the T cell is a T cell expressing the IL10Ra isoform referred to interchangeably as IL10Ra cell, IL10Ra+ cell, IL10Ra T cell, or IL10Ra+ T cell).

Terminus/Terminal: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" refers to the position of a first amino acid residue relative to a second amino acid residue in a contiguous polypeptide sequence, the first amino acid being closer to the N-terminus of the polypeptide. "Immediately C-terminal" refers to the position of a first amino acid residue relative to a second amino acid residue in a contiguous polypeptide sequence, the first amino acid being closer to the C-terminus of the polypeptide.

Therapeutically Effective Amount: As used herein to the phrase "therapeutically effective amount" refers to the quantity of an agent when administered to a subject, either alone or as part of a pharmaceutical composition or treatment regimen, in a single dose or as part of a series of doses, provides a positive effect on any quantitative or qualitative symptom, aspect, or characteristic of a disease, disorder or condition. A therapeutically effective amount can be ascertained by measuring relevant physiological effects, and it may be adjusted in connection with a dosing regimen and in response to diagnostic analysis of the subject's condition. The parameters for evaluation to determine a therapeutically effective amount of an agent are determined by the physician using art accepted diagnostic criteria including but not limited to indicia such as age, weight, sex, general health, ECOG score, observable physiological parameters, blood levels, blood pressure, electrocardiogram, computerized tomography, X-ray, and the like. Alternatively, or in addition, other parameters commonly assessed in the clinical setting may be monitored to determine if a therapeutically effective amount of an agent has been administered to the subject such as body temperature, heart rate, normalization of blood chemistry, normalization of blood pressure, normalization of cholesterol levels, or any symptom, aspect, or characteristic of the disease, disorder or condition, biomarkers (such as inflammatory cytokines, IFN-g, granzyme, and the like), reduction in serum tumor markers, improvement in Response Evaluation Criteria In Solid Tumors (RECIST), improvement in Immune-Related Response Criteria (irRC), increase in duration of survival, extended duration of progression free survival, extension of the time to progression, increased time to treatment failure, extended duration of event free survival, extension of time to next treatment, improvement objective response rate, improvement in the duration of response, reduction of tumor burden, complete response, partial response, stable disease, and the like that that are relied upon by clinicians in the field for the assessment of an improvement in the condition of the subject in response to administration of an agent. In one embodiment, a therapeutically effective amount is an amount of an agent when used alone or in combination with another agent provides an provides a positive effect on any quantitative or qualitative symptom, aspect, or characteristic of a disease, disorder or condition and does not result in non-reversible serious adverse events in the course of administration of the agent to the mammalian subject.

Transmembrane Domain: The term "transmembrane domain" or "TM" refers to a polypeptide domain of a membrane spanning polypeptide (e.g., a transmembrane receptor) which, when the membrane spanning polypeptide is associated with a cell membrane, is which is embedded in the cell membrane and is in peptidyl linkage with the extracellular domain (ECD) and the intracellular domain (ICD) of a membrane spanning polypeptide. A transmembrane domain may be homologous (naturally associated with) or heterologous (not naturally associated with) with either or both of the extracellular and/or intracellular domains. In some embodiments, where the receptor is chimeric receptor comprising the intracellular domain derived from a first parental receptor and a second extracellular domains are derived from a second different parental receptor, the transmembrane domain of the chimeric receptor is the transmembrane domain normally associated with either the ICD or the ECD of the parent receptor from which the chimeric receptor is derived.

Treat: The terms "treat", "treating", treatment" and the like refer to a course of action (such as contacting the subject with pharmaceutical composition comprising a IL10Ra binding sdAb alone or in combination with a supplementary agent) that is initiated with respect to a subject in response to a diagnosis that the subject is suffering from a disease, disorder or condition, or a symptom thereof, the course of action being initiated so as to eliminate, reduce, suppress, mitigate, or ameliorate, either temporarily or permanently, at least one of: (a) the underlying causes of such disease, disorder, or condition afflicting a subject; and/or (b) at least one of the symptoms associated with such disease, disorder, or condition. In some embodiments, treating includes a course of action taken with respect to a subject suffering from a disease where the course of action results in the inhibition (e.g., arrests the development of the disease, disorder or condition or ameliorates one or more symptoms associated therewith) of the disease in the subject.

Treg Cell or Regulatory T Cell. The terms "regulatory T cell", "Treg cell", or "Treg" are interchangeably herein to refers to a type of $CD4^+$ T cell that can suppress the responses of other T cells including but not limited to effector T cells ($T_{eff}$). Treg cells are typically characterized by expression of CD4 (CD4+), the CD25 subunit of the IL2 receptor (CD25+), and the transcription factor forkhead box P3 (FOXP3+) (Sakaguchi, Annu Rev Immunol 22, 531-62 (2004). In some instances, the term "conventional $CD4^+$ T cells" is used to distinguish non-Treg $CD4^+$ T cells from $CD4^+$ Tregs.

Variant: The terms "variant", "protein variant" or "variant protein" or "variant polypeptide" are used interchangeably herein to refer to a polypeptide that differs from a parent polypeptide by virtue of at least one amino acid modification, substitution, or deletion. The parent polypeptide may be a naturally occurring or wild-type (WT) polypeptide or may be a modified version of a WT polypeptide. The term variant polypeptide may refer to the polypeptide itself, a composition comprising the polypeptide, or the nucleic acid sequence that encodes it. In some embodiments, the variant polypeptide comprises from about one to about ten, alternatively about one to about eight, alternatively about one to about seven, alternatively about one to about five, alternatively about one to about four, alternatively from about one to about three alternatively from one to two amino acid modifications, substitutions, or deletions, or alternatively a single amino acid amino acid modification, substitution, or deletion compared to the parent polypeptide. A variant may be at least about 99% identical, alternatively at least about 98% identical, alternatively at least about 97% identical, alternatively at least about 95% identical, or alternatively at least about 90% identical to the parent polypeptide from which the variant is derived.

Wild Type: By "wild type" or "WT" or "native" herein is meant an amino acid sequence or a nucleotide sequence that is found in nature, including allelic variations. A wild-type protein, polypeptide, antibody, immunoglobulin, IgG, etc. has an amino acid sequence or a nucleotide sequence that has not been modified by the hand of man.

IL10Ra

The IL10Ra binding molecules of the present disclosure specifically bind to the extracellular domain of the IL10Ra.

The present disclosure provides molecules that specifically bind to the extracellular domain of IL10Ra.

The present disclosure provides a IL10Ra binding molecule that specifically binds to the extracellular domain of IL10Ra (e.g., human IL10Ra).

In some embodiments, the IL10Ra binding molecule comprises a single domain antibody (sdAb) that specifically binds to the extracellular domain of the human IL10Ra.

Human IL10Ra

In one embodiment, the IL10Ra is the human IL10Ra. The canonical full length IL10Ra is a polypeptide possessing the amino acid sequence:

(SEQ ID NO: 91)
MLPCLVVLLAALLSLRLGSDAHGTELPSPPSVWFEAEFFHHILHWTPIPN

QSESTCYEVALLRYGIESWNSISNCSQTLSYDLTAVTLDLYHSNGYRARV

RAVDGSRHSNWTVTNTRFSVDEVTLTVGSVNLEIHNGFILGKIQLPRPKM

APANDTYESIFSHFREYEIAIRKVPGNFTFTHKKVKHENFSLLTSGEVGE

FCVQVKPSVASRSNKGMWSKEECISLTRQYFTVTNVIIFFAFVLLLSGAL

AYCLALQLYVRRRKKLPSVLLFKKPSPFIFISQRPSPETQDTIHPLDEEA

FLKVSPELKNLDLHGSTDSGFGSTKPSLQTEEPQFLLPDPHPQADRTLGN

REPPVLGDSCSSGSSNSTDSGICLQEPSLSPSTGPTWEQQVGSNSRGQDD

SGIDLVQNSEGRAGDTQGGSALGHHSPPEPEVPGEEDPAAVAFQGYLRQT

RCAEEKATKTGCLEEESPLTDGLGPKFGRCLVDEAGLHPPALAKGYLKQD

PLEMTLASSGAPTGQWNQPTEEWSLLALSSCSDLGISDWSFAHDLAPLGC

VAAPGGLLGSFNSDLVTLPLISSLQSSE

For purposes of the present disclosure, the numbering of amino acid residues of the human IL10Ra polypeptides as described herein is made in accordance with the numbering of this canonical sequence UniProg Database Reference No. Q13651. Amino acids 1-21 of SEQ ID NO:91 are identified as the signal peptide of the IL10Ra, amino acids 22-235 of SEQ ID NO:1 are identified as the extracellular domain, amino acids 236-256 of SEQ ID NO:91 are identified as the transmembrane domain, and amino acids 257-578 of SEQ ID NO:91 are identified as the intracellular domain.

To generate sdAbs against the human IL10Ra, the extracellular domain of the hIL10Ra protein may be used an immunogen. The extracellular domain of the mature (lacking the signal sequence) hIL10Ra possesses the amino acid sequence (amino acids 22-235 of SEQ ID NO:91) has the amino acid sequence (SEQ ID NO: 92)
HGTELPSPPSVWFEAEFFHHILHWTPIPNQSESTCYEVALLRYGIESWNS

ISNCSQTLSYDLTAVTLDLYHSNGYRARVRAVDGSRHSNWTVTNTRFSVD

EVTLTVGSVNLEIHNGFILGKIQLPRPKMAPANDTYESIFSHFREYEIAI

RKVPGNFTFTHKKVKHENFSLLTSGEVGEFCVQVKPSVASRSNKGMWSKE

ECISLTRQYFTVTN

IL10Ra Binding Molecules and Single Domain Antibodies

In some embodiments, a IL10Ra binding molecule of the present disclosure is a single domain antibody (sdAb). The present disclosure relates to IL10Ra binding molecules comprising single domain antibodies (sdAbs) that specifically bind to the extracellular domain of the human IL10Ra isoform (hIL10Ra) which are found on all IL10Ra-expressing cells.

A single-domain antibody (sdAb) is an antibody containing a single monomeric variable antibody domain. Like a full-length antibody, sdAbs bind specifically to an antigenic determinant. hIL10Ra binding VHH single-domain antibodies can be engineered from heavy chain antibodies isolated from Camelidae mammals (e.g., camels, llamas, dromedary, alpaca, and guanaco) immunized with the extracellular domain of hIL10Ra or an immunologically active fragment thereof. Descriptions of sdAbs and VHHs can be found in, e.g., De Greve et al., (2019) Curr Opin Biotechnol. 61:96-101; Ciccarese, et al., (2019) Front Genet. 10:997: Chanier and Chames (2019) Antibodies (Basel) 8(1); and De Vlieger, et al. (2018) Antibodies (Basel) 8(1). Alternatively, hIL10Ra single domain antibodies may be engineered from heavy chain antibodies isolated from the IgNAR heavy chain antibodies isolated from cartilaginous fishes immunized with the extracellular domain of hIL10Ra or an immunologically active fragment thereof hIL10Ra binding sdAbs may also be obtained by splitting the dimeric variable domains from immunoglobulin G (IgG) isotypes from other mammalian species including humans, rats, rabbits immunized with the extracellular domain of hIL10Ra or an immunologically active fragment thereof. Although most research into sdAbs is currently based on heavy chain variable domains, sdAbs derived from light chains have also been shown to bind specifically to the target proteins comprising the antigenic immunization sequence. Moller et al., *J Biol Chem.* 285(49):38348-38361, 2010.

In some embodiments, the sdAb is a VHH. A VHH is a type of sdAb that has a single monomeric heavy chain variable antibody domain. Similar to a traditional antibody, a VHH is able to bind specifically to a specific antigen. An exemplary VHH has a molecular weight of approximately 12-15 kDa which is much smaller than traditional mammalian antibodies (150-160 kDa) composed of two heavy chains and two light chains. VHHs can be found in or produced from Camelidae mammals (e.g., camels, llamas, dromedary, alpaca, and guanaco) which are naturally devoid of light chains.

The present disclosure provides IL10Ra binding molecules comprising a polypeptide having at least 75%, alternatively 80%, alternatively 90%, alternatively 95%, alternatively 98%, or alternatively 99% or 100% identity to a polypeptide of any one of SEQ ID NOS: SEQ ID NOS:1, 5, 9, 13, 17, 21, 25, 29, 33, 37, 41, 45, 49, 53, 57, 61, 65, 69.

The present disclosure provides IL10Ra binding molecules comprising a CDR1, a CDR2, and a CDR3 as described in a row of Table 1A provided herein. In some embodiments, the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 1 provided herein.

Experimental

The single domain antibodies of the present disclosure were obtained from camels by immunization with an extracellular domain of a human IL10Ra receptor (hIL10Ra). IL10Ra VHH molecules of the present disclosure of the present disclosure were generated in substantial accordance with the teaching of the Examples. Briefly, a camel was sequentially immunized with the ECD of the human IL10Ra and mouse IL10Ra over a period several weeks of by the subcutaneous an adjuvanted composition containing a recombinantly produced fusion proteins comprising the extracellular domain of the IL10Ra, the human IgG1 hinge domain and the human IgG1 heavy chain Fc. Following immunization, RNAs extracted from a blood sample of appropriate size VHH-hinge-CH2-CH3 species were transcribed to generate DNA sequences, digested to identify the approximately 400 bp fragment comprising the nucleic acid sequence encoding the VHH domain was isolated. The isolated sequence was digested with restriction endonucleases to facilitate insertion into a phagemid vector for in frame with a sequence encoding a his-tag and transformed into E. coli to generate a phage library. Multiple rounds of bio-panning of the phage library were conducted to identify VHHs that bound to the ECD of IL10Ra (human or mouse as appropriate). Individual phage clones were isolated for periplasmic extract ELISA (PE-ELISA) in a 96-well plate format and selective binding confirmed by colorimetric determination. The IL10Ra binding molecules that demonstrated specific binding to the IL10Ra antigen were isolated and sequenced and sequences analyzed to identify VHH sequences, CDRs and identify unique VHH clonotypes. As used herein, the term "clonotypes" refers a collection of binding molecules that originate from the same B-cell progenitor cell, in particular, a collection of antigen binding molecules that belong to the same germline family, have the same CDR3 lengths, and have 70% or greater homology in CDR3 sequence. The VHH molecules demonstrating specific binding to the hIL10Ra ECD antigen (anti-human IL10Ra VHHs) and the CDRs isolated from such VHHs are provided in Table 1. Nucleic acid sequences encoding the VHHs of Table 1 are provided in Table 2.

To more fully characterize the binding properties and evaluate binding affinity of the VHH molecules generated in accordance with the foregoing, representative examples of each of the human VHH clonotypes were subjected to analysis of by surface plasmon resonance in substantial accordance with the teaching of Example 5 herein. The results of these SPR studies are summarized in Table 4 below.

affinity and/or specific binding described elsewhere herein such as flow cytometry or SPR. Consequently, the use of the term "human IL10Ra VHH" or "hIL10Ra VHH" merely denotes that the species of the IL10Ra antigen used for immunization of the camelid from which the VHH was derived was the human IL10Ra (e.g., the IL10Ra, ECD, SEQ ID NO:192 but should not be understood as limiting with respect to the specific binding affinity of the VHH for IL10Ra molecules of other mammalian species. Similarly, the use of the term "mouse IL10Ra VHH" or "mIL10Ra VHH" merely denotes that the species of the IL10Ra antigen used for immunization of the camelid from which the VHH was derived was the murine IL10Ra (e.g., the mIL10Ra ECD, SEQ ID NO:194) but should not be understood as limiting with respect to the specific binding affinity of the VHH for IL10Ra molecules of other mammalian species.

Modified Forms of Single Domain Antibodies

CDR Grafted sdAbs

In some embodiments, the IL10Ra binding sdAb of the present disclosure is a CDR grafted IL10Ra binding sdAb. CDRs obtained from antibodies, heavy chain antibodies, and sdAbs derived therefrom may be grafted onto alternative frameworks as described in Saerens, et al. (2005) J. Mol Biol 352:597-607 to generate CDR-grafted sdAbs. In some embodiments, the present disclosure provides a IL10Ra binding molecule comprising a CDR grafted IL10Ra binding sdAb, said CDR-grafted IL10Ra binding sdAb comprising a set of CDRs1, 2, and 3 as shown in a row of the Table 1A above. In some embodiments, the present disclosure provides a IL10Ra binding molecule comprising a CDR grafted IL10Ra binding sdAb, said CDR-grafted IL10Ra

TABLE 4 anti-hIL10Ra Mono-Fc VHHs binding to hIL10Ra-his
(Antigen: Sino Biological, Catalog #10419)

| Ligand | SEQ ID NO | $k_{ON}$ (1/Ms) | $k_{OFF}$ (1/s) | Affinity (nM) | Rmax (RU) | Load (RU) | Calc. Rmax (RU) | Surface Activity |
|---|---|---|---|---|---|---|---|---|
| hIL-10Ra_VHH10 | 37 | 1.04E+05 | 1.39E−03 | 13.4 | 106 | 242 | 185 | 57% |
| hIL-10Ra_VHH6 | 21 | 1.06E+05 | 1.90E−04 | 1.8 | 31.8 | 50.2 | 38 | 83% |
| hIL-10Ra_VHH8 | 29 | 1.68E+05 | 1.07E−03 | 6.4 | 17.7 | 40.6 | 31 | 57% |
| hIL-10Ra_VHH9 | 33 | 9.97E+04 | 1.15E−03 | 11.6 | 42.2 | 83.2 | 64 | 66% |
| hIL-10Ra_VHH12 | 45 | 1.54E+05 | 1.19E−03 | 7.7 | 18.3 | 32.9 | 25 | 73% |
| hIL-10Ra_VHH14 | 53 | 9.84E+04 | 1.36E−04 | 1.4 | 17.1 | 44.1 | 34 | 51% |
| hIL-10Ra_VHH17 | 65 | 3.27E+05 | 1.97E−03 | 6 | 48.4 | 180 | 137 | 35% |

In As illustrated by the data presented in Table 4, the hIL10Ra binding molecules generated in accordance with the teaching of present disclosure exhibit specific binding and provided a range of affinities to the extracellular domain of hIL10Ra.

In some instances, due to sequence or structural similarities between the extracellular domains of IL10Ra receptors from various mammalian species, immunization with an antigen derived from a IL10Ra of a first mammalian species (e.g., the hIL10Ra-ECD) may provide antibodies which specifically bind to IL10Ra receptors of one or more additional mammalian species. Such antibodies are termed "cross reactive." For example, immunization of a camelid with a human derived antigen (e.g., the hIL10Ra-ECD) may generate antibodies that are cross-reactive the murine and human receptors. Evaluation of cross-reactivity of antibody with respect to the receptors derived from other mammalian species may be readily determined by the skilled artisan, for example using the methods relating to evaluation of binding binding sdAb comprising a set of CDRs1, 2, and 3 as shown in a row of the Table 1B above.

Chimeric and Humanized sdAbs

Any framework region can be used with the CDRs as described herein. In some embodiments, the IL10Ra binding sdAb is a chimeric sdAb, in which the CDRs are derived from one species (e.g., camel) and the framework and/or constant regions are derived from another species (e.g., human or mouse). In specific embodiments, the framework regions are human or humanized sequences. Thus, humanized IL10Ra binding sdAbs derived from hIL10Ra binding VHHs are considered within the scope of the present disclosure. The techniques for humanization of camelid single domain antibodies are well known in the art. See, e.g., Vincke, et al. (2009) *General Strategy to Humanize a Camelid Single-domain Antibody and Identification of a Universal Humanized Nanobody Scaffold* J. Biol. Chem. 284(5)3273-3284.

In some embodiments, a VHH described herein can be humanized to contain human framework regions. Examples of human germlines that could be used to create humanized VHHs include, but are not limited to, VH3-23 (e.g., UniProt ID: P01764), VH3-74 (e.g., UniProt ID: A0A0B4J1X5), VH3-66 (e.g., UniProt ID: A0A0C4DH42), VH3-30 (e.g., UniProt ID: P01768), VH3-11 (e.g., UniProt ID: P01762), and VH3-9 (e.g., UniProt ID: P01782).

Elimination of N-Linked Glycosylation Sites

In some embodiments, it is possible that an amino acid sequence (particularly a CDR sequence) of the hIL10Ra binding sdAb may contain a glycosylation motif, particularly an N-linked glycosylation motif of the sequence Asn-X-Ser (N-X-S) or Asn-X-Thr (N-X-T), wherein X is any amino acid except for proline. In such instances, it is desirable to eliminate such N-linked glycosylation motifs by modifying the sequence of the N-linked glycosylation motif to prevent glycosylation. In some embodiments, the elimination of the Asn-X-Ser (N-X-S) N-linked glycosylation motif may be achieved by the incorporation of conservative amino acid substitution of the Asn (N) residue and/or Ser (S) residue of the Asn-X-Ser (N-X-S) N-linked glycosylation motif. In some embodiments, the elimination of the Asn-X-Thr (N-X-T) N-linked glycosylation motif may be achieved by the incorporation of conservative amino acid substitution of the Asn (N) residue and/or Thr (T) residue of the Asn-X-Thr (N-X-T) N-linked glycosylation motif. In some embodiments, elimination of the glycosylation site is not required when the IL10Ra binding molecule is expressed in procaryotic host cells. Since procaryotic cells do not provide a mechanism for glycosylation of recombinant proteins, when employing a procaryotic expression system to produce a recombinant IL10Ra binding sdAb the modification of the sequence to eliminate the N-linked glycosylation sites may be obviated.

IL10Ra Binding Molecules Comprising Additional Agents

In some embodiments, a IL10Ra binding molecule of the present disclosure comprises a IL10Ra single domain antibody (sdAb) conjugated to one or more additional biologically active agents including but not limited to, therapeutic agents, chemically, optically or radioactively active agents, including combinations thereof. The conjugation of at least one such biologically, chemically, optically or radioactively active agent confer additional biological or chemical properties to IL10Ra binding sdAb, the combination providing a IL10Ra binding molecule possessing additional or alternative utilities.

For example, the additional agent may be a molecule selected from one or more of: immunomodulatory agents (e.g., immunogens); molecules that improve aqueous solubility (e.g., water soluble polymers and hydrophilic molecules such as sugars); carrier molecules that extend in vivo half-life (e.g., PEGylation, Fc fusions or acylation); generation of antibodies for use in detection assays (e.g., epitope tags), enhance ease of purification (e.g., chelating peptides such as poly-His tags); targeting domains that provide selective targeting IL10Ra binding molecule to a particular cell or tissue type; therapeutic agents (e.g., therapeutic agents including small molecule or polypeptide agents); agents that visibility to optical or electromagnetic sensors (e.g., radionucleotides or fluorescent agents). In some embodiments, the linker is a cleavable linker or a non-cleavable linker. The use of a cleavable linker in a IL10Ra binding molecule as contemplated herein facilitates the release of a therapeutic agent into the intracellular cytoplasm upon internalization of the IL10Ra binding molecule. A non-cleavable linker would allow release upon digestion of the IL10Ra binding molecule of or it could be used with an agent that does not require release from the antibody (e.g., an imaging agent).

In some embodiments, where the IL10Ra binding molecule comprises a IL10Ra binding sdAb in stable association with an additional agent joined via a linker. A linker is a covalent linkage between two elements of a IL10Ra binding molecule (e.g., a hIL10Ra binding VHH and PEG polymer). A linker can be a covalent bond, chemical linker or a peptide linker. Suitable linkers include "flexible linkers" which are generally of sufficient length to permit some movement between the IL10Ra binding sdAb and the linked agent(s). Examples of chemical linkers include aryl acetylene, ethylene glycol oligomers containing 2-10 monomer units, diamines, diacids, amino acids, or combinations thereof. In some embodiments, the linker is a peptide linker. Suitable peptide linkers can be readily selected and can be of any suitable length, such as 1 amino acid (e.g., Gly), 2, 3, 4, 5, 6, 7, 8, 9, 10, 10-20, 20-30, 30-50 or more than 50 amino acids. Suitable peptide linkers are known in the art, and include, for example, peptide linkers containing flexible amino acid residues such as glycine and serine. Examples of flexible linkers include glycine polymers $(G)_n$, glycine-serine polymers, glycine-alanine polymers, alanine-serine polymers, and other flexible linkers. Glycine and glycine-serine polymers are relatively unstructured, and therefore can serve as a neutral tether between components. Further examples of flexible linkers include glycine polymers $(G)_n$, glycine-alanine polymers, alanine-serine polymers, glycine-serine polymers. Glycine and glycine-serine polymers are relatively unstructured, and therefore may serve as a neutral tether between components. A multimer (e.g., 1, 2, 3, 4, 5, 6, 7, 8, 9, 10, 10-20, 20-30, or 30-50) of such linker sequences may be linked together to provide flexible linkers that may be used to conjugate a heterologous amino acid sequence to IL10Ra binding sdAbs disclosed herein. In some embodiments the linkers have the formula (GGGS)n (SEQ ID NO: 95), (GGGSG)n (SEQ ID NO: 96), or (GGSG)n (SEQ ID NO: 97), wherein n is an integer selected from 1, 2, 3, 4, 5, 6, 7, 8, 9 and 10.

Immunomodulatory Agents

In some embodiments, a IL10Ra binding molecule of the present disclosure comprises an immunomodulatory agent (immunoconjugates). Immunomodulatory agents that may conjugated to the hIL10Ra binding sdAb of the present disclosure include, but are not limited to, inactivated virus particles, inactivated bacterial toxins such as toxoid from diphtheria, tetanus, cholera, or leukotoxin molecules, inactivated bacteria and dendritic cells. Such immunoconjugates are useful in facilitating an immune response against the IL10Ra or cells expressing the IL10Ra.

Flag Tags

In one embodiment, the present disclosure provides a IL10Ra binding molecule comprising an antigenic tag, such as a FLAG sequence. FLAG sequences are recognized by biotinylated, highly specific, anti-FLAG antibodies, as described herein (see e.g., Blanar et al. (1992) Science 256:1014 and LeClair, et al. (1992) PNAS-USA 89:8145). In some embodiments, the IL10Ra binding sdAb polypeptide further comprises a C-terminal c-myc epitope tag.

Chelating Peptides

In one embodiment, the present disclosure provides a IL10Ra binding molecule comprising one or more transition metal chelating polypeptide sequences. The incorporation of such a transition metal chelating domain facilitates purification immobilized metal affinity chromatography (IMAC) as described in Smith, et al. U.S. Pat. No. 4,569,794 issued Feb. 11, 1986. Examples of transition metal chelating polypeptides useful in the practice of the present IL10Ra binding molecule are described in Smith, et al. supra and Dobeli, et al. U.S. Pat. No. 5,320,663 issued May 10, 1995, the entire teachings of which are hereby incorporated by reference. Particular transition metal chelating polypeptides useful in the practice of the present IL10Ra binding molecule are polypeptides comprising 3-6 contiguous histidine residues (SEQ ID NO: 98) such as a six-histidine (His)$_6$ (SEQ ID NO: 93) or eight histidine (His)$_8$ peptide (SEQ ID NO: 94) and are frequently referred to in the art as "His-tags." In addition to providing a purification "handle" for the recombinant proteins or to facilitate immobilization on SPR sensor chips, such the conjugation of the IL10Ra binding molecule to a chelating peptide facilitates the targeted delivery to IL10Ra expressing cells of transition metal ions as kinetically inert or kinetically labile complexes in substantial accordance with the teaching of Anderson, et al., (U.S. Pat. No. 5,439,829 issued Aug. 8, 1995 and Hale, J. E (1996) Analytical Biochemistry 231(1):46-49. The transition metal ion is a reporter molecule such as a fluorescent compound or radioactive agent, including as radiological imaging or therapeutic radiological agents.

Carrier Molecules

In some embodiments the IL10Ra binding sdAbs of the present disclosure may be conjugated to one or more carrier molecules. Carrier molecules are typically large, slowly metabolized macromolecules which provide for stabilization and/or extended duration of action in vivo to distinguish such molecules from conventional carrier molecules used in the preparation of pharmaceutical formulations as described below. Examples of in vivo carriers that may be incorporated into IL10Ra binding molecules, but are not limited to: proteins (including but not limited to human serum albumin); fatty acids (acylation); polysaccharides (including but not limited to (N- and O-linked) sugars, sepharose, agarose, cellulose, or cellulose); copolymers, acylation, or polysialylation, an polyethylene glycol (PEG) polymers.

Water Soluble Polymers

In some embodiments, the IL10Ra binding sdAb is conjugated to one or more water-soluble polymers. Examples of water soluble polymers useful in the practice of the present IL10Ra binding molecule include polyethylene glycol (PEG), poly-propylene glycol (PPG), polysaccharides (polyvinylpyrrolidone, copolymers of ethylene glycol and propylene glycol, poly(oxyethylated polyol), polyolefinic alcohol, polysaccharides, poly-alpha-hydroxy acid, polyvinyl alcohol (PVA), polyphosphazene, polyoxazolines (POZ), poly(N-acryloylmorpholine), or a combination thereof.

Polyethylene Glycol

In one embodiment, the carrier molecule is a polyethylene glycol ("PEG") polymer. Conjugation of PEG polymers to proteins (PEGylation) is a well-established method for the extension of serum half-life of biological agents. The PEGylated polypeptide may be further referred to as monopegylated, dipegylated, tripegylated (and so forth) to denote a polypeptide comprising one, two, three (or more) PEG moieties attached to the polypeptide, respectively. In some embodiments, the PEG may be covalently attached directly to the sdAb (e.g., through a lysine side chain, sulfhydryl group of a cysteine or N-terminal amine) or optionally employ a linker between the PEG and the sdAb. In some embodiments, a IL10Ra binding molecule comprises more than one PEG molecules each of which is attached to a different amino acid residue. In some embodiments, the sdAb may be modified by the incorporation of non-natural amino acids with non-naturally occurring amino acid side chains to facilitate site specific PEGylation. In other embodiments, cysteine residues may be substituted at one or more positions within the sdAb to facilitate site-specific PEGylation via the cysteine sulfhydryl side chain.

In some instances, the IL10Ra binding molecules of the present disclosure possess an N-terminal glutamine ("1Q") residue. N-terminal glutamine residues have been observed to spontaneously cyclyize to form pyroglutamate (pE) at or near physiological conditions. (See e.g., Liu, et al (2011) J. Biol. Chem. 286(13): 11211-11217). In some embodiments, the formation of pyroglutamate complicates N-terminal PEG conjugation particularly when aldehyde chemistry is used for N-terminal PEGylation. Consequently, when PEGylating the IL10Ra binding molecules of the present disclosure, particularly when aldehyde chemistry is to be employed, the IL10Ra binding molecules possessing an amino acid at position 1 (e.g., 1Q) are substituted at position 1 with an alternative amino acid or are deleted at position 1 (e.g., des-1Q). In some embodiments, the IL10Ra binding molecules of the present disclosure comprise an amino acid substitution selected from the group Q1E and Q1D.

PEGs suitable for conjugation to a polypeptide sequence are generally soluble in water at room temperature, and have the general formula $$R(O\text{-}CH_2\text{-}CH_2)_nO\text{—}R,$$

where R is hydrogen or a protective group such as an alkyl or an alkanol group, and where n is an integer from 1 to 1000. When R is a protective group, it generally has from 1 to 8 carbons. The PEG can be linear or branched. Branched PEG derivatives, "star-PEGs" and multi-armed PEGs are contemplated by the present disclosure.

A molecular weight of the PEG used in a IL10Ra binding molecule is not restricted to any particular range. The PEG component of a IL10Ra binding molecule can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about kDa, from about 10 kDa to about 20 kDa, from about 10 kDa to about 25 kDa or from about kDa to about 30 kDa. Linear or branched PEG molecules having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20,000 to about 50,000 daltons, alternatively about 30,000 to about 50,000 daltons, alternatively about 20,000 to about 40,000 daltons, alternatively about 30,000 to about 40,000 daltons. In one embodiment of the IL10Ra binding molecule, the PEG is a 40 kD branched PEG comprising two 20 kD arms.

The present disclosure also contemplates a IL10Ra binding molecule comprising more than one PEG moiety wherein the PEGs have different sizes values, and thus the various different PEGs are present in specific ratios. For example, in the preparation of a PEGylated IL10Ra binding molecule, some compositions comprise a mixture of mono-, di-, tri-, and quadra-PEGylated sdAb conjugates. In some compositions, the percentage of mono-PEGylated species is 18-25%, the percentage of di-PEGylated species is 50-66%, the percentage of tri-pegylated species is 12-16%, and the percentage of quadra-pegylated species up to 5%. Such complex compositions can be produced by reaction conditions and purification methods known in the art. Chromatography may be used to resolve conjugate fractions, and a fraction is then identified which contains the conjugate having, for example, the desired number of PEGs attached, purified free from unmodified protein sequences and from conjugates having other numbers of PEGs attached.

PEGylation most frequently occurs at the α-amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry.

Two widely used first generation activated monomethoxy PEGs (mPEGs) are succinimdyl carbonate PEG (SC-PEG; see, e.g., Zalipsky, et al. (1992) Biotehnol. Appl. Biochem 15:100-114) and benzotriazole carbonate PEG (BTC-PEG; see, e.g., Dolence, et al. U.S. Pat. No. 5,650,234), which react preferentially with lysine residues to form a carbamate linkage but are also known to react with histidine and tyrosine residues. Use of a PEG-aldehyde linker targets a single site on the N-terminus of a polypeptide through reductive amination.

The PEG can be bound to a IL10Ra binding molecule of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide.

In some embodiments, the PEGylation of the sdAb is facilitated by the incorporation of non-natural amino acids bearing unique side chains to facilitate site specific PEGylation. The incorporation of non-natural amino acids into polypeptides to provide functional moieties to achieve site specific PEGylation of such polypeptides is known in the art. See e.g., Ptacin, et al., PCT International Application No. PCT/US2018/045257 filed Aug. 3, 2018 and published Feb. 7, 2019 as International Publication Number WO 2019/028419A1.

The PEG moiety of the of a PEGylated IL10Ra binding moleculemay be linear or branched. Branched PEG derivatives, "star-PEGs" and multi-armed PEGs are contemplated by the present disclosure. Specific embodiments PEGs useful in the practice of the present disclosure include a 10 kDa linear PEG-aldehyde (e.g., Sunbright® ME-100AL, NOF America Corporation, One North Broadway, White Plains, N.Y. 10601 USA), 10 kDa linear PEG-NHS ester (e.g., Sunbright® ME-100CS, Sunbright® ME-100AS, Sunbright® ME-100GS, Sunbright® ME-100HS, NOF), a 20 kDa linear PEG-aldehyde (e.g., Sunbright® ME-200AL, NOF, a 20 kDa linear PEG-NHS ester (e.g., Sunbright® ME-200CS, Sunbright® ME-200AS, Sunbright® ME-200GS, Sunbright® ME-200HS, NOF), a 20 kDa 2-arm branched PEG-aldehyde the 20 kDA PEG-aldehyde comprising two 10 kDA linear PEG molecules (e.g., Sunbright® GL2-200AL3, NOF), a 20 kDa 2-arm branched PEG-NHS ester the 20 kDA PEG-NHS ester comprising two 10 kDA linear PEG molecules (e.g., Sunbright® GL2-200TS, Sunbright® GL200GS2, NOF), a 40 kDa 2-arm branched PEG-aldehyde the 40 kDA PEG-aldehyde comprising two 20 kDA linear PEG molecules (e.g., Sunbright® GL2-400AL3), a kDa 2-arm branched PEG-NHS ester the 40 kDA PEG-NHS ester comprising two 20 kDA linear PEG molecules (e.g., Sunbright® GL2-400AL3, Sunbright® GL2-400GS2, NOF), a linear 30 kDa PEG-aldehyde (e.g., Sunbright® ME-300AL) and a linear 30 kDa PEG-NHS ester.

Fc Fusions

In some embodiments, the carrier molecule is a Fc molecule or a monomeric subunit thereof. In some embodiments, the dimeric Fc molecule may be engineered to possess a "knob-into-hole modification." The knob-into-hole modification is more fully described in Ridgway, et al. (1996) Protein Engineering 9(7):617-621 and U.S. Pat. No. 5,731,168, issued Mar. 24, 1998, U.S. Pat. No. 7,642,228, issued Jan. 5, 2010, U.S. Pat. No. 7,695,936, issued Apr. 13, 2010, and U.S. Pat. No. 8,216,805, issued Jul. 10, 2012. The knob-into-hole modification refers to a modification at the interface between two immunoglobulin heavy chains in the CH3 domain, wherein: i) in a CH3 domain of a first heavy chain, an amino acid residue is replaced with an amino acid residue having a larger side chain (e.g., tyrosine or tryptophan) creating a projection from the surface ("knob") and ii) in the CH3 domain of a second heavy chain, an amino acid residue is replaced with an amino acid residue having a smaller side chain (e.g., alanine or threonine), thereby generating a cavity ("hole") within at interface in the second CH3 domain within which the protruding side chain of the first CH3 domain ("knob") is received by the cavity in the second CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. Furthermore, the Fc domains may be modified by the introduction of cysteine residues at positions S354 and Y349 which results in a stabilizing disulfide bridge between the two antibody heavy chains in the Fe region (Carter, et al. (2001) Immunol Methods 248, 7-15). The knob-into-hole format is used to facilitate the expression of a first polypeptide (e.g., an IL10Ra binding sdAb) on a first Fc monomer with a "knob" modification and a second polypeptide on the second Fc monomer possessing a "hole" modification to facilitate the expression of heterodimeric polypeptide conjugates.

Targeting Domains

In some embodiments, the IL10Ra binding molecule is provided as a component of a multivalent (e.g., bivalent) fusion protein with a polypeptide sequence ("targeting domain") to facilitate selective binding to particular cell type or tissue expressing a cell surface molecule that specifically binds to such targeting domain, optionally incorporating a linker between the IL10Ra binding sdAb sequence and the sequence of the targeting domain of the fusion protein.

In some embodiments of the IL10Ra binding molecule, the IL10Ra binding molecule may be targeted to a particular cell type cell by incorporation of a targeting domain into the structure of the IL10Ra binding molecules. As used herein, the term targeting domain refers to a moiety that specifically binds to a molecule expressed on the surface of a target cell. The targeting domain may be any moiety that specifically binds to one or more cell surface molecules (e.g., T cell receptor) expressed on the surface of a target cell. In some embodiments, the target cell is a T cell. In some embodiments, the target cell is a IL10Ra+ T cell.

In some embodiments, the targeting domain is a ligand for a receptor on the cell expressing the IL10Ra. In some embodiments, the targeting domain is a ligand for a receptor expressed on the surface of a T cell. In some embodiments, the ligand is a cytokine. In some embodiments, the cytokine includes but is not limited to the group consisting interleukins, interferons, and functional derivatives thereof. In some embodiments, the cytokine includes but is not limited to the group consisting IL2, IL3, IL4, IL7, IL9, IL12, IL15, IL18, IL21, IL22, IL23, IL27, IL28, IL34, and modified versions or fragments thereof that bind to their cognate ligand expressed on the surface of a T-cell. In some embodiments, the cytokine includes but is not limited to the group consisting of interferon alpha, interferon a2b, interferon gamma, or interferon lambda and modified versions or fragments thereof that bind to their cognate ligand expressed on the surface of a T-cell.

In another aspect, the present disclosure provides a multivalent binding molecule, the multivalent binding molecule comprising: (a) a IL10Ra binding molecule and (b) a second binding molecule that specifically binds to the extracellular domain of a second cell surface molecule, wherein the IL10Ra binding molecule and second binding molecule are operably linked, optionally through a chemical or polypeptide linker. In some embodiments, the IFNgR1 binding molecules of the present disclosure are useful in the preparation of the multivalent binding molecules described in Gonzalez, et al. PCT/US2018/021301 published as WO 2018/182935 A1 on Oct. 4, 2018. In accordance with the teaching of Gonzalez, the second binding molecule specifically binds to the extracellular domain of: (i) a component of cytokine receptor other than a receptor of which IL10Ra forms a signaling complex in response to a natural ligand (e.g., IL10) that activates the JAK/STAT pathway in the cell; (ii) a receptor tyrosine kinase; or (iii) a TNFR superfamily member. In some embodiments, the second surface molecule is a tyrosine kinase selected from EGFR, ErbB2, ErbB3, ErbB4, InsR, IGF1R, InsRR, PDGFRα, PDGFRβ, CSF1R/Fms, cKit, Flt-3/Flk2, VEGFR1, VEGFR2, VEGFR3, FGFR1, FGFR2, FGFR3, FGFR4, PTK7/CCK4, TrkA, TrkB, TrkC, Ror1, Ror2, MuSK, Met, Ron, Axl, Mer, Tyro3, Tie1, Tie2, EphA1-8, EphA10, EphB1-4, EphB6, Ret, Ryk, DDR1, DDR2, Ros, LMR1, LMR2, LMR3, ALK, LTK, SuRTK106/STYK1. In some embodiments, the second surface molecule is a TNFR superfamily member is selected from TNFR1 (TNFRSF1A), TNFR2 (TNFRSF1B; TNFRSF2), 41-BB (TNFRSF9); AITR (TNFRSF18); BCMA (TNFRSF17), CD27 (TNFRSF7), CD30 (TNFRSF8), CD40 (TNFRSF5), Death Receptor 1 (TNFRSF10C), Death Receptor-3 (TNFRSF25), Death Receptor 4 (TNFRSF10A), Death Receptor 5 (TNFRSF10B), Death Receptor-6 (TNFRSF21), Decoy Receptor-3 (TNFRSF6B), Decoy Receptor 2 (TNFRSF10D), EDAR, Fas (TNFRSF6), HVEM (TNFRSF14), LTBR (TNFRSF3), OX40 (TNFRSF4), RANK (TNFRSF11A), TACI (TNFRSF13B), Troy (TNFRSF19), XEDAR (TNFRSF27), Osteoprotegerin (TNFRSF11B), TWEAK receptor (TNFRSF12A), BAFF Receptor (TNFRSF13C), NGF receptor (TNFRSF16).

In some embodiments, the targeting domain is a polypeptide that specifically binds to a cell surface molecule associated with a tumor cell (e.g., a cognate ligand for a tumor cell receptor) selected from the group consisting of GD2, BCMA, CD19, CD33, CD38, CD70, GD2, IL3Ra2, CD19, mesothelin, Her2, EpCam, Mucl, ROR1, CD133, CEA, EGRFRVIII, PSCA, GPC3, Pan-ErbB and FAP.

101361 In some embodiments, the targeting domain of the IL10Ra binding molecule is an antibody (as defined hereinabove to include molecules such as VHHs, scFvs, etc.). Examples of antibodies that may incorporated as a targeting domain of a IL10Ra binding molecule include but are not limited to the group consisting of: anti-GD2 antibodies, anti-BCMA antibodies, anti-CD19 antibodies, anti-CD33 antibodies, anti-CD38 antibodies, anti-CD70 antibodies, anti-GD2 antibodies and IL3Ra2 antibodies, anti-CD19 antibodies, anti-mesothelin antibodies, anti-Her2 antibodies, anti-EpCam antibodies, anti-Mucl antibodies, anti-ROR1 antibodies, anti-CD133 antibodies, anti-CEA antibodies, anti-PSMA antibodies, anti-EGRFRVIII antibodies, anti-PSCA antibodies, anti-GPC3 antibodies, anti-Pan-ErbB antibodies, and anti-FAP antibodies.

The antibody or antigen-binding fragment thereof can also be linked to another antibody to form, e.g., a bispecific or a multispecific antibody Labels In some embodiments, IL10Ra binding molecules of the present disclosure comprise a label. In some embodiments, the label is incorporated to facilitate use as imaging agent, diagnostic agent, or for use in cell sorting procedures. The term labels includes but is not limited to fluorescent labels, a biologically active enzyme labels, a radioisotopes (e.g., a radioactive ions), a nuclear magnetic resonance active labels, a luminescent labels, or a magnetic compound. In one embodiment a IL10Ra binding sdAb (e.g., a IL10Ra binding VHH) molecule in stable association (e.g., covalent, coordinate covalent) with an imaging labels. The term imaging labels is used to describe any of a variety of compounds a signature that facilitates identification, tracing and/or localization of the IL10Ra binding sdAb (or its metabolites) using diagnostic procedures. Examples of imaging labels include, but are not limited to, fluorescent compounds, radioactive compounds, and compounds opaque to imaging methods (e.g., X-ray, ultrasound). Examples of radioactive compounds useful as imaging label include but are not limited to Technetium-99m ($^{99m}$Tc), Indium-111 ($^{111}$In), Iodine-131 ($^{131}$I), Iodine-123 ($^{123}$I), Iodine-125 ($^{125}$I), Gallium-67 ($^{67}$Ga), and Lutetium-177 ($^{177}$Lu), phosphorus ($^{32}$P), carbon ($^{14}$C), tritium ($^{3}$H), yttrium ($^{90}$Y), actinium ($^{225}$Ac), astatine ($^{211}$At), rhenium ($^{186}$Re), bismuth ($^{212}$Bi or $^{213}$Bi), and rhodium ($^{188}$Rh).

Therapeutic Agents

In some embodiments, IL10Ra binding molecules of the present disclosure comprise a therapeutic agent. Examples of therapeutic agents include therapeutic small molecule (e.g., chemotherapeutic agents) or biologic therapeutic agents including antibodies, cytoxic or cytostatic compounds, a radioisotope, molecules of plant, fungal, or bacterial origin, or biological proteins (e.g., protein toxins) or particles (e.g., nano-particles or recombinant viral particles, e.g., via a viral coat protein), therapeutic antibodies, chemotherapeutic agents, as described more fully herein.

In some embodiments, the therapeutic agent which may be incorporated into the IL10Ra binding molecules of the present disclosure is short-range radiation emitters, including, for example, short-range, high-energy a-emitters. Examples of such radioisotope include an alpha-emitter, a beta-emitter, a gamma-emitter or a beta/gamma emitter. Radioisotopes useful as therapeutic agents include yttrium 90 ($^{90}$Y), lutetium-177 ($^{177}$Lu), actinium-225 ($^{225}$Ac), astatine-211 ($^{186}$At), rhenium-186 ($^{186}$Re), bismuth-212 ($^{212}$Bi), bismuth-213 ($^{213}$Bi), and rhodium-188 ($^{188}$Rh).

In some embodiments, the IL10Ra binding molecules comprises a cytotoxic agent (or derivative thereof), such maytansinol or the DM1 maytansinoid), a taxane, or a calicheamicin, pseudomonas exotoxin A, deBouganin, ricin toxin, diphtheria toxin, an amatoxin, such as a-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof).

Multispecific Binding Format

The sdAbs can be combined to provide multispecific targeting and selection including in combination with bi-specific and tri-specific constructs which bind to one or more cell surface antigens.

Synthesis of IL10Ra Binding Molecules:

In some embodiments, the IL10Ra binding molecules of the present disclosure are polypeptides. However, in some embodiments, only a portion of the IL10Ra binding molecule is a polypeptide, for example where the IL10Ra binding molecule comprises a non-peptidyl domain (e.g., a PEG anti-IL10Ra sdAb conjugate, a radionucleotide anti-IL10Ra sdAb conjugate, or a small molecule anti-IL10Ra binding sdAb conjugate). The following provides guidance to enable the solid phase and recombinant synthesis of the polypeptide portions (domains) of IL10Ra binding molecules of the present disclosure. In those embodiments where only a portion of the IL10Ra binding molecule is a polypeptide, it will be understood that the peptidyl domain(s) of the IL10Ra binding molecule are an intermediate in the process which may undergo further processing to complete the synthesis of the desired IL10Ra binding molecules. The polypeptide domains of IL10Ra binding molecules may be produced by conventional methodology for the construction of polypeptides including recombinant or solid phase syntheses as described in more detail below.

Chemical Synthesis

In addition to generating mutant polypeptides via expression of nucleic acid molecules that have been altered by recombinant molecular biological techniques, polypeptide domains of IL10Ra binding molecules can be chemically synthesized. Chemically synthesized polypeptides are routinely generated by those of skill in the art. Chemical synthesis includes direct synthesis of a peptide by chemical means of the polypeptide domains of IL10Ra binding molecules exhibiting the properties described. This method can incorporate both natural and unnatural amino acids at desired positions that facilitate linkage of particular molecules (e.g., PEG).

In some embodiments, the polypeptide domains of IL10Ra binding molecules of the present disclosure may be prepared by chemical synthesis. The chemical synthesis of the polypeptide domains of IL10Ra binding molecules may proceed via liquid-phase or solid-phase. Solid-phase peptide synthesis (SPPS) allows the incorporation of unnatural amino acids and/or peptide/protein backbone modification. Various forms of SPPS are available for synthesizing the polypeptide domains of IL10Ra binding molecules of the present disclosure are known in the art (e.g., Ganesan A. (2006) Mini Rev. Med. Chem. 6:3-10; and Camarero J. A. et al., (2005) Protein Pept Lett. 12:723-8). In the course of chemical synthesis, the alpha functions and any reactive side chains may protected with acid-labile or base-labile groups that are stable under the conditions for linking amide bonds but can readily be cleaved without impairing the peptide chain that has formed.

In the solid phase synthesis, either the N-terminal or C-terminal amino acid may be coupled to a suitable support material. Suitable support materials are those which are inert towards the reagents and reaction conditions for the stepwise condensation and cleavage reactions of the synthesis process and which do not dissolve in the reaction media being used. Examples of commercially available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers; and the like. The successive coupling of the protected amino acids can be carried out according to conventional methods in peptide synthesis, typically in an automated peptide synthesizer.

At the end of the solid phase synthesis, the peptide is cleaved from the support material while simultaneously cleaving the side chain protecting groups. The peptide obtained can be purified by various chromatographic methods including but not limited to hydrophobic adsorption chromatography, ion exchange chromatography, distribution chromatography, high pressure liquid chromatography (HPLC) and reverse-phase HPLC.

Recombinant Production

Alternatively, polypeptide domains of IL10Ra binding molecules of the present disclosure may be produced by recombinant DNA technology. In the typical practice of recombinant production of polypeptides, a nucleic acid sequence encoding the desired polypeptide is incorporated into an expression vector suitable for the host cell in which expression will be accomplish, the nucleic acid sequence being operably linked to one or more expression control sequences encoding by the vector and functional in the target host cell. The recombinant protein may be recovered through disruption of the host cell or from the cell medium if a secretion leader sequence (signal peptide) is incorporated into the polypeptide. The recombinant protein may be purified and concentrated for further use including incorporation.

Synthesis of Nucleic Acid Sequences Encoding the IL10Ra Binding Molecule

In some embodiments, the polypeptide domains of IL10Ra binding molecule is produced by recombinant methods using a nucleic acid sequence encoding the polypeptide domains of IL10Ra binding molecule (or fusion protein comprising the polypeptide domains of IL10Ra binding molecule). The nucleic acid sequence encoding the desired polypeptide domains of IL10Ra binding molecule can be synthesized by chemical means using an oligonucleotide synthesizer.

The nucleic acid molecules are not limited to sequences that encode polypeptides; some or all of the non-coding sequences that lie upstream or downstream from a coding sequence (e.g., the coding sequence of the polypeptide domains of IL10Ra binding molecule) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The nucleic acid molecules encoding the polypeptide domains of IL10Ra binding molecule (and fusions thereof) may contain naturally occurring sequences or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

Nucleic acid sequences encoding the polypeptide domains of the IL10Ra binding molecule may be obtained from various commercial sources that provide custom synthesis of nucleic acid sequences. Amino acid sequence variants of the HUMAN IL10Ra binding molecules of the present disclosure are prepared by introducing appropriate nucleotide changes into the coding sequence based on the genetic code which is well known in the art. Such variants represent insertions, substitutions, and/or specified deletions of, residues as noted. Any combination of insertion, substitution, and/or specified deletion can be made to arrive at the final construct, provided that the final construct possesses the desired biological activity as defined herein.

Methods for constructing a DNA sequence encoding the polypeptide domains of IL10Ra binding molecule and expressing those sequences in a suitably transformed host include, but are not limited to, using a PCR-assisted mutagenesis technique. Mutations that consist of deletions or additions of amino acid residues to polypeptide domains of IL10Ra binding molecule can also be made with standard recombinant techniques. In the event of a deletion or addition, the nucleic acid molecule encoding polypeptide domains of IL10Ra binding molecule is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

A polypeptide domain of IL10Ra binding molecules of the present disclosure may be produced recombinantly not only directly, but also as a fusion polypeptide with a heterologous polypeptide, e.g., a signal sequence or other polypeptide having a specific cleavage site at the N-terminus or C-terminus of the mature IL10Ra binding molecule. In general, the signal sequence may be a component of the vector, or it may be a part of the coding sequence that is inserted into the vector. The heterologous signal sequence selected preferably is one that is recognized and processed (i.e., cleaved by a signal peptidase) by the host cell. In some embodiments, the signal sequence is the signal sequence that is natively associated with the IL10Ra binding molecule (i.e. the human IL10Ra signal sequence). The inclusion of a signal sequence depends on whether it is desired to secrete the IL10Ra binding molecule from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild type IL-2 signal sequence be used. Alternatively, heterologous mammalian signal sequences may be suitable, such as signal sequences from secreted polypeptides of the same or related species, as well as viral secretory leaders, for example, the herpes simplex gD signal. When the recombinant host cell is a yeast cell such as Saccharomyces cerevisiae, the alpha mating factor secretion signal sequence may be employed to achieve extracellular secretion of the IL10Ra binding molecule into the culture medium as described in Singh, U.S. Pat. No. 7,198,919 B1.

In the event the polypeptide domain of IL10Ra binding molecules to be expressed is to be expressed as a chimera (e.g., a fusion protein comprising a IL10Ra binding molecule and a heterologous polypeptide sequence), the chimeric protein can be encoded by a hybrid nucleic acid molecule comprising a first sequence that encodes all or part of the polypeptide domains of IL10Ra binding molecule and a second sequence that encodes all or part of the heterologous polypeptide. For example, polypeptide domains of IL10Ra binding molecules described herein may be fused to a hexa-histidine tag (SEQ ID NO: 93) to facilitate purification of bacterially expressed protein, or to a hemagglutinin tag to facilitate purification of protein expressed in eukaryotic cells. By first and second, it should not be understood as limiting to the orientation of the elements of the fusion protein and a heterologous polypeptide can be linked at either the N-terminus and/or C-terminus of the polypeptide domains of IL10Ra binding molecule. For example, the N-terminus may be linked to a targeting domain and the C-terminus linked to a hexa-histidine tag (SEQ ID NO: 93) purification handle.

The complete amino acid sequence of the polypeptide domain of IL10Ra binding molecule (or fusion/chimera) to be expressed can be used to construct a back-translated gene. A DNA oligomer containing a nucleotide sequence coding for the polypeptide domain of IL10Ra binding molecules can be synthesized. For example, several small oligonucleotides coding for portions of the desired polypeptide can be synthesized and then ligated. The individual oligonucleotides typically contain 5' or 3' overhangs for complementary assembly.

In some embodiments, the nucleic acid sequence encoding the polypeptide domain of the IL10Ra binding molecule may be "codon optimized" to facilitate expression in a particular host cell type. Techniques for codon optimization in a wide variety of expression systems, including mammalian, yeast and bacterial host cells, are well known in the and there are online tools to provide for a codon optimized sequences for expression in a variety of host cell types. See e.g., Hawash, et al., (2017) 9:46-53 and Mauro and Chappell in *Recombinant Protein Expression in Mammalian Cells: Methods and Protocols*, edited by David Hacker (Human Press New York). Additionally, there are a variety of web based on-line software packages that are freely available to assist in the preparation of codon optimized nucleic acid sequences.

In some embodiments, the nucleic acid sequence encoding the polypeptide domain of the IL10Ra binding molecule is a DNA sequence provided in Table 2.

Expression Vectors

Once assembled (by synthesis, site-directed mutagenesis or another method), the nucleic acid sequence encoding polypeptide domains of IL10Ra binding molecule will be inserted into an expression vector. A variety of expression vectors for uses in various host cells are available and are typically selected based on the host cell for expression. An expression vector typically includes, but is not limited to, one or more of the following: an origin of replication, one or more marker genes, an enhancer element, a promoter, and a transcription termination sequence. Vectors include viral vectors, plasmid vectors, integrating vectors, and the like. Plasmids are examples of non-viral vectors. To facilitate efficient expression of the recombinant polypeptide, the nucleic acid sequence encoding the polypeptide sequence to be expressed is operably linked to transcriptional and translational regulatory control sequences that are functional in the chosen expression host.

Expression vectors typically contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Expression vectors for polypeptide domain of IL10Ra binding molecules of the present disclosure contain a regulatory sequence that is recognized by the host organism and is operably linked to nucleic acid sequence encoding the polypeptide domains of IL10Ra binding molecule. The terms "regulatory control sequence," "regulatory sequence" or "expression control sequence" are used interchangeably herein to refer to promoters, enhancers, and other expression control elements (e.g., polyadenylation signals). See, for example, Goeddel (1990) in Gene Expression Technology: Methods in Enzymology 185 (Academic Press, San Diego Calif. USA Regulatory sequences include those that direct constitute expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. In selecting an expression control sequence, a variety of factors understood by one of skill in the art are to be considered. These include, for example, the relative strength of the sequence, its controllability, and its compatibility with the actual DNA sequence encoding the subject IL10Ra binding molecule, particularly as regards potential secondary structures.

In some embodiments, the regulatory sequence is a promoter, which is selected based on, for example, the cell type in which expression is sought. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

Transcription from vectors in mammalian host cells may be controlled, for example, by promoters obtained from the genomes of viruses such as polyoma virus, fowlpox virus, adenovirus (such as human adenovirus serotype 5), bovine papilloma virus, avian sarcoma virus, cytomegalovirus, a retrovirus (such as murine stem cell virus), hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence but is preferably located at a site 5' from the promoter. Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Additional examples of marker or reporter genes include beta-lactamase, chloramphenicol acetyltransferase (CAT), adenosine deaminase (ADA), dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). Those of skill in the art can readily determine whether a given regulatory element or selectable marker is suitable for use in a particular experimental context. Proper assembly of the expression vector can be confirmed by nucleotide sequencing, restriction mapping, and expression of a biologically active polypeptide in a suitable host.

Host Cells

The present disclosure further provides prokaryotic or eukaryotic cells that contain and express a nucleic acid molecule that encodes a polypeptide domains of IL10Ra binding molecule. A cell of the present disclosure is a transfected cell, i.e., a cell into which a nucleic acid molecule, for example a nucleic acid molecule encoding a polypeptide domains of IL10Ra binding molecule, has been introduced by means of recombinant DNA techniques. The progeny of such a cell are also considered within the scope of the present disclosure.

Host cells are typically selected in accordance with their compatibility with the chosen expression vector, the toxicity of the product coded for by the DNA sequences of this IL10Ra binding molecule, their secretion characteristics, their ability to fold the polypeptides correctly, their fermentation or culture requirements, and the ease of purification of the products coded for by the DNA sequences. Suitable host cells for cloning or expressing the DNA in the vectors herein are the prokaryote, yeast, or higher eukaryote cells.

In some embodiments the recombinant polypeptide domains of IL10Ra binding molecule or biologically active variants thereof can also be made in eukaryotes, such as yeast or human cells. Suitable eukaryotic host cells include insect cells (examples of Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast S. cerevisiae include pYepSecl (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) Nature 329:840) and pMT2PC (Kaufman et al. (1987) EMBO J. 6:187:195)).

Examples of useful mammalian host cell lines are mouse L cells (L-M[TK-], ATCC #CRL-2648), monkey kidney CV1 line transformed by SV40 (COS-7, ATCC CRL 1651); human embryonic kidney line (HEK293 or HEK293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2). In mammalian cells, the expression vector's control functions are often provided by viral regulatory elements. For example, commonly used promoters are derived from polyoma, Adenovirus 2, cytomegalovirus, and Simian Virus 40.

The polypeptide domains of IL10Ra binding molecule can be produced in a prokaryotic host, such as the bacterium E. coli, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

In some embodiments, the recombinant polypeptide domains of IL10Ra binding molecule may be glycosylated or unglycosylated depending on the host organism used to produce the IL10Ra binding molecule. If bacteria are chosen as the host then the polypeptide domains of IL10Ra binding molecule produced will be aglycosylated. Eukaryotic cells, on the other hand, will glycosylate the recombinant polypeptide domains of IL10Ra binding molecule.

For other additional expression systems for both prokaryotic and eukaryotic cells, see Chapters 16 and 17 of Sambrook et al. (1989) Molecular Cloning: A Laboratory Manual (2nd ed., Cold Spring Harbor Laboratory Press, Plainview, N.Y.). See, Goeddel (1990) in Gene Expression Technology: Methods in Enzymology 185 (Academic Press, San Diego, Calif.).

Transfection

The expression constructs of the can be introduced into host cells to thereby produce the recombinant polypeptide domains of IL10Ra binding molecule disclosed herein or to produce biologically active muteins thereof. Vector DNA can be introduced into prokaryotic or eukaryotic cells via conventional transformation or transfection techniques. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other standard molecular biology laboratory manuals.

In order to facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, and magnetic fields (electroporation).

Cell Culture

Cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression and will be apparent to the ordinarily skilled artisan.

Recovery of Recombinant Proteins

Recombinantly-produced IL10Ra binding polypeptides can be recovered from the culture medium as a secreted polypeptide if a secretion leader sequence is employed. Alternatively, the IL10Ra binding polypeptides can also be recovered from host cell lysates. A protease inhibitor, such as phenyl methyl sulfonyl fluoride (PMSF) may be employed during the recovery phase from cell lysates to inhibit proteolytic degradation during purification, and antibiotics may be included to prevent the growth of adventitious contaminants.

Purification

Various purification steps are known in the art and find use, e.g., affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural specific binding of one molecular species to separate and purify a second species from a mixture. Antibodies are commonly used in affinity chromatography. Size selection steps may also be used, e.g., gel filtration chromatography (also known as size-exclusion chromatography or molecular sieve chromatography) is used to separate proteins according to their size. In gel filtration, a protein solution is passed through a column that is packed with semipermeable porous resin. The semipermeable resin has a range of pore sizes that determines the size of proteins that can be separated with the column.

The recombinant polypeptide domains of IL10Ra binding molecule produced by the transformed host can be purified according to any suitable method. IL10Ra binding molecules can be isolated from inclusion bodies generated in *E. coli*, or from conditioned medium from either mammalian or yeast cultures producing a given IL10Ra binding molecule sing cation exchange, gel filtration, and or reverse phase liquid chromatography.

The substantially purified forms of the recombinant polypeptides can be used, e.g., as therapeutic agents, as described herein.

The biological activity of the recombinant polypeptide domains of IL10Ra binding molecule produced in accordance with the foregoing can be confirmed by a IL10Ra binding using procedures well known in the art including but not limited to competition ELISA, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET) and surface plasmon resonance assays (see, e.g., Drescher et al., Methods Mol Biol 493:323-343 (2009) with instrumentation commercially available from GE Healthcare Bio-Sciences such as the Biacore 8+, Biacore S200, Biacore T200 (GE Healthcare Bio-Sciences, 100 Results Way, Marlborough Mass. 01752)); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays).

Methods of Use

Inhibition of IL10Ra Receptor Activity

In one embodiment, the present disclosure provides a method of modulating the activity of cells expressing the IL10Ra by the administration of a IL10Ra binding molecule to a subject in an amount sufficient to interfere with the activity of receptors comprising the of IL10Ra. The present disclosure further provides a method of modulating the activity of cells expressing the IL10Ra in a mixed population of cells comprising contacting said population of cells, in vivo and/or ex vivo, with a IL10Ra binding molecule or complex of the present disclosure to in an amount sufficient to interfere with the activity of receptors comprising the IL10Ra.

Infectious Diseases

In some embodiments, the compositions of the present disclosure are useful as inhibitors of the IL10 receptor, in particular—via targeting of the IL10Ra subunit to downregulate the immunosuppressive effects of endogenous IL-10. The therapeutic and/or prophylactic activity of IL10R antagonists (e.g. IL10Ra binding molecules) are well established in the scientific, literature. For example, Von Herrath, et al (U.S. Pat. No. 7,553,932 issued Jun. 30, 2009) disclose the use of IL10 receptor antagonist antibodies for the treatment of chronic acute infections, in particular chronic (persistent) or acute viral infections. Ejrnaes, et al. report on the use of anti-IL-10R antibodies as demonstrating effectiveness in the LCMV model of persistent viral infection. Ejrnaes, et al. (2006) J Exp Med 203(10:24.61-2472. Kato, et al (U.S. Pat. No. 8,420,784 issued Apr. 16, 2011) describe IL10Ra inhibitor antibodies are useful in the treatment and prophylaxis of pathogenic infections. Brooks, et al (J. Exp. Med. (2008) 205(3)3:533-541; Nature Medicine (2001) 1200:1301-1309) describe that IL10 receptor antagonists are useful in T-cell recovery and prevention of viral persistence and that blocking the IL-10 activity enhances clearance of persistent viral infections.

In some embodiments, the compositions of the present disclosure may be administered in combination with one or more additional antiviral agents for the treatment of viral infections selected from, but not limited. to, HIV, hepatitis C virus, hepatitis. B virus, herpes virus (HSV) types 1 and 2, Varicella-Zoster virus (VZV), Epstein-Barr Virus (EBV) cytomegalovirus (CMV) and measles. in some embodiments, the compositions of the present disclosure may be administered in in combination with one or more of antiviral agents selected from vaccines hepatitis C virus, hepatitis B virus, herpes virus (HSV) types 1 and 2, Varicella-Zoster virus (VZV), Epstein-Barr Virus (EBV) cytomegalovirus (CMV) and measles acyclovir, ganciclovir, zidovudine (AZT), interferon-a2b and interferon-a.

In some embodiments, the compositions of the present, disclosure may be used, alone or in combination with one or more supplementary antibiotic agents, in hie treatment of bacterial infectious disease. Examples of infectious diseases amenable to treatment with RAO inhibitors include but are not limited to listeriosis *Listeria monocytogenes*) (see, e.g., Silva and Appleberg (2001) Antimicrobial Agents and Chemotherapy 45(4):1312-1314).

Autoimmune and Inflammatory Diseases

In one embodiment the present disclosure provides a method of treating a T cell mediated autoimmune disease, the method comprising the administration of a IL10Ra binding molecule to a subject in an amount effective to inhibit a T-cell mediated immune response. IL10Ra binding molecules of the present disclosure specifically bind to the ECD of the IL10Ra, either alone or associated with other molecules, and are useful in modulating the function of the cells expressing IL10Ra and are useful in the treatment or prevention of diseases, disorders or conditions associated with inflammation or autoimmunity where immunological memory is involved in the cause, maintenance or exacerbation of the disease, disorder or condition. High serum levels of IL10 are associated with multiple autoimmune diseases including to not limited to systemic lupus erythematosus (SLE) patients, rheumatoid arthritis patients, in the serum of systemic sclerosis, Kawasaki disease, an ulcerative colitis, Sjogren's syndrome, Grave's disease, myasthenia gravis, psoriasis and autoimmune lymphoproliferative syndrome (ALPS). The compositions of the present disclosure as competitive inhibitors IL10 and blockade of the IL-10 receptor are useful in the treatment of autoimmune disease.

Disorders amenable to treatment with an IL10Ra binding molecule (including pharmaceutically acceptable formulations comprising an IL10Ra binding molecules and/or the nucleic acid molecules that encode them including recombinant viruses encoding such an IL10Ra binding molecules) of the present disclosure include inflammatory or autoimmune diseases including but not limited to, organ rejection, graft versus host disease, autoimmune thyroid disease, multiple sclerosis, allergy, asthma, neurodegenerative diseases including Alzheimer's disease, systemic lupus erythramatosis (SLE), autoinflammatory diseases, inflammatory bowel disease (IBD), Crohn's disease, diabetes including Type 1 or type 2 diabetes, inflammation, autoimmune disease, atopic diseases, paraneoplastic autoimmune diseases, cartilage inflammation, arthritis, rheumatoid arthritis, juvenile arthritis, juvenile rheumatoid arthritis, juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome (Seronegativity Enthesopathy Arthropathy Syndrome), juvenile dermatomyositis, juvenile psoriatic arthritis, juvenile scleroderma, juvenile systemic lupus erythematosus, juvenile vasculitis, pauciarticular rheumatoidarthritis, polyarticular rheumatoidarthritis, systemic onset rheumatoidarthritis, ankylosing spondylitis, enteropathic arthritis, reactive arthritis, Reiter's syndrome, SEA Syndrome (Seronegativity, Enthesopathy, Arthropathy Syndrome).

Other examples of proliferative and/or differentiative disorders amenable to treatment with IL10Ra binding molecules (including pharmaceutically acceptable formulations comprising IL10Ra binding molecules and/or the nucleic acid molecules that encode them including recombinant viruses encoding such IL10Ra binding molecules) of the present disclosure include, but are not limited to, skin disorders. The skin disorder may involve the aberrant activity of a cell or a group of cells or layers in the dermal, epidermal, or hypodermal layer, or an abnormality in the dermal-epidermal junction. For example, the skin disorder may involve aberrant activity of keratinocytes (e.g., hyperproliferative basal and immediately suprabasal keratinocytes), melanocytes, Langerhans cells, Merkel cells, immune cell, and other cells found in one or more of the epidermal layers, e.g., the stratum basale (stratum germinativum), stratum *spinosum*, stratum *granulosum*, stratum lucidum or stratum corneum. In other embodiments, the disorder may involve aberrant activity of a dermal cell, for example, a dermal endothelial, fibroblast, immune cell (e.g., mast cell or macrophage) found in a dermal layer, for example, the papillary layer or the reticular layer.

In Examples of inflammatory or autoimmune skin disorders include psoriasis, psoriatic arthritis, dermatitis (eczema), for example, exfoliative dermatitis or atopic dermatitis, *pityriasis rubra* pilaris, *pityriasis* rosacea, parapsoriasis, *pityriasis* lichenoiders, lichen planus, lichen *nitidus*, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as seborrheic dermatitis and solar dermatitis; keratoses such as seborrheic keratosis, senile keratosis, actinic keratosis, photo-induced keratosis, and keratosis follicularis; acne vulgaris; keloids and prophylaxis against keloid formation; nevi; warts including verruca, condyloma or condyloma *acuminatum*, and human papilloma viral (HPV) infections such as venereal warts; leukoplakia; lichen planus; and keratitis. The skin disorder can be dermatitis, e.g., atopic dermatitis or allergic dermatitis, or psoriasis.

In The compositions of the present disclosure (including pharmaceutically acceptable formulations comprising IL10Ra binding molecules and/or the nucleic acid molecules that encode them including recombinant viruses encoding such IL10Ra binding molecules) can also be administered to a patient who is suffering from (or may suffer from) psoriasis or psoriatic disorders. The term "psoriasis" is intended to have its medical meaning, namely, a disease which afflicts primarily the skin and produces raised, thickened, scaling, nonscarring lesions. The lesions are usually sharply demarcated erythematous papules covered with overlapping shiny scales. The scales are typically silvery or slightly opalescent. Involvement of the nails frequently occurs resulting in pitting, separation of the nail, thickening and discoloration. Psoriasis is sometimes associated with arthritis, and it may be crippling. Hyperproliferation of keratinocytes is a key feature of psoriatic epidermal hyperplasia along with epidermal inflammation and reduced differentiation of keratinocytes. Multiple mechanisms have been invoked to explain the keratinocyte hyperproliferation that characterizes psoriasis. Disordered cellular immunity has also been implicated in the pathogenesis of psoriasis. Examples of psoriatic disorders include chronic stationary psoriasis, plaque psoriasis, moderate to severe plaque psoriasis, psoriasis vulgaris, eruptive psoriasis, psoriatic erythroderma, generalized pustular psoriasis, annular pustular psoriasis, or localized pustular psoriasis.

Combination with Supplementary Therapeutic Agents

The present disclosure provides for the use of the IL10Ra binding molecules of the present disclosure in combination with one or more additional active agents ("supplementary agents"). Such further combinations are referred to interchangeably as "supplementary combinations" or "supplementary combination therapy" and those therapeutic agents that are used in combination with IL10Ra binding molecules of the present disclosure are referred to as "supplementary agents." As used herein, the term "supplementary agents" includes agents that can be administered or introduced separately, for example, formulated separately for separate administration (e.g., as may be provided in a kit) and/or therapies that can be administered or introduced in combination with the IL10Ra binding molecules.

As used herein, the term "in combination with" when used in reference to the administration of multiple agents to a subject refers to the administration of a first agent at least one additional (i.e. second, third, fourth, fifth, etc.) agent to a subject. For purposes of the present invention, one agent (e.g., IL10Ra binding molecule) is considered to be administered in combination with a second agent (e.g., a modulator of an immune checkpoint pathway) if the biological effect resulting from the administration of the first agent persists in the subject at the time of administration of the second agent such that the therapeutic effects of the first agent and second agent overlap. For example, the PD1 immune checkpoint inhibitors (e.g., nivolumab or pembrolizumab) are typically administered by IV infusion every two weeks or every three weeks while the IL10Ra binding molecules of the present disclosure are typically administered more frequently, e.g., daily, BID, or weekly. However, the administration of the first agent (e.g., pembrolizumab) provides a therapeutic effect over an extended time and the administration of the second agent (e.g., an IL10Ra binding molecule) provides its therapeutic effect while the therapeutic effect of the first agent remains ongoing such that the second agent is considered to be administered in combination with the first agent, even though the first agent may have been administered at a point in time significantly distant (e.g., days or weeks) from the time of administration of the second agent. In one embodiment, one agent is considered to be administered in combination with a second agent if the first and second agents are administered simultaneously (within 30 minutes of each other), contemporaneously or sequentially. In some embodiments, a first agent is deemed to be administered "contemporaneously" with a second agent if first and second agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a second agent are co-formulated in single pharmaceutically acceptable formulation and the co-formulation is administered to a subject. In certain embodiments, the IL10Ra binding molecule and the supplementary agent(s) are administered or applied sequentially, e.g., where one agent is administered prior to one or more other agents.

In other embodiments, the IL10Ra binding molecule and the supplementary agent(s) are administered simultaneously, e.g., where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

Supplemental Agents Useful in the Treatment of Inflammatory or Autoimmune Disorders In In some embodiments, the method further comprises administering of the IL10Ra binding molecule of the present disclosure in combination with one or more supplementary agents selected from the group consisting of a corticosteroid, a Janus kinase inhibitor, a calcineurin inhibitor, a mTor inhibitor, an IMDH inhibitor, a biologic, a vaccine, and a therapeutic antibody. In certain embodiments, the therapeutic antibody is an antibody that binds a protein selected from the group consisting of BLyS, CD11a, CD20, CD25, CD3, CD52, IgEIL12/IL23, IL17a, IL1ß, IL4Rα, IL5, IL6R, integrin-α4β7, RANKL, TNFα, VEGF-A, and VLA-4.

In In some embodiments, the supplementary agent is one or more agents selected from the group consisting of corticosteroids (including but not limited to prednisone, budesonide, prednilisone), Janus kinase inhibitors (including but not limited to tofacitinib (Xeljanz®), calcineurin inhibitors (including but not limited to cyclosporine and tacrolimus), mTor inhibitors (including but not limited to sirolimus and everolimus), IMDH inhibitors (including but not limited to azathioprine, leflunomide and mycophenolate), biologics such as abatcept (Orencia®) or etanercept (Enbrel®), and therapeutic antibodies.

In Examples of therapeutic antibodies that may be administered as supplementary agents in combination with the IL10Ra binding molecules of the present disclosure in the treatment of autoimmune disease include but are not limited to anti-CD25 antibodies (e.g. daclizumab and basiliximab), anti-VLA-4 antibodies (e.g. natalizumab), anti-CD52 antibodies (e.g. alemtuzumab), anti-CD20 antibodies (e.g. rituximab, ocrelizumab), anti-TNF antibodies (e.g. infliximab, and adalimumab), anti-IL6R antibodies (e.g. tocilizumab), anti-TNFα antibodies (e.g. adalimumab (Humira®), golimumab, and infliximab), anti-integrin-α4β7 antibodies (e.g. vedolizumab), anti-IL17a antibodies (e.g. brodalumab or secukinumab), anti-IL4Rα antibodies (e.g. dupilumab), anti-RANKL antibodies, IL6R antibodies, anti-IL1ß antibodies (e.g. canakinumab), anti-CD11a antibodies (e.g. efalizumab), anti-CD3 antibodies (e.g. muramonab), anti-IL5 antibodies (e.g. mepolizumab, reslizumab), anti-BLyS antibodies (e.g. belimumab); and anti-IL12/IL23 antibodies (e.g ustekinumab).

Many therapeutic antibodies have been approved for clinical use against autoimmune disease. Examples of antibodies approved by the United States Food and Drug Administration (FDA) for use in the treatment of autoimmune diseases in a subject suffering therefrom that may be administered as supplementary agents in combination with the IL10Ra binding molecules of the present disclosure (and optionally additional supplementary agents) for the treatment of the indicated autoimmune disease include atezolizumab, olaratumab, ixekizumab, trastuzumab, infliximab, rituximab, edrecolomab, daratumumab, elotuzumab, necitumumab, dinutuximab, nivolumab, blinatumomab, pembrolizumab, pertuzumab, brentuximab vedotin, ipilimumab, ofatumumab, certolizumab pegol, catumaxomab, panitumumab, bevacizumab, ramucirumab, siltuximab, enfortumab vedotin, polatuzumab vedotin, [fam]-trastuzumab deruxtecan, cemiplimab, moxetumomab pasudotox, mogamuizumab, tildrakizumab, ibalizumab, durvalumab, inotuzumab, ozogamicin, avelumab, obinutuzumab, ado-trastuzumab emtansine, cetuximab, tositumomab-I131, ibritumomab tiuxetan, gemtuzumab, and ozogamicin. The foregoing antibodies useful as supplementary agents in the practice of the methods of the present disclosure may be administered alone or in the form of any antibody drug conjugate (ADC) comprising the antibody, linker, and one or more drugs (e.g. 1, 2, 3, 4, 5, 6, 7, or 8 drugs) or in modified form (e.g. PEGylated).

Treatment of Neoplastic Disease

The present disclosure provides methods of use of IL10Ra binding molecules in the treatment of subjects suffering from a neoplastic disease disorder or condition by the administration of a therapeutically effective amount of a IL10Ra binding molecule (or nucleic acid encoding a IL10Ra binding molecule including recombinant vectors encoding IL10Ra binding molecules, and eucaryotic and procaryotic cells modified to express a IL10Ra binding molecule) as described herein.

Neoplasms Amenable to Treatment:

The compositions and methods of the present disclosure are useful in the treatment of subject suffering from a neoplastic disease characterized by the presence neoplasms, including benign and malignant neoplasms, and neoplastic disease.

Examples of benign neoplasms amenable to treatment using the compositions and methods of the present disclosure include but are not limited to adenomas, fibromas, hemangiomas, and lipomas. Examples of pre-malignant neoplasms amenable to treatment using the compositions and methods of the present disclosure include but are not limited to hyperplasia, atypia, metaplasia, and dysplasia. Examples of malignant neoplasms amenable to treatment using the compositions and methods of the present disclosure include but are not limited to carcinomas (cancers arising from epithelial tissues such as the skin or tissues that line internal organs), leukemias, lymphomas, and sarcomas typically derived from bone fat, muscle, blood vessels or connective tissues). Also included in the term neoplasms are viral induced neoplasms such as warts and EBV induced disease (i.e., infectious mononucleosis), scar formation, hyperproliferative vascular disease including intimal smooth muscle cell hyperplasia, restenosis, and vascular occlusion and the like.

The term "neoplastic disease" includes cancers characterized by solid tumors and non-solid tumors including but not limited to breast cancers; sarcomas (including but not limited to osteosarcomas and angiosarcomas and fibrosarcomas), leukemias, lymphomas, genitourinary cancers (including but not limited to ovarian, urethral, bladder, and prostate cancers); gastrointestinal cancers (including but not limited to colon esophageal and stomach cancers); lung cancers; myelomas; pancreatic cancers; liver cancers; kidney cancers; endocrine cancers; skin cancers; and brain or central and peripheral nervous (CNS) system tumors, malignant or benign, including gliomas and neuroblastomas, astrocytomas, myelodysplastic disorders; cervical carcinoma-in-situ; intestinal polyposes; oral leukoplakias; histiocytoses, hyperprofroliferative scars including keloid scars, hemangiomas; hyperproliferative arterial stenosis, psoriasis, inflammatory arthritis; hyperkeratoses and papulosquamous eruptions including arthritis.

The term neoplastic disease includes carcinomas. The term "carcinoma" refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The term neoplastic disease includes adenocarcinomas. An "adenocarcinoma" refers to a carcinoma derived from glandular tissue or in which the tumor cells form recognizable glandular structures.

As used herein, the term "hematopoietic neoplastic disorders" refers to neoplastic diseases involving hyperplastic/neoplastic cells of hematopoietic origin, e.g., arising from myeloid, lymphoid or erythroid lineages, or precursor cells thereof.

Myeloid neoplasms include, but are not limited to, myeloproliferative neoplasms, myeloid and lymphoid disorders with eosinophilia, myeloproliferative/myelodysplastic neoplasms, myelodysplastic syndromes, acute myeloid leukemia and related precursor neoplasms, and acute leukemia of ambiguous lineage. Exemplary myeloid disorders amenable to treatment in accordance with the present disclosure include, but are not limited to, acute promyeloid leukemia (APML), acute myelogenous leukemia (AML) and chronic myelogenous leukemia (CML).

Lymphoid neoplasms include, but are not limited to, precursor lymphoid neoplasms, mature B-cell neoplasms, mature T-cell neoplasms, Hodgkin's Lymphoma, and immunodeficiency-associated lymphoproliferative disorders. Exemplary lymphic disorders amenable to treatment in accordance with the present disclosure include, but are not limited to, acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM).

In some instances, the hematopoietic neoplastic disorder arises from poorly differentiated acute leukemias (e.g., erythroblastic leukemia and acute megakaryoblastic leukemia). As used herein, the term "hematopoietic neoplastic disorders" refers malignant lymphomas including, but are not limited to, non-Hodgkins lymphoma and variants thereof, peripheral T cell lymphomas, adult T-cell leukemia/lymphoma (ATL), cutaneous T cell lymphoma (CTCL), large granular lymphocytic leukemia (LGF), Hodgkin's disease and Reed-Stemberg disease.

The determination of whether a subject is "suffering from a neoplastic disease" refers to a determination made by a physician with respect to a subject based on the available information accepted in the field for the identification of a disease, disorder or condition including but not limited to X-ray, CT-scans, conventional laboratory diagnostic tests (e.g. blood count, etc.), genomic data, protein expression data, immunohistochemistry, that the subject requires or will benefit from treatment.

Combination Of IL10Ra binding molecules with Supplementary Anti-Neoplastic Agents:

The present disclosure provides for the use of the IL10Ra binding molecules of the present disclosure in combination with one or more additional active anti-neoplastic agents ("supplementary agents") for the treatment of neoplastic disease. Such further combinations are referred to interchangeably as "supplementary anti-neoplastic combinations" or "supplementary anti-neoplastic combination therapy" and those therapeutic agents that are used in combination with IL10Ra binding molecules of the present disclosure are referred to as "supplementary anti-neoplastic agents." As used herein, the term "supplementary anti-neoplastic agents" includes anti-neoplastic agents that can be administered or introduced separately, for example, formulated separately for separate administration (e.g., as may be provided in a kit) and/or therapies that can be administered or introduced in combination with the IL10Ra binding molecules.

Chemotherapeutic Agents:

In some embodiments, the supplementary anti-neoplastic agent is a chemotherapeutic agent. In some embodiments the supplementary agent is a "cocktail" of multiple chemotherapeutic agents. IN some embodiments the chemotherapeutic agent or cocktail is administered in combination with one or more physical methods (e.g. radiation therapy). The term "chemotherapeutic agents" includes but is not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins such as bleomycin A2, cactinomycin, calicheamicin, carabicin, caminomycin, carzinophilin, chromomycins, dactinomycin, daunorubicin and derivatives such as demethoxy-daunomycin, 11-deoxydaunorubicin, 13-deoxydaunorubicin, detorubicin, 6-diazo-5-oxo-L-norleucine, doxorubicin, epirubicin, esorubicin, idarubicin, marcellomycin, mitomycins such as mitomycin C, N-methyl mitomycin C; mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate, dideazatetrahydrofolic acid, and folinic acid; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel, nab-paclitaxel and doxetaxel; chlorambucil; gemcitabine; 6-thioguanine; mercaptopurine; methotrexate; platinum and platinum coordination complexes such as cisplatin, oxaplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins;

capecitabine; taxanes such as paclitaxel, docetaxel, cabazitaxel; carminomycin, adriamycins such as 4'-epiadriamycin, 4-adriamycin-14-benzoate, adriamycin-14-octanoate, adriamycin-14-naphthaleneacetate; cholchicine and pharmaceutically acceptable salts, acids or derivatives of any of the above.

The term "chemotherapeutic agents" also includes anti-hormonal agents that act to regulate or inhibit hormone action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above.

In some embodiments, a supplementary anti-neoplastic agent is one or more chemical or biological agents identified in the art as useful in the treatment of neoplastic disease, including, but not limited to, a cytokines or cytokine antagonists such as IL-12, INFα, or anti-epidermal growth factor receptor, irinotecan; tetrahydrofolate antimetabolites such as pemetrexed; antibodies against tumor antigens, a complex of a monoclonal antibody and toxin, a T-cell adjuvant, bone marrow transplant, or antigen presenting cells (e.g., dendritic cell therapy), anti-tumor vaccines, replication competent viruses, signal transduction inhibitors (e.g., Gleevec® or Herceptin®) or an immunomodulator to achieve additive or synergistic suppression of tumor growth, non-steroidal anti-inflammatory drugs (NSAIDs), cyclooxygenase-2 (COX-2) inhibitors, steroids, TNF antagonists (e.g., Remicade® and Enbrel®), interferon-01a (Avonex®), and interferon-β1b (Betaseron®) as well as combinations of one or more of the foregoing as practiced in known chemotherapeutic treatment regimens including but not limited to TAC, FOLFOX, TPC, FEC, ADE, FOLFOX-6, EPOCH, CHOP, CMF, CVP, BEP, OFF, FLOX, CVD, TC, FOLFIRI, PCV, FOLFOXIRI, ICE-V, XELOX, and others that are readily appreciated by the skilled clinician in the art.

In some embodiments, the IL10Ra binding molecule is administered in combination with BRAF/MEK inhibitors, kinase inhibitors such as sunitinib, PARP inhibitors such as olaparib, EGFR inhibitors such as osimertinib (Ahn, et al. (2016) J Thorac Oncol 11:S115), IDO inhibitors such as epacadostat, and oncolytic viruses such as talimogene laherparepvec (T-VEC).

Anti-Tumor Antigen Antibody Therapeutics as Supplementary Agents

In some embodiments, a "supplementary anti-neoplastic agent" is a therapeutic antibody (including bi-specific and tri-specific antibodies which bind to one or more tumor associated antigens including but not limited to bispecific T cell engagers (BITEs), dual affinity retargeting (DART) constructs, and trispecific killer engager (TriKE) constructs).

In some embodiments, the therapeutic antibody is an antibody that binds to at least one tumor antigen selected from the group consisting of HER2 (e.g. trastuzumab, pertuzumab, ado-trastuzumab emtansine), nectin-4 (e.g. enfortumab), CD79 (e.g. polatuzumab vedotin), CTLA4 (e.g. ipilumumab), CD22 (e.g. moxetumomab pasudotox), CCR4 (e.g. magamuizumab), IL23p19 (e.g. tildrakizumab), PDL1 (e.g. durvalumab, avelumab, atezolizumab), IL17a (e.g. ixekizumab), CD38 (e.g. daratumumab), SLAMF7 (e.g. elotuzumab), CD20 (e.g. rituximab, tositumomab, ibritumomab and ofatumumab), CD30 (e.g. brentuximab vedotin), CD33 (e.g. gemtuzumab ozogamicin), CD52 (e.g. alemtuzumab), EpCam, CEA, fpA33, TAG-72, CAIX, PSMA, PSA, folate binding protein, GD2 (e.g. dinutuximab), GD3, IL6 (e.g. silutxumab) GM2, Le$^y$, VEGF (e.g. bevacizumab), VEGFR, VEGFR2 (e.g. ramucirumab), PDGFRa (e.g. olartumumab), EGFR (e.g. cetuximab, panitumumab and necitumumab), ERBB2 (e.g. trastuzumab), ERBB3, MET, IGF1R, EPHA3, TRAIL R1, TRAIL R2, RANKL RAP, tenascin, integrin αVβ3, and integrin α4β1.

In some embodiments, a therapeutic antibody is an immune checkpoint modulator for the treatment and/or prevention neoplastic disease in a subject as well as diseases, disorders or conditions associated with neoplastic disease. The term "immune checkpoint pathway" refers to biological response that is triggered by the binding of a first molecule (e.g. a protein such as PD1) that is expressed on an antigen presenting cell (APC) to a second molecule (e.g. a protein such as PDL1) that is expressed on an immune cell (e.g. a T-cell) which modulates the immune response, either through stimulation (e.g. upregulation of T-cell activity) or inhibition (e.g. downregulation of T-cell activity) of the immune response. The molecules that are involved in the formation of the binding pair that modulate the immune response are commonly referred to as "immune checkpoints." In one embodiment, the immune checkpoint pathway modulator is an antagonist of a negative immune checkpoint pathway that inhibits the binding of PD1 to PDL1 and/or PDL2 ("PD1 pathway inhibitor). The term PD1 pathway inhibitors includes monoclonal antibodies that interfere with the binding of PD1 to PDL1 and/or PDL2. Examples of commercially available PD1 pathway inhibitors useful as supplementary agents in the treatment of neoplastic disease include antibodies that interfere with the binding of PD1 to PDL1 and/or PDL2 including but not limited to nivolumab (Opdivo®, BMS-936558, MDX1106, commercially available from BristolMyers Squibb, Princeton N.J.), pembrolizumab (Keytruda®MK-3475, lambrolizumab, commercially available from Merck and Company, Kenilworth N.J.), and atezolizumab (Tecentriq®, Genentech/Roche, South San Francisco Calif.). Additional PD1 pathway inhibitors antibodies are in clinical development including but not limited to durvalumab (MEDI4736, Medimmune/AstraZeneca), pidilizumab (CT-011, CureTech), PDR001 (Novartis), BMS-936559 (MDX1105, BristolMyers Squibb), and avelumab (MSB0010718C, Merck Serono/Pfizer) and SHR-1210 (Incyte). Additional antibody PD1 pathway inhibitors are described in U.S. Pat. No. 8,217,149 (Genentech, Inc) issued Jul. 10, 2012; U.S. Pat. No. 8,168,757 (Merck Sharp and Dohme Corp.) issued May 1, 2012, U.S. Pat. No. 8,008,449 (Medarex) issued Aug. 30, 2011, U.S. Pat. No. 7,943,743 (Medarex, Inc) issued May 17, 2011.

Examples of antibody therapeutics which are FDA approved and may be used as supplementary agents for use in the treatment of neoplastic disease include atezolizumab, olaratumab, ixekizumab, trastuzumab, infliximab, rituximab, edrecolomab, daratumumab, elotuzumab, necitumumab, dinutuximab, nivolumab, blinatumomab, pembrolizumab, pertuzumab, brentuximab vedotin, ipilimumab, ofatumumab, certolizumab pegol, catumaxomab, panitumumab, bevacizumab, ramucirumab, siltuximab, enfortumab vedotin, polatuzumab vedotin, [fam]-trastuzumab deruxtecan, cemiplimab, moxetumomab pasudotox, mogamuizumab, tildrakizumab, ibalizumab, durvalumab, inotuzumab, ozogamicin, avelumab, obinutuzumab, ado-trastuzumab emtansine, cetuximab, tositumomab-I131, ibritumomab tiuxetan, gemtuzumab, and ozogamicin.

Physical Methods

In some embodiments, a supplementary anti-neoplastic agent is one or more non-pharmacological modalities (e.g., localized radiation therapy or total body radiation therapy or surgery). By way of example, the present disclosure contemplates treatment regimens wherein a radiation phase is preceded or followed by treatment with a treatment regimen comprising a IL10Ra binding molecule and one or more supplementary anti-neoplastic agents. In some embodiments, the present disclosure further contemplates the use of a IL10Ra binding molecule in combination with surgery (e.g. tumor resection). In some embodiments, the present disclosure further contemplates the use of a IL10Ra binding molecule in combination with bone marrow transplantation, peripheral blood stem cell transplantation or other types of transplantation therapy.

Cell Therapies

In some embodiments, the methods of the disclosure may include the combination of the administration of a IL10Ra binding molecules with supplementary agents in the form of cell therapies for the treatment of neoplastic, autoimmune or inflammatory diseases. Examples of cell therapies that are amenable to use in combination with the methods of the present disclosure include but are not limited to engineered T cell products comprising one or more activated CAR-T cells, engineered TCR cells, tumor infiltrating lymphocytes (TILs), engineered Treg cells.

In CAR-Ts useful in the practice of the present invention are prepared in accordance with principles well known in the art. See e.g., Eshhaar et al. U.S. Pat. No. 7,741,465 B1 issued Jun. 22, 2010; Sadelain, et al (2013) Cancer Discovery 3(4):388-398; Jensen and Riddell (2015) Current Opinions in Immunology 33:9-15; Gross, et al. (1989) PNAS (USA) 86(24):10024-10028; Curran, et al. (2012) J Gene Med 14(6):405-15. Examples of commercially available CAR-T cell products include axicabtagene ciloleucel (marketed as Yescarta® commercially available from Gilead Pharmaceuticals) and tisagenlecleucel (marketed as Kymriah® commercially available from Novartis). In some embodiments, the CAR-T possesses a CAR specifically binds to a cell surface molecule associated with a tumor cell is selected from the group consisting of GD2, BCMA, CD19, CD33, CD38, CD70, GD2, IL3R□2, CD19, mesothelin, Her2, EpCam, Mucl, ROR1, CD133, CEA, EGRFRVIII, PSCA, GPC3, Pan-ErbB and FAP Identification, Isolation, Enrichment or Depletion of IL10Ra+ Cells In one embodiment, the present disclosure provides a method of use of the IL10Ra binding molecules of the present disclosure useful in a process for in the isolation, enrichment or depletion of IL10Ra+ cells from a biological sample comprising IL10Ra+ cells. The biological sample may comprise cells of blood origin such as PBMC, T cells, B cells of cell culture origin or of tissue origin such as brain or bone marrow. Processes suitable for the isolation, enrichment or depletion of IL10Ra+ cells comprise centrifugation, filtration, magnetic cell sorting and fluorescent cell sorting by techniques well known in the art. The present disclosure further provides a method for the treatment of a subject suffering from a disease, disorder or condition by the administration of a therapeutically effective amount of a cell product enriched or depleted of IL10Ra+ cells through the use of a IL10Ra binding molecule as described herein.

In one embodiment, the sorting procedure employs a IL10Ra binding molecule comprising a fluorescent label for use in FACS isolation or depletion of IL10Ra+ cells from a sample. The fluorescent label may be attached to the sdAb of the IL10Ra binding molecule directly (e.g., by chemical conjugation optionally employing a linker) or indirectly (e.g., by biotinylation of the sdAb and binding of the biotinylated antibody to a streptavidin fluorochrome conjugate). Such fluorescently labelled IL10Ra+ cells may be separated from a mixed cell population using conventional FACS technology.

In an alternative embodiment, the selection procedure employs IL10Ra binding molecules of the present disclosure (e.g., a IL10Ra binding VHH) conjugated to magnetic particles which provide magnetic labeling of the IL10Ra+ cells for use in magnetic cell separation procedures. In one embodiment the method comprises: (a) conjugation of one or more IL10Ra binding molecule of the present disclosure (e.g., a IL10Ra binding VHH) to a magnetic particle; (b) creating a mixture by contacting the biological sample with a quantity of the magnetic particles conjugated to IL10Ra binding molecule; (c) subjecting to a magnetic field such that the magnetically labelled IL10Ra+ cells are retained; (d) removing the non-magnetically labelled cells from the mixture; and (e) removal of the magnetic field enabling isolation of the IL10Ra+ cells.

The cell selection procedure (e.g., FACS or magnetic separation) results in two products: (a) a population of cells depleted of IL10Ra+ cells and (b) a population of cells enriched for IL10Ra+ cells. Each of these populations may be further processed by convention procedures to identify particular IL10Ra+ or IL10Ra− cell subsets which may be useful in research, diagnostic or clinical applications. For example, isolation of specific IL10Ra+ T cell subsets that also express one or more of CD4, CD8, CD19, CD25, and CD62L, further iterations of the using one or more antibodies that specifically bind to CD4, CD8, CD19, CD25, and CD62L antigens respectively by FACS or magnetic field separation by techniques well known in the art.

Combination with Supplementary Therapeutic Agents

The present disclosure provides for the use of the IL10Ra binding molecules of the present disclosure in combination with one or more additional active agents ("supplementary agents"). Such further combinations are referred to interchangeably as "supplementary combinations" or "supplementary combination therapy" and those therapeutic agents that are used in combination with IL10Ra binding molecules of the present disclosure are referred to as "supplementary agents." As used herein, the term "supplementary agents" includes agents that can be administered or introduced separately, for example, formulated separately for separate administration (e.g., as may be provided in a kit) and/or therapies that can be administered or introduced in combination with the IL10Ra binding molecules.

As used herein, the term "in combination with" when used in reference to the administration of multiple agents to a subject refers to the administration of a first agent at least one additional (i.e. second, third, fourth, fifth, etc.) agent to a subject. For purposes of the present invention, one agent (e.g., IL10Ra binding molecule) is considered to be administered in combination with a second agent (e.g., a modulator of an immune checkpoint pathway) if the biological effect resulting from the administration of the first agent persists in the subject at the time of administration of the second agent such that the therapeutic effects of the first agent and second agent overlap. For example, the PD1 immune checkpoint inhibitors (e.g., nivolumab or pembrolizumab) are typically administered by IV infusion every two weeks or every three weeks while the IL10Ra binding molecules of the present disclosure are typically administered more frequently, e.g., daily, BID, or weekly. However, the administration of the first agent (e.g., pembrolizumab) provides a therapeutic effect over an extended time and the administration of the second agent (e.g., an IL10Ra binding molecule) provides its therapeutic effect while the therapeutic effect of the first agent remains ongoing such that the second agent is considered to be administered in combination with the first agent, even though the first agent may have been administered at a point in time significantly distant (e.g., days or weeks) from the time of administration of the second agent. In one embodiment, one agent is considered to be administered in combination with a second agent if the first and second agents are administered simultaneously (within 30 minutes of each other), contemporaneously or sequentially. In some embodiments, a first agent is deemed to be administered "contemporaneously" with a second agent if first and second agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a second agent are co-formulated in single pharmaceutically acceptable formulation and the co-formulation is administered to a subject. In certain embodiments, the IL10Ra binding molecule and the supplementary agent(s) are administered or applied sequentially, e.g., where one agent is administered prior to one or more other agents. In other embodiments, the IL10Ra binding molecule and the supplementary agent(s) are administered simultaneously, e.g., where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

Chemotherapeutic Agents

In some embodiments, particularly in the treatment of neoplastic disease, the supplementary agent is a chemotherapeutic agent. In some embodiments the supplementary agent is a "cocktail" of multiple chemotherapeutic agents. In some embodiments the chemotherapeutic agent or cocktail is administered in combination with one or more physical methods (e.g., radiation therapy). The term "chemotherapeutic agents" includes but is not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins such as bleomycin A2, cactinomycin, calicheamicin, carabicin, caminomycin, carzinophilin, chromomycins, dactinomycin, daunorubicin and derivaties such as demethoxy-daunomycin, 11-deoxydaunorubicin, 13-deoxydaunorubicin, detorubicin, 6-diazo-5-oxo-L-norleucine, doxorubicin, epirubicin, esorubicin, idarubicin, marcellomycin, mitomycins such as mitomycin C, N-methyl mitomycin C; mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate, dideazatetrahydrofolic acid, and folinic acid; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel, nab-paclitaxel and doxetaxel; chlorambucil; gemcitabine; 6-thioguanine; mercaptopurine; methotrexate; platinum and platinum coordination complexes such as cisplatin, oxaplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; taxanes such as paclitaxel, docetaxel, cabazitaxel; carminomycin, adriamycins such as 4'-epiadriamycin, 4-adriamycin-14-benzoate, adriamycin-14-octanoate, adriamycin-14-naphthaleneacetate; cholchicine and pharmaceutically acceptable salts, acids or derivatives of any of the above.

The term "chemotherapeutic agents" also includes antihormonal agents that act to regulate or inhibit hormone action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above.

In some embodiments, a supplementary agent is one or more chemical or biological agents identified in the art as useful in the treatment of neoplastic disease, including, but not limited to, a cytokines or cytokine antagonists such as IL-12, INFα, or anti-epidermal growth factor receptor, irinotecan; tetrahydrofolate antimetabolites such as pemetrexed; antibodies against tumor antigens, a complex of a monoclonal antibody and toxin, a T-cell adjuvant, bone marrow transplant, or antigen presenting cells (e.g., dendritic cell therapy), anti-tumor vaccines, replication competent viruses, signal transduction inhibitors (e.g., Gleevec® or Herceptin®) or an immunomodulator to achieve additive or synergistic suppression of tumor growth, non-steroidal anti-inflammatory drugs (NSAIDs), cyclooxygenase-2 (COX-2) inhibitors, steroids, TNF antagonists (e.g., Remicade® and Enbrel®), interferon-β1a (Avonex®), and interferon-β1b (Betaseron®) as well as combinations of one or more of the foregoing as practiced in known chemotherapeutic treatment regimens including but not limited to TAC, FOLFOX, TPC, FEC, ADE, FOLFOX-6, EPOCH, CHOP, CMF, CVP, BEP, OFF, FLOX, CVD, TC, FOLFIRI, PCV, FOLFOXIRI, ICE-V, XELOX, and others that are readily appreciated by the skilled clinician in the art.

In some embodiments, the IL10Ra binding molecule is administered in combination with BRAF/MEK inhibitors, kinase inhibitors such as sunitinib, PARP inhibitors such as olaparib, EGFR inhibitors such as osimertinib (Ahn, et al. (2016) J Thorac Oncol 11:S115), IDO inhibitors such as epacadostat, and oncolytic viruses such as talimogene laherparepvec (T-VEC).

Therapeutic Antibodies

In some embodiments, a "supplementary agent" is a therapeutic antibody (including bi-specific and tri-specific antibodies which bind to one or more tumor associated antigens including but not limited to bispecific T cell engagers (BITEs), dual affinity retargeting (DART) constructs, and trispecific killer engager (TriKE) constructs).

In some embodiments, the therapeutic antibody is an antibody that binds to at least one tumor antigen selected from the group consisting of HER2 (e.g., trastuzumab, pertuzumab, ado-trastuzumab emtansine), nectin-4 (e.g., enfortumab), CD79 (e.g., polatuzumab vedotin), CTLA4 (e.g., ipilumumab), CD22 (e.g., moxetumomab pasudotox), CCR4 (e.g., magamuizumab), IL23p19 (e.g., tildrakizumab), PDL1 (e.g., durvalumab, avelumab, atezolizumab), IL17a (e.g., ixekizumab), CD38 (e.g., daratumumab), SLAMF7 (e.g., elotuzumab), CD20 (e.g., rituximab, tositumomab, ibritumomab and ofatumumab), CD30 (e.g., brentuximab vedotin), CD33 (e.g., gemtuzumab ozogamicin), CD52 (e.g., alemtuzumab), EpCam, CEA, fpA33, TAG-72, CAIX, PSMA, PSA, folate binding protein, GD2 (e.g., dinuntuximab), GD3, IL6 (e.g., silutxumab) GM2, Le, VEGF (e.g., bevacizumab), VEGFR, VEGFR2 (e.g., ramucirumab), PDGFR (e.g., olartumumab), EGFR (e.g., cetuximab, panitumumab and necitumumab), ERBB2 (e.g., trastuzumab), ERBB3, MET, IGF1R, EPHA3, TRAIL R1, TRAIL R2, RANKL RAP, tenascin, integrin $\alpha V\beta 3$, and integrin $\alpha 4\beta 1$.

Cell Therapy Agents and Methods as Supplementary Agents

In some embodiments, the methods of the disclosure may include the administration of a IL10Ra binding molecule of the present disclosure in combination with supplementary agents in the form of cell therapies for the treatment of neoplastic, autoimmune or inflammatory diseases. Examples of cell therapies that are amenable to use in combination with the methods of the present disclosure include but are not limited to engineered T cell products comprising one or more first, second, third or fourth generation. CAR-T cells, engineered TCR cells, tumor infiltrating lymphocytes (TILs), and engineered Treg cells. In some embodiments, the extracellular domain of the chimeric antigen receptor of the CAR T cell is a polypeptide that specifically binds to one or more cell surface molecules preferentially or uniquely expressed on the extracellular surface of neoplastic cell (e.g., a tumor antigen) selected from the group consisting of GD2, BCMA, CD19, PSMA, CD33, CD38, CD70, GD2, IL3R☐2, CD2, mesothelin, Her2, EpCam, Mucl, ROR1, CD133, CEA, EGRFRVIII, PSCA, GPC3, Pan-ErbB and FAP.

Physical Methods

In some embodiments, the supplementary agent is an anti-neoplastic physical method including but not limited to radiotherapy, cryotherapy, hyperthermic therapy, surgery, laser ablation, and proton therapy.

Formulations

The present disclosure further provides pharmaceutically acceptable formulations of the IL10Ra binding molecules of the present disclosure. The preferred formulation depends on the intended mode of administration and therapeutic application. Pharmaceutical dosage forms of the IL10Ra binding molecules described herein comprise physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of polypeptides include polysaccharides such as sodium carboxymethylcellulose or methylcellulose, polyvinylpyrrolidone, polyacrylates, polyoxyethylene-polyoxypropylene-block polymers, PEG, polymeric amino acids, amino acid copolymers, and lipid aggregates (such as oil droplets or liposomes).

The pharmaceutical compositions may also comprise pharmaceutically-acceptable, non-toxic carriers, excipients, stabilizers, or diluents, which are defined as vehicles commonly used to formulate pharmaceutical compositions for animal or human administration. The diluent is selected so as not to affect the biological activity of the combination. Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Formulations to be used for in vivo administration are typically sterile. Sterilization of the compositions of the present disclosure may readily accomplished by filtration through sterile filtration membranes.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (Langer, Science 249: 1527, 1990 and Hanes, *Advanced Drug Delivery Reviews* 28: 97-119, 1997). The agents of this disclosure can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Vector Delivery of Polypeptide IL10Ra Binding Molecules

In those embodiments where the IL10Ra binding molecule is a polypeptide, such IL10Ra binding molecules may also be delivered to a subject through the administration of a recombinant vectors comprising a nucleic acid sequence encoding the peptidyl IL10Ra binding molecule operably linked to an expression control sequence in the cells of the tissues of the subject.

Expression vectors may be viral vectors or non-viral vectors. The term "nonviral vector" refers to an autonomously replicating, extrachromosomal circular DNA molecule, distinct from the normal genome and nonessential for cell survival under nonselective conditions capable of effecting the expression of an coding sequence in the target cell. Plasmids are examples of non-viral vectors. In order to facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, magnetic fields (electroporation)

In one embodiment, a non-viral vector may be provided in a non-viral delivery system. Non-viral delivery systems are typically complexes to facilitate transduction of the target cell with a nucleic acid cargo wherein the nucleic acid is complexed with agents such as cationic lipids (DOTAP, DOTMA), surfactants, biologicals (gelatin, chitosan), metals (gold, magnetic iron) and synthetic polymers (PLG, PEI, PAMAM). Numerous embodiments of non-viral delivery systems are well known in the art including lipidic vector systems (Lee et al. (1997) Crit Rev Ther Drug Carrier Syst. 14:173-206); polymer coated liposomes (Marin et al., U.S. Pat. No. 5,213,804, issued May 25, 1993; Woodle, et al., U.S. Pat. No. 5,013,556, issued May 7, 1991); cationic liposomes (Epand et al., U.S. Pat. No. 5,283,185, issued Feb. 1, 1994; Jessee, J. A., U.S. Pat. No. 5,578,475, issued Nov. 26, 1996; Rose et al, U.S. Pat. No. 5,279,833, issued Jan. 18, 1994; Gebeyehu et al., U.S. Pat. No. 5,334,761, issued Aug. 2, 1994).

In another embodiment, the expression vector may be a viral vector. As used herein, the term viral vector is used in its conventional sense to refer to any of the obligate intracellular parasites having no protein-synthesizing or energy-generating mechanism and generally refers to any of the enveloped or non-enveloped animal viruses commonly employed to deliver exogenous transgenes to mammalian cells. A viral vector may be replication competent (e.g., substantially wild-type), conditionally replicating (recombinantly engineered to replicate under certain conditions) or replication deficient (substantially incapable of replication in the absence of a cell line capable of complementing the deleted functions of the virus). The viral vector can possess certain modifications to make it "specifically replicating," i.e. that it replicates preferentially in certain cell types or phenotypic cell states, e.g., cancerous. Viral vector systems useful in the practice of the instant IL10Ra binding molecule include, for example, naturally occurring or recombinant viral vector systems. Examples of viruses useful in the practice of the present IL10Ra binding molecule include recombinantly modified enveloped or non-enveloped DNA and RNA viruses. For example, viral vectors can be derived from the genome of human or bovine adenoviruses, vaccinia virus, lentivirus, herpes virus, adeno-associated virus, human immunodeficiency virus, sindbis virus, and retroviruses (including but not limited to Rous sarcoma virus), and hepatitis B virus. Typically, genes of interest are inserted into such vectors to allow packaging of the gene construct, typically with accompanying viral genomic sequences, followed by infection of a sensitive host cell resulting in expression of the gene of interest (e.g., a targeting antigen).

The expression vector may encode one or more polypeptides in addition to the targeting antigen. When expressing multiple polypeptides as in the practice of the present IL10Ra binding molecule, each polypeptide may be operably linked to an expression control sequence (monocistronic) or multiple polypeptides may be encoded by a polycistronic construct where multiple polypeptides are expressed under the control of a single expression control sequence. In one embodiment, the expression vector encoding the targeting antigen may optionally further encode one or more immunological modulators. Examples of immunological modulators useful in the practice of the present IL10Ra binding molecule include but are not limited to cytokines. Examples of such cytokines are interleukins including but not limited to one more or of IL-1, IL-2, IL-3, IL-4, IL-12, TNF-alpha, interferon alpha, interferon alpha-2b, interferon-beta, interferon-gamma, GM-CSF, MIP1-alpha, MIP1-beta, MIP3-alpha, TGF-beta and other suitable cytokines capable of modulating immune response. The expressed cytokines can be directed for intracellular expression or expressed with a signal sequence for extracellular presentation or secretion.

The expression vector may optionally provide an additional expression cassette comprising a nucleic acid sequence encoding a "rescue" gene. A "rescue gene" is a nucleic acid sequence, the expression of which renders the cell susceptible to killing by external factors or causes a toxic condition in the cell such that the cell is killed. Providing a rescue gene enables selective cell killing of transduced cells. Thus, the rescue gene provides an additional safety precaution when said constructs are incorporated into the cells of a mammalian subject to prevent undesirable spreading of transduced cells or the effects of replication competent vector systems. In one embodiment, the rescue gene is the thymidine kinase (TK) gene (see e.g., Woo, et al. U.S. Pat. No. 5,631,236 issued May 20, 1997 and Freeman, et al. U.S. Pat. No. 5,601,818 issued Feb. 11, 1997) in which the cells expressing the TK gene product are susceptible to selective killing by the administration of gancyclovir.

Dosage

The present disclosure further provides the administration of therapeutically or prophylactically effective dose of IL10Ra binding molecule or a recombinant vector or cell comprising a nucleic acid sequence encoding a polypeptide IL10Ra binding molecule to a subject suffering from or at risk of developing, respectively, a disease, disorder or condition. The dosage of the pharmaceutical composition comprising the IL10Ra binding molecules, vector or cell depends on factors including the route of administration, the disease to be treated, and physical characteristics, e.g., age, weight, general health, of the subject. Typically, the amount of a IL10Ra binding molecule contained within a single dose may be an amount that effectively prevents, delays, or treats the disease without inducing significant toxicity. A pharmaceutical composition of the disclosure may include a dosage of a IL10Ra binding molecule described herein ranging from 0.01 to 500 mg/kg (e.g., from 0.01 to 450 mg, from 0.01 to 400 mg, from 0.01 to 350 mg, from 0.01 to 300 mg, from 0.01 to 250 mg, from 0.01 to 200 mg, from 0.01 to 150 mg, from 0.01 to 100 mg, from 0.01 to 50 mg, from 0.01 to 10 mg, from 0.01 to 1 mg, from 0.1 to 500 mg/kg, from 1 to 500 mg/kg, from 5 to 500 mg/kg, from 10 to 500 mg/kg, from 50 to 500 mg/kg, from 100 to 500 mg/kg, from 150 to 500 mg/kg, from 200 to 500 mg/kg, from 250 to 500 mg/kg, from 300 to 500 mg/kg, from 350 to 500 mg/kg, from 400 to 500 mg/kg, or from 450 to 500 mg/kg) and, in a more specific embodiment, about 1 to about 100 mg/kg (e.g., about 1 to about 90 mg/kg, about 1 to about 80 mg/kg, about 1 to about 70 mg/kg, about 1 to about 60 mg/kg, about 1 to about 50 mg/kg, about 1 to about 40 mg/kg, about 1 to about 30 mg/kg, about 1 to about 20 mg/kg, about 1 to about 10 mg/kg, about to about 100 mg/kg, about 20 to about 100 mg/kg, about 30 to about 100 mg/kg, about 40 to about 100 mg/kg, about 50 to about 100 mg/kg, about 60 to about 100 mg/kg, about 70 to about 100 mg/kg, about 80 to about 100 mg/kg, or about 90 to about 100 mg/kg). In some embodiments, a pharmaceutical composition of the disclosure may include a dosage of a binding protein described herein ranging from 0.01 to 20 mg/kg (e.g., from 0.01 to 15 mg/kg, from 0.01 to 10 mg/kg, from 0.01 to 8 mg/kg, from 0.01 to 6 mg/kg, from 0.01 to 4 mg/kg, from 0.01 to 2 mg/kg, from 0.01 to 1 mg/kg, from 0.01 to 0.1 mg/kg, from 0.01 to 0.05 mg/kg, from 0.05 to 20 mg/kg, from 0.1 to 20 mg/kg, from 1 to 20 mg/kg, from 2 to 20 mg/kg, from 4 to 20 mg/kg, from 6 to 20 mg/kg, from 8 to 20 mg/kg, from 10 to 20 mg/kg, from 15 to 20 mg/kg). The dosage may be adapted by the physician in accordance with conventional factors such as the extent of the disease and different parameters of the subject.

A pharmaceutical composition containing a IL10Ra binding molecule described herein can be administered to a subject in need thereof, for example, one or more times (e.g., 1-10 times or more) daily, weekly, monthly, biannually, annually, or as medically necessary. Dosages may be provided in either a single or multiple dosage regimens. The timing between administrations may decrease as the medical condition improves or increase as the health of the patient declines. A course of therapy may be a single dose or in multiple doses over a period of time. In some embodiments, a single dose is used. In some embodiments, two or more split doses administered over a period of 1, 2, 3, 4, 5, 6, 7, 8, 9, 10, 11, 12, 13, 14, 21, 28, 30, 60, 90, 120 or 180 days are used. Each dose administered in such split dosing protocols may be the same in each administration or may be different. Multi-day dosing protocols over time periods may be provided by the skilled artisan (e.g., physician) monitoring the administration, taking into account the response of the subject to the treatment including adverse effects of the treatment and their modulation as discussed above.

For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

In some embodiments the condition to be treated is a chronic condition (e.g., a chronic infection, i.e., an infection that is not cleared by the host immune system within a period of up to 1 week, 2 weeks, etc.). In some cases, chronic condition involve integration of pathogen genetic elements into the host genome, e.g., retroviruses, lentiviruses, Hepatitis B virus, etc. In other cases, chronic infections, for example certain intracellular bacteria or protozoan pathogens, result from a pathogen cell residing within a host cell. Additionally, in some embodiments, the infection is in a latent stage, as with herpes viruses or human papilloma viruses. In such instances, the course of therapy may involve the administration of the IL10Ra binding molecule over an extended period of time including continued administration in the substantial absence of the symptoms of the chronic condition to prevent recurrence of the chronic conditions or symptoms thereof.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Routes of Administration

Administration of a IL10Ra binding molecules described herein may be achieved through any of a variety of art recognized methods including but not limited to the topical, intravascular injection (including intravenous or intraarterial infusion), intradermal injection, subcutaneous injection, intramuscular injection, intraperitoneal injection, intracranial injection, intratumoral injection, intranodal injection, transdermal, transmucosal, iontophoretic delivery, intralymphatic injection (Senti and Kundig (2009) *Current Opinions in Allergy and Clinical Immunology* 9(6):537-543), intragastric infusion, intraprostatic injection, intravesical infusion (e.g., bladder), respiratory inhalers including nebulizers, intraocular injection, intraabdominal injection, intralesional injection, intraovarian injection, intracerebral infusion or injection, intracerebroventricular injection (ICVI), and the like. Administration to the subject may be achieved by intravenous, as a bolus or by continuous infusion over a period of time. Examples of parenteral routes of administration include, for example, intravenous, intradermal, subcutaneous, transdermal (topical), transmucosal, and rectal administration. The IL10Ra binding molecule can be administered once, continuously, such as by continuous pump, or at periodic (e.g., daily, bi-weekly, monthly) intervals over a period of time can occur over the period of one week, two weeks, one month, two months, three months or more. Desired time intervals of multiple doses of the IL10Ra binding molecule may be determined by one of skill in the art.

As described herein above, the compositions of the present disclosure may be used in combination with one or more additional therapeutically effective agents. As used herein, the term "in combination with" when used in reference to the administration of multiple agents to a subject refers to the administration of a first agent at least one additional (i.e. second, third, fourth, fifth, etc.) supplementary agent to a subject. For purposes of the present disclosure, one agent (e.g., a IL10Ra binding molecule) is considered to be administered in combination with a supplementary agent if the biological effect resulting from the administration of the first agent persists in the subject at the time of administration of the supplementary agent such that the therapeutic effects of the first agent and second agent overlap. The administration of the first agent may provide a therapeutic effect over an extended time and the administration of the supplementary agent provides its therapeutic effect while the therapeutic effect of the first agent remains ongoing such that the supplementary agent is considered to be administered in combination with the first agent, even though the first agent may have been administered at a point in time significantly distant (e.g., days or weeks) from the time of administration of the supplementary agent. In one embodiment, one agent is considered to be administered in combination with a supplementary agent if the first and second agents are administered simultaneously (within 30 minutes of each other), contemporaneously or sequentially. In some embodiments, a first agent is deemed to be administered "contemporaneously" with a supplementary agent if first and supplementary agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a supplementary agent are co-formulated in single pharmaceutically acceptable formulation and the co-formulation is administered to a subject. In certain embodiments, first agent and the supplementary agent(s) are administered or applied sequentially, e.g., where one agent is administered prior to one or more other agents. In other embodiments, the first agent and the supplementary agent(s) are administered simultaneously, for example where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

Kits

The present disclosure also contemplates kits comprising pharmaceutical compositions of IL10Ra binding molecules. In some embodiments, the kit further comprises supplementary pharmaceutical compositions comprising supplementary agents as discussed above for use in combination therapy with IL10Ra binding molecules. The kits are generally in the form of a physical structure housing various components, as described below, and can be utilized, for example, in practicing the methods described above. A kit may comprise a IL10Ra binding molecule in the form of a pharmaceutical composition suitable for administration to a subject that is ready for use or in a form or requiring preparation for example, thawing, reconstitution or dilution prior to administration. When the IL10Ra binding molecule is in a form that requires reconstitution by a user, the kit may also comprise a sterile container providing a reconstitution medium comprising buffers, pharmaceutically acceptable excipients, and the like. A kit of the present disclosure can be designed for conditions necessary to properly maintain the components housed therein (e.g., refrigeration or freezing). A kit may further contain a label or packaging insert including identifying information for the components therein and instructions for their use. Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial). Labels or inserts may be provided in a physical form or a computer readable medium. In some embodiments, the actual instructions are not present in the kit, but rather the kit provides a means for obtaining the instructions from a remote source, e.g., via an internet site, including by secure access by providing a password (or scannable code such as a barcode or QR code on the container of the IL10Ra binding molecule or kit comprising) in compliance with governmental regulations (e.g., HIPAA) are provided.

EXAMPLES

The following examples are put forth so as to provide those of ordinary skill in the art with a complete disclosure and description of how to make and use the present IL10Ra binding molecule, and are not intended to limit the scope of what the inventors regard as their IL10Ra binding molecule nor are they intended to represent that the experiments below were performed and are all of the experiments that can be performed. It is to be understood that exemplary descriptions written in the present tense were not necessarily performed, but rather that the descriptions can be performed to generate the data and the like described therein. Efforts have been made to ensure accuracy with respect to numbers used (e.g., amounts, temperature, etc.), but some experimental errors and deviations should be accounted for. Variations of the particularly described procedures employed may become apparent to individuals or skill in the art and it is expected that those skilled artisans may employ such variations as appropriate. Accordingly, it is intended that the IL10Ra binding molecule be practiced otherwise than as specifically described herein, and that the invention includes all modifications and equivalents of the subject matter recited in the claims appended hereto as permitted by applicable law.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); pg=picogram; ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; PCR=polymerase chain reaction; NHS=N-hydroxysuccinimide; HSA=human serum albumin; MSA=mouse serum albumin; DMEM=Dulbeco's Modification of Eagle's Medium; GC=genome copy; EDTA=ethylenediaminetetraacetic acid; PBMCs=primary peripheral blood mononuclear cells; FBS=fetal bovine serum; FCS=fetal calf serum; HEPES=4-(2-hydroxyethyl)-lpiperazineethanesulfonic acid; LPS=lipopolysaccharide; ATCC=American Type Culture Collection Example 1. Immunization Protocol The VHH was obtained by immunization of a camel with the extracellular domain (amino acids 22-235) of hIL10Ra (UNIPROT Ref: Q13651). A synthetic DNA sequence encoding the antigen was inserted into the pFUSE_hIgG1_Fc2 vector (Generay Biotechnology) and transfected into the HEK293F mammalian cell host cell for expression. The antigen is expressed as an Fc fusion protein which is purified using Protein A chromatography. The antigen was diluted with 1×PBS (antigen total about 1 mg). The quality was estimated by SDS-PAGE to ensure the purity was sufficient (>80%) for immunization. The camel was acclimated at the facility for at least 7 days before immunization. The immunization with the antigen was conducted using once weekly administration of the antigen over a period of 7 weeks. For the initial immunization, the immunogen was prepared as follows: 10 mL of complete Freund's Adjuvant (CFA) was added into mortar, then 10 mL antigen in 1×PBS was slowly added into the mortar with the pestle grinding and sample ground until the antigen was emulsified until milky white and hard to disperse. For the subsequent six immunizations (weeks 2-7) in the immunization protocol, immunogen was prepared as above except that Incomplete Freund's Adjuvant (IFA) was used in place of CFA. At least six sites on the camel were injected subcutaneously with approximately 2 ml of the emulsified antigen for a total of approximately 10 mL per camel. When injecting the antigen, the needle is maintained in the in the subcutaneous space for approximately 10 to 15 seconds after each injection to avoid leakage of the emulsion.

Example 2. Phage Library Construction

A blood sample was collected from the camel three days following the last injection in the immunization protocol. RNA was extracted from blood and transcribed to cDNA. The approximately 900 bp reverse transcribed sequences encoding the VH-CH1-hinge-CH2-CH3 constructs were isolated from the approximately desired 700 bp fragments encoding the VHH-hinge-CH2-CH3 species. The purified approximately 700 bp fragments were amplified by nested PCR. The amplified sequences were digested using Pst1 and Not1. The approximately 400 bp PST1/Not1 digested fragments were inserted into a Pst1/Not1 digested pMECS phagemid vector such that the sequence encoding the VHH was in frame with a DNA sequence encoding a HA/His sequence. The PCR generated sequences and the vector of pMECS phagemid were digested with Pst I and Not I, subsequently, ligated to pMECS/Nb recombinant. After ligation, the products were transformed into *Escherichia coli* (*E. coli*) TG1 cells by electroporation. The transformants were enriched in growth medium, followed by transfer to 2YT+ 2% glucose agar plates.

Example 3: Isolation of Antigen Specific VHHs

Bio-panning of the phage library was conducted to identify VHHs that bind IL10Ra. A 96-well plate was coated with IL10Ra and the phage library was incubated in each well to allow phage-expressing IL10Ra reactive VHH to bind to the IL10Ra on the plate. Non-specifically bound phage were washed off and the specifically bound phage isolated. After the selection, the enriched phage library expressing IL10Ra reactive VHH were amplified in TG1 cells. The aforementioned bio-panning process was repeated for 2-3 rounds to enrich the library for VHH selective for IL10Ra.

Example 4: Identification of Antibodies Exhibiting Specific Binding to IL10Ra

Upon completion of the biopanning of Example 3, three 96-well plates of individual phage clones were isolated in order to perform periplasmic extract ELISA (PE-ELISA) on IL10Ra coated plates to identify positive VHH binders that selectively bound IL10Ra. A 96-well plate was coated with IL10Ra and PBS under the same conditions. Next, wells were blocked at 37° C. for 1 h. Then, 100 µl of extracted antibodies was added to each well and incubated for 1 h. Subsequently, 100 µl of anti-tag polyclonal antibody conjugated to HRP was added to each well and incubated at 37° C. for 1 h. Plates were developed with TMB substrate. The reaction was stopped by the addition of H2SO4. Absorbance at 450 nm was read on a microtiter plate reader. Antibodies with absorbance of the antigen-coated well at least threefold greater than PBS-coated control are VHHs that specifically bind to IL10Ra. Positive clones were sequenced, and sequences analyzed to identify unique clonotypes Example 5. Evaluation of Binding Affinity Via Surface Plasmon Resonance One representative example from each clonotype generated in accordance with Examples 1-3 was selected for evaluation of binding via SPR as follows. Evaluation of binding affinity of the IL10Ra binding molecules for IL10Ra corresponding to SEQ ID NOS 21, 29, 33, 37, 45, 53 and 65 was conducted using surface plasmon resonance (SPR) in substantial accordance with the following procedure. All experiments were conducted in 10 mM Hepes, 150 mM NaCl, 0.05% (v/v) Polysorbate 20 (PS20) and 3 mM EDTA (HBS-EP+ buffer) on a Biacore T200 instrument equipped with a Protein A derivatized sensor chip (Cytiva). Mono-Fc VHH ligands were flowed at 5 µl/min for variable time ranging from 18 to 300 seconds, reaching the capture loads listed in the tables below. Following ligand capture, injections of a 2-fold dilution series of the extracellular domain of the IL10Ra-receptor modified to incorporate a C-terminal poly-His sequence, typically comprising at least five concentrations between 1 µM and 1 nM, were performed in either high performance or single cycle kinetics mode. Surface regeneration was achieved by flowing 10 mM glycine-HCl, pH 1.5 (60 seconds, 50 µL/min). Buffer-subtracted sensograms were processed with Biacore T200 Evaluation Software and globally fit with a 1:1 Langmuir binding model (bulk shift set to zero) to extract kinetics and affinity constants ($k_a$, $k_d$, $K_D$). $R_{MAX}$<100 RU indicates surface density compatible with kinetics analysis. Calculated $R_{max}$ values were generated using the equation: Rmax=Load (RU)×valency of ligand×(Molecular weight of analyte/Molecular weight of ligand). Surface activity was defined as the ratio of experimental/calculated Rmax. The results of these binding affinity experiments are provided in Table 4 above.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

The invention claimed is:

1. A IL10Ra binding molecule that specifically binds to the extracellular domain of IL10Ra, wherein the IL10Ra binding molecule comprises a single domain antibody (sdAb), and wherein the sdAb comprises a complementary determining region 1 (CDR1), a CDR2, and a CDR3 as shown in a row of the table below

| CDR1 | CDR2 | CDR3 |
|---|---|---|
| YLYSIDYMA (SEQ ID NO: 2) | VIYTASGATFYPDSVKG (SEQ ID NO: 3) | VRKTDSYLFDAQSFTY (SEQ ID NO: 4) |
| YLYSTNYMA (SEQ ID NO: 6) | VIYTASGATLYTDSVKG (SEQ ID NO: 7) | VRKTDSYLFDAQSFTY (SEQ ID NO: 8) |
| YLYSTNYMA (SEQ ID NO: 18) | AIYTASGATLYSDSNKG (SEQ ID NO: 19) | VRKTGSYLFDAQSFTY (SEQ ID NO: 20) |
| FTYSSYCMG (SEQ ID NO: 22) | SIDSDGSTSYTDSVKG (SEQ ID NO: 23) | DLMSTVVPGFCGFLLS AGMDY (SEQ ID NO: 24) |
| YTFNSNCMG (SEQ ID NO: 26) | TIYTGVGSTYYADSVKG (SEQ ID NO: 27) | EPLSRVYGGSCPTPTF GY (SEQ ID NO: 28) |
| YTYSMYCMG (SEQ ID NO: 30) | QINSDGSTSYADSVKG (SEQ ID NO: 31) | DSRVYGGSWYERLCGP YTYEYNY (SEQ ID NO: 32) |
| YAYSTYCMG (SEQ ID NO: 34) | AIDSGGSTSYADSVKG (SEQ ID NO: 35) | VPPPPDGGSCLFLGPE IKVSKADFRY (SEQ ID NO: 36) |
| YTYSSYCMG (SEQ ID NO: 42) | VIDSDGSTSYADSVKG (SEQ ID NO: 43) | DLGHYRPPCGVLYLGM DY (SEQ ID NO: 44) |
| YTYSSNCMG (SEQ ID NO: 46) | TIYTGGGNTYYADSVKG (SEQ ID NO: 47) | EPLSRVYGGSCPTPTF DY (SEQ ID NO: 48) |
| YSYSSNCMG (SEQ ID NO: 50) | TIHTGGGSTYYADSVKG (SEQ ID NO: 51) | EPLSRLYGGSCPTPTF GY (SEQ ID NO: 52) |
| YTYSGYCMG (SEQ ID NO: 58) | VIDSDGSTSYADSVKG (SEQ ID NO: 59) | DLGHYRPPCGVLYLGM DY (SEQ ID NO: 60) |

-continued

| CDR1 | CDR2 | CDR3 |
|---|---|---|
| YTYSNYCMG (SEQ ID NO: 62) | TIDSDGNTSYADSVKG (SEQ ID NO: 63) | DLGHYRPPCGAYYYGM DY (SEQ ID NO: 64) |
| YSNCSYDMT (SEQ ID NO: 66) | AIHSDGSTRYADSVKG (SEQ ID NO: 67) | DPLHCRAHGGSWYSVR ANY (SEQ ID NO: 68) |
| YTYNSNCMG (SEQ ID NO: 70) | TIYTGVGSTYYADSVKG (SEQ ID NO: 71) | EPLSRVYGGSCPTPTF GY (SEQ ID NO: 72). |

2. The IL10Ra binding molecule of claim 1 wherein the sdAb is humanized or otherwise comprises CDRs grafted onto a heterologous framework.

3. The IL10Ra binding molecule of claim 1, wherein the sdAb comprises a CDR1, a CDR2, and a CDR3 comprising the amino acid sequences of SEQ ID NO: 2-4, respectively.

4. The IL10Ra binding molecule of claim 1, wherein the sdAb comprises a CDR1, a CDR2, and a CDR3 comprising the amino acid sequences of SEQ ID NO: 6-8, respectively.

5. The IL10Ra binding molecule of claim 1, wherein the sdAb comprises a CDR1, a CDR2, and a CDR3 comprising the amino acid sequences of SEQ ID NO: 18-20, respectively.

6. The IL10Ra binding molecule of claim 1, wherein the sdAb comprises a CDR1, a CDR2, and a CDR3 comprising the amino acid sequences of SEQ ID NO: 22-24, respectively.

7. The IL10Ra binding molecule of claim 1, wherein the sdAb comprises a CDR1, a CDR2, and a CDR3 comprising the amino acid sequences of SEQ ID NO: 26-28, respectively.

8. The IL10Ra binding molecule of claim 1, wherein the sdAb comprises a CDR1, a CDR2, and a CDR3 comprising the amino acid sequences of SEQ ID NO: 30-32, respectively.

9. The IL10Ra binding molecule of claim 1, wherein the sdAb comprises a CDR1, a CDR2, and a CDR3 comprising the amino acid sequences of SEQ ID NO: 34-36, respectively.

10. The IL10Ra binding molecule of claim 1, wherein the sdAb comprises a CDR1, a CDR2, and a CDR3 comprising the amino acid sequences of SEQ ID NO: 42-44, respectively.

11. The IL10Ra binding molecule of claim 1, wherein the sdAb comprises a CDR1, a CDR2, and a CDR3 comprising the amino acid sequences of SEQ ID NO: 46-48, respectively.

12. The IL10Ra binding molecule of claim 1, wherein the sdAb comprises a CDR1, a CDR2, and a CDR3 comprising the amino acid sequences of SEQ ID NO: 50-52, respectively.

13. The IL10Ra binding molecule of claim 1, wherein the sdAb comprises a CDR1, a CDR2, and a CDR3 comprising the amino acid sequences of SEQ ID NO: 58-60, respectively.

14. The IL10Ra binding molecule of claim 1, wherein the sdAb comprises a CDR1, a CDR2, and a CDR3 comprising the amino acid sequences of SEQ ID NO: 62-64, respectively.

15. The IL10Ra binding molecule of claim 1, wherein the sdAb comprises a CDR1, a CDR2, and a CDR3 comprising the amino acid sequences of SEQ ID NO: 66-68, respectively.

16. The IL10Ra binding molecule of claim 1, wherein the sdAb comprises a CDR1, a CDR2, and a CDR3 comprising the amino acid sequences of SEQ ID NO: 70-72, respectively.

* * * * *

SEQUENCE LISTING

<160> NUMBER OF SEQ ID NOS: 98

<210> SEQ ID NO 1
<211> LENGTH: 125
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Glu Ser Gly Gly Gly Ser Ile Gln Ala Gly Gly
1               5                   10                  15

Ser Leu Arg Leu Ser Cys Ala Ala Ser Arg Tyr Leu Tyr Ser Ile Asp
            20                  25                  30

Tyr Met Ala Trp Phe Arg Gln Ser Pro Gly Lys Glu Arg Glu Pro Val
        35                  40                  45

Ala Val Ile Tyr Thr Ala Ser Gly Ala Thr Phe Tyr Pro Asp Ser Val
    50                  55                  60

Lys Gly Arg Phe Thr Ile Ser Gln Asp Asn Ala Lys Met Thr Val Tyr
65                  70                  75                  80

Leu Gln Met Asn Ser Leu Lys Ser Glu Asp Thr Ala Met Tyr Tyr Cys
                85                  90                  95

Ala Ala Val Arg Lys Thr Asp Ser Tyr Leu Phe Asp Ala Gln Ser Phe
            100                 105                 110

Thr Tyr Trp Gly Gln Gly Thr Gln Val Thr Val Ser Ser
        115                 120                 125

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Leu Tyr Ser Ile Asp Tyr Met Ala
1               5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Ile Tyr Thr Ala Ser Gly Ala Thr Phe Tyr Pro Asp Ser Val Lys
1               5                   10                  15

Gly

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Arg Lys Thr Asp Ser Tyr Leu Phe Asp Ala Gln Ser Phe Thr Tyr
1               5                   10                  15

<210> SEQ ID NO 5
<211> LENGTH: 125
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Glu Ser Gly Gly Gly Ser Val Gln Ala Gly Gly
1               5                   10                  15
Ser Leu Arg Leu Ser Cys Val Ala Ser Arg Tyr Leu Tyr Ser Thr Asn
            20                  25                  30
Tyr Met Ala Trp Phe Arg Gln Ser Pro Gly Lys Glu Arg Glu Ala Val
        35                  40                  45
Ala Val Ile Tyr Thr Ala Ser Gly Ala Thr Leu Tyr Thr Asp Ser Val
    50                  55                  60
Lys Gly Arg Phe Thr Ile Ser Gln Asp Asn Ala Lys Met Thr Val Tyr
65                  70                  75                  80
Leu Gln Met Asn Arg Leu Lys Ser Glu Asp Thr Ala Met Tyr Tyr Cys
                85                  90                  95
Ala Ala Val Arg Lys Thr Asp Ser Tyr Leu Phe Asp Ala Gln Ser Phe
            100                 105                 110
Thr Tyr Trp Gly Gln Gly Thr Gln Val Thr Val Ser Ser
        115                 120                 125

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Leu Tyr Ser Thr Asn Tyr Met Ala
1               5

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Ile Tyr Thr Ala Ser Gly Ala Thr Leu Tyr Thr Asp Ser Val Lys
1               5                   10                  15
Gly

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Arg Lys Thr Asp Ser Tyr Leu Phe Asp Ala Gln Ser Phe Thr Tyr
1               5                   10                  15

<210> SEQ ID NO 9
<211> LENGTH: 125
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Glu Ser Gly Gly Gly Ser Ile Gln Ala Gly Gly
1               5                   10                  15

Ser Leu Arg Leu Ser Cys Val Ala Ser Arg Tyr Leu Tyr Ser Thr Asn
            20                  25                  30

Tyr Met Ala Trp Phe Arg Gln Ser Pro Gly Lys Glu Arg Glu Ala Val
        35                  40                  45

Ala Val Ile Tyr Thr Ala Ser Gly Ala Thr Leu Tyr Thr Asp Ser Val
    50                  55                  60

Lys Gly Arg Phe Thr Ile Ser Gln Asp Asn Ala Lys Met Thr Val Tyr
65                  70                  75                  80

Leu Gln Met Asn Arg Leu Lys Ser Glu Asp Thr Ala Met Tyr Tyr Cys
                85                  90                  95

Ala Ala Val Arg Lys Thr Asp Ser Tyr Leu Phe Asp Ala Gln Ser Phe
            100                 105                 110

Thr Tyr Trp Gly Gln Gly Thr Gln Val Thr Val Ser Ser
        115                 120                 125

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Leu Tyr Ser Thr Asn Tyr Met Ala
1               5

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Ile Tyr Thr Ala Ser Gly Ala Thr Leu Tyr Thr Asp Ser Val Lys
1               5                   10                  15

Gly

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Arg Lys Thr Asp Ser Tyr Leu Phe Asp Ala Gln Ser Phe Thr Tyr
1               5                   10                  15

<210> SEQ ID NO 13
<211> LENGTH: 125
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Gln Glu Ser Gly Gly Gly Ser Ile Gln Ala Gly Gly
1               5                   10                  15

Ser Leu Arg Leu Ser Cys Ala Ala Ser Arg Tyr Leu Tyr Ser Ile Asp
            20                  25                  30

Tyr Met Ala Trp Phe Arg Gln Ser Pro Gly Lys Glu Arg Glu Pro Ala
        35                  40                  45

Ala Val Ile Tyr Thr Ala Ser Gly Ala Thr Phe Tyr Pro Asp Ser Val
    50                  55                  60

Lys Gly Arg Phe Thr Ile Ser Gln Asp Asn Ala Lys Met Thr Val Tyr
65                  70                  75                  80

Leu Gln Met Asn Ser Leu Lys Ser Glu Asp Thr Ala Met Tyr Tyr Cys
                85                  90                  95

Ala Ala Val Arg Lys Thr Asp Ser Tyr Leu Phe Asp Ala Gln Ser Phe
            100                 105                 110

Thr Tyr Trp Gly Gln Gly Thr Gln Val Thr Val Ser Ser
        115                 120                 125

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Leu Tyr Ser Ile Asp Tyr Met Ala
1               5

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Ile Tyr Thr Ala Ser Gly Ala Thr Phe Tyr Pro Asp Ser Val Lys
1               5                   10                  15

Gly

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Arg Lys Thr Asp Ser Tyr Leu Phe Asp Ala Gln Ser Phe Thr Tyr
1               5                   10                  15

<210> SEQ ID NO 17
<211> LENGTH: 125
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Glu Ser Gly Gly Gly Ser Ile Gln Ala Gly Gly
1               5                   10                  15

Ser Leu Arg Leu Ser Cys Val Ala Ser Lys Tyr Leu Tyr Ser Thr Asn
            20                  25                  30

Tyr Met Ala Trp Phe Arg Gln Ser Pro Gly Lys Glu Arg Glu Ala Val
        35                  40                  45

Ala Ala Ile Tyr Thr Ala Ser Gly Ala Thr Leu Tyr Ser Asp Ser Asn
    50                  55                  60

Lys Gly Arg Phe Thr Ile Ser Gln Asp Asn Ala Lys Met Thr Val Tyr
65                  70                  75                  80

Leu Gln Met Asn Ser Leu Lys Ser Glu Asp Thr Ala Met Tyr Tyr Cys
                85                  90                  95

Ala Ala Val Arg Lys Thr Gly Ser Tyr Leu Phe Asp Ala Gln Ser Phe
            100                 105                 110

Thr Tyr Trp Gly Gln Gly Thr Gln Val Thr Val Ser Ser
        115                 120                 125

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Leu Tyr Ser Thr Asn Tyr Met Ala
1               5

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Ile Tyr Thr Ala Ser Gly Ala Thr Leu Tyr Ser Asp Ser Asn Lys
1               5                   10                  15

Gly

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Arg Lys Thr Gly Ser Tyr Leu Phe Asp Ala Gln Ser Phe Thr Tyr
1               5                   10                  15

<210> SEQ ID NO 21
<211> LENGTH: 129
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Gln Glu Ser Gly Gly Gly Ser Val Gln Ala Gly Gly
1               5                   10                  15

Ser Leu Arg Leu Ser Cys Ala Ala Ser Arg Phe Thr Tyr Ser Ser Tyr
            20                  25                  30

Cys Met Gly Trp Phe Arg Gln Ala Pro Gly Lys Glu Arg Glu Gly Val
            35                  40                  45

Ala Ser Ile Asp Ser Asp Gly Ser Thr Ser Tyr Thr Asp Ser Val Lys
        50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Leu Asp Leu Met Ser Thr Val Val Pro Gly Phe Cys Gly Phe Leu Leu
            100                 105                 110

Ser Ala Gly Met Asp Tyr Trp Gly Lys Gly Thr Gln Val Thr Val Ser
        115                 120                 125

Ser

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Phe Thr Tyr Ser Ser Tyr Cys Met Gly
1               5

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Ile Asp Ser Asp Gly Ser Thr Ser Tyr Thr Asp Ser Val Lys Gly
1               5                   10                  15

<210> SEQ ID NO 24
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Leu Met Ser Thr Val Val Pro Gly Phe Cys Gly Phe Leu Leu Ser
1               5                   10                  15

Ala Gly Met Asp Tyr
            20
```

```
<210> SEQ ID NO 25
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Thr Phe Asn Ser Asn
            20                  25                  30

Cys Met Gly Trp Phe Arg Gln Ala Pro Gly Lys Glu Arg Glu Gly Val
        35                  40                  45

Ala Thr Ile Tyr Thr Gly Val Gly Ser Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Glu Pro Leu Ser Arg Val Tyr Gly Gly Ser Cys Pro Thr Pro
            100                 105                 110

Thr Phe Gly Tyr Trp Gly Gln Gly Thr Gln Val Thr Val Ser Ser
        115                 120                 125

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Tyr Thr Phe Asn Ser Asn Cys Met Gly
1               5

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Ile Tyr Thr Gly Val Gly Ser Thr Tyr Tyr Ala Asp Ser Val Lys
1               5                   10                  15

Gly

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Pro Leu Ser Arg Val Tyr Gly Gly Ser Cys Pro Thr Pro Thr Phe
1               5                   10                  15

Gly Tyr
```

```
<210> SEQ ID NO 29
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Met Tyr
                20                  25                  30

Cys Met Gly Trp Phe Arg Gln Ala Pro Gly Lys Glu Arg Glu Gly Val
            35                  40                  45

Ala Gln Ile Asn Ser Asp Gly Ser Thr Ser Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Asp Ser Arg Val Tyr Gly Gly Ser Trp Tyr Glu Arg Leu Cys Gly
            100                 105                 110

Pro Tyr Thr Tyr Glu Tyr Asn Tyr Trp Gly Gln Gly Thr Gln Val Thr
        115                 120                 125

Val Ser Ser
    130

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Thr Tyr Ser Met Tyr Cys Met Gly
1               5

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Ile Asn Ser Asp Gly Ser Thr Ser Tyr Ala Asp Ser Val Lys Gly
1               5                   10                  15

<210> SEQ ID NO 32
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Ser Arg Val Tyr Gly Gly Ser Trp Tyr Glu Arg Leu Cys Gly Pro
```

```
1               5                   10                  15
Tyr Thr Tyr Glu Tyr Asn Tyr
            20

<210> SEQ ID NO 33
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Ala Tyr Ser Thr Tyr
            20                  25                  30

Cys Met Gly Trp Phe Arg Gln Ala Pro Gly Lys Glu Arg Glu Gly Val
        35                  40                  45

Ala Ala Ile Asp Ser Gly Gly Ser Thr Ser Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Arg Met Asn Ser Leu Lys Pro Glu Asp Thr Ala Met Tyr Tyr Cys Ala
                85                  90                  95

Ala Val Pro Pro Pro Asp Gly Gly Ser Cys Leu Phe Leu Gly Pro
            100                 105                 110

Glu Ile Lys Val Ser Lys Ala Asp Phe Arg Tyr Trp Gly Gln Gly Thr
        115                 120                 125

Gln Val Thr Val Ser Ser
        130

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Ala Tyr Ser Thr Tyr Cys Met Gly
1               5

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Ile Asp Ser Gly Gly Ser Thr Ser Tyr Ala Asp Ser Val Lys Gly
1               5                   10                  15

<210> SEQ ID NO 36
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 36

Val Pro Pro Pro Asp Gly Gly Ser Cys Leu Phe Leu Gly Pro Glu
1               5                   10                  15

Ile Lys Val Ser Lys Ala Asp Phe Arg Tyr
            20                  25

<210> SEQ ID NO 37
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Gln Glu Ser Gly Gly Gly Ser Val Gln Ala Gly Gly
1               5                   10                  15

Ser Leu Arg Leu Ser Cys Ala Ala Ser Arg Tyr Leu Tyr Ser Ile Asp
            20                  25                  30

Tyr Met Ala Trp Phe Arg Gln Ser Pro Gly Lys Glu Arg Glu Pro Val
        35                  40                  45

Ala Val Ile Tyr Thr Ala Ser Gly Ala Thr Phe Tyr Pro Asp Ser Val
    50                  55                  60

Lys Gly Arg Phe Thr Ile Ser Gln Asp Asn Ala Lys Met Thr Val Tyr
65                  70                  75                  80

Leu Gln Met Asn Ser Leu Lys Ser Glu Asp Thr Ala Met Tyr Tyr Cys
                85                  90                  95

Ala Ala Val Arg Lys Thr Asp Ser Tyr Leu Phe Asp Ala Gln Ser Phe
            100                 105                 110

Thr Tyr Trp Gly Gln Gly Thr Gln Val Thr Val Ser Ser
        115                 120                 125

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Tyr Leu Tyr Ser Ile Asp Tyr Met Ala
1               5

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Ile Tyr Thr Ala Ser Gly Ala Thr Phe Tyr Pro Asp Ser Val Lys
1               5                   10                  15

Gly

<210> SEQ ID NO 40
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 40

Val Arg Lys Thr Asp Ser Tyr Leu Phe Asp Ala Gln Ser Phe Thr Tyr
1               5                   10                  15

<210> SEQ ID NO 41
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Gln Glu Ser Gly Gly Gly Ser Val Gln Ala Gly Gly
1               5                   10                  15

Ser Leu Arg Leu Ser Cys Gly Ala Ser Arg Tyr Thr Tyr Ser Ser Tyr
            20                  25                  30

Cys Met Gly Trp Phe Arg Gln Ala Pro Gly Lys Glu Arg Glu Gly Val
        35                  40                  45

Ala Val Ile Asp Ser Asp Gly Ser Thr Ser Tyr Ala Asp Ser Val Lys
    50                  55                  60

Gly Arg Phe Thr Ile Ser Lys Asp Asn Gly Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Asp Leu Gly His Tyr Arg Pro Pro Cys Gly Val Leu Tyr Leu Gly
            100                 105                 110

Met Asp Tyr Trp Gly Lys Gly Thr Gln Val Thr Val Ser Ser
        115                 120                 125

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Thr Tyr Ser Ser Tyr Cys Met Gly
1               5

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Val Ile Asp Ser Asp Gly Ser Thr Ser Tyr Ala Asp Ser Val Lys Gly
1               5                   10                  15

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
```

```
                    peptide

<400> SEQUENCE: 44

Asp Leu Gly His Tyr Arg Pro Pro Cys Gly Val Leu Tyr Leu Gly Met
1               5                   10                  15

Asp Tyr

<210> SEQ ID NO 45
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Gln Glu Ser Gly Gly Gly Ser Val Gln Ala Gly Gly
1               5                   10                  15

Ser Leu Arg Leu Ser Cys Thr Val Ser Gly Tyr Thr Tyr Ser Ser Asn
            20                  25                  30

Cys Met Gly Trp Phe Arg Gln Ala Pro Gly Lys Glu Arg Glu Gly Val
        35                  40                  45

Ala Thr Ile Tyr Thr Gly Gly Asn Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Asn Leu Lys Pro Glu Asp Thr Ala Met Tyr Tyr Cys
                85                  90                  95

Ala Ala Glu Pro Leu Ser Arg Val Tyr Gly Gly Ser Cys Pro Thr Pro
            100                 105                 110

Thr Phe Asp Tyr Trp Gly Gln Gly Thr Gln Val Thr Val Ser Ser
        115                 120                 125

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Tyr Thr Tyr Ser Ser Asn Cys Met Gly
1               5

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Thr Ile Tyr Thr Gly Gly Gly Asn Thr Tyr Tyr Ala Asp Ser Val Lys
1               5                   10                  15

Gly

<210> SEQ ID NO 48
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 48

Glu Pro Leu Ser Arg Val Tyr Gly Gly Ser Cys Pro Thr Pro Thr Phe
1               5                   10                  15

Asp Tyr

<210> SEQ ID NO 49
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Ser Tyr Ser Ser Asn
            20                  25                  30

Cys Met Gly Trp Phe Arg Gln Ala Pro Gly Lys Glu Arg Glu Gly Val
        35                  40                  45

Ala Thr Ile His Thr Gly Gly Ser Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Glu Pro Leu Ser Arg Leu Tyr Gly Gly Ser Cys Pro Thr Pro
            100                 105                 110

Thr Phe Gly Tyr Trp Gly Gln Gly Thr Gln Val Thr Val Ser Ser
        115                 120                 125

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Tyr Ser Tyr Ser Ser Asn Cys Met Gly
1               5

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Ile His Thr Gly Gly Ser Thr Tyr Tyr Ala Asp Ser Val Lys
1               5                   10                  15

Gly

<210> SEQ ID NO 52
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Glu Pro Leu Ser Arg Leu Tyr Gly Gly Ser Cys Pro Thr Pro Thr Phe
1               5                   10                  15

Gly Tyr

<210> SEQ ID NO 53
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Gln Glu Ser Gly Gly Gly Ser Val Gln Ala Gly Gly
1               5                   10                  15

Ser Leu Arg Leu Ser Cys Gly Ala Ser Gly Tyr Thr Tyr Ser Ser Tyr
            20                  25                  30

Cys Met Gly Trp Phe Arg Gln Val Pro Gly Lys Glu Arg Glu Gly Val
        35                  40                  45

Ala Val Ile Asp Ser Asp Gly Ser Thr Ser Tyr Ala Asp Ser Val Lys
    50                  55                  60

Gly Arg Phe Thr Ile Ser Lys Asp Asn Gly Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Asp Leu Gly His Tyr Arg Pro Pro Cys Gly Val Leu Tyr Leu Gly
            100                 105                 110

Met Asp Tyr Trp Gly Lys Gly Thr Gln Val Thr Val Ser Ser
        115                 120                 125

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Tyr Thr Tyr Ser Ser Tyr Cys Met Gly
1               5

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Val Ile Asp Ser Asp Gly Ser Thr Ser Tyr Ala Asp Ser Val Lys Gly
1               5                   10                  15

<210> SEQ ID NO 56
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Leu Gly His Tyr Arg Pro Pro Cys Gly Val Leu Tyr Leu Gly Met
1               5                   10                  15

Asp Tyr

<210> SEQ ID NO 57
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Gln Glu Ser Gly Gly Gly Ser Val Gln Ala Gly Gly
1               5                   10                  15

Ser Leu Arg Leu Ser Cys Gly Ala Ser Gly Tyr Thr Tyr Ser Gly Tyr
            20                  25                  30

Cys Met Gly Trp Phe Arg Gln Ala Pro Gly Lys Glu Arg Glu Gly Val
        35                  40                  45

Ala Val Ile Asp Ser Asp Gly Ser Thr Ser Tyr Ala Asp Ser Val Lys
    50                  55                  60

Gly Arg Phe Thr Ile Ser Lys Asp Asn Gly Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Asp Leu Gly His Tyr Arg Pro Pro Cys Gly Val Leu Tyr Leu Gly
            100                 105                 110

Met Asp Tyr Trp Gly Lys Gly Thr Gln Val Thr Val Ser Ser
        115                 120                 125

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Tyr Thr Tyr Ser Gly Tyr Cys Met Gly
1               5

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Val Ile Asp Ser Asp Gly Ser Thr Ser Tyr Ala Asp Ser Val Lys Gly
1               5                   10                  15

<210> SEQ ID NO 60
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Leu Gly His Tyr Arg Pro Pro Cys Gly Val Leu Tyr Leu Gly Met
1               5                   10                  15

Asp Tyr

<210> SEQ ID NO 61
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Gln Glu Ser Gly Gly Gly Ser Val Gln Ala Gly Gly
1               5                   10                  15

Ser Leu Arg Leu Ala Cys Ala Ala Ser Arg Tyr Thr Tyr Ser Asn Tyr
            20                  25                  30

Cys Met Gly Trp Phe Arg Gln Ala Pro Gly Lys Glu Arg Glu Gly Val
        35                  40                  45

Ala Thr Ile Asp Ser Asp Gly Asn Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Gly Asp Thr Ala Met Tyr Tyr Cys Ala
                85                  90                  95

Ala Asp Leu Gly His Tyr Arg Pro Pro Cys Gly Ala Tyr Tyr Tyr Gly
            100                 105                 110

Met Asp Tyr Trp Gly Lys Gly Thr Gln Val Thr Val Ser Ser
        115                 120                 125

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Tyr Thr Tyr Ser Asn Tyr Cys Met Gly
1               5

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Ile Asp Ser Asp Gly Asn Thr Ser Tyr Ala Asp Ser Val Lys Gly
1               5                   10                  15

<210> SEQ ID NO 64
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Leu Gly His Tyr Arg Pro Pro Cys Gly Ala Tyr Tyr Gly Met
1               5                   10                  15

Asp Tyr

<210> SEQ ID NO 65
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Ser Asn Cys Ser Tyr
                20                  25                  30

Asp Met Thr Trp Tyr Arg Gln Ala Pro Gly Lys Glu Arg Glu Phe Val
            35                  40                  45

Ser Ala Ile His Ser Asp Gly Ser Thr Arg Tyr Ala Asp Ser Val Lys
        50                  55                  60

Gly Arg Phe Phe Ile Ser Gln Asp Asn Ala Lys Asn Thr Val Tyr Leu
65                  70                  75                  80

Gln Met Asn Ser Leu Lys Pro Glu Asp Thr Ala Met Tyr Tyr Cys Lys
                85                  90                  95

Thr Asp Pro Leu His Cys Arg Ala His Gly Gly Ser Trp Tyr Ser Val
            100                 105                 110

Arg Ala Asn Tyr Trp Gly Gln Gly Thr Gln Val Thr Val Ser Ser
        115                 120                 125

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Tyr Ser Asn Cys Ser Tyr Asp Met Thr
1               5

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Ile His Ser Asp Gly Ser Thr Arg Tyr Ala Asp Ser Val Lys Gly
1               5                   10                  15

<210> SEQ ID NO 68
<211> LENGTH: 19
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Pro Leu His Cys Arg Ala His Gly Gly Ser Trp Tyr Ser Val Arg
1               5                   10                  15
Ala Asn Tyr

<210> SEQ ID NO 69
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Thr Tyr Asn Ser Asn
            20                  25                  30

Cys Met Gly Trp Phe Arg Gln Ala Pro Gly Lys Glu Arg Glu Gly Val
        35                  40                  45

Ala Thr Ile Tyr Thr Gly Val Gly Ser Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Glu Pro Leu Ser Arg Val Tyr Gly Gly Ser Cys Pro Thr Pro
            100                 105                 110

Thr Phe Gly Tyr Trp Gly Gln Gly Thr Gln Val Thr Val Ser Ser
        115                 120                 125

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Tyr Thr Tyr Asn Ser Asn Cys Met Gly
1               5

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Ile Tyr Thr Gly Val Gly Ser Thr Tyr Tyr Ala Asp Ser Val Lys
1               5                   10                  15
Gly
```

```
<210> SEQ ID NO 72
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Glu Pro Leu Ser Arg Val Tyr Gly Gly Ser Cys Pro Thr Pro Thr Phe
1               5                   10                  15

Gly Tyr

<210> SEQ ID NO 73
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
caggttcagc ttcaggagtc cggtggaggc tccatccagg ccgggggctc tctccgcctg      60
tcttgcgccg cttccagata cctctacagt atcgactaca tggcttggtt tcgtcagagc     120
ccaggaaaag agcgggaacc cgtggcagta atctacactg cctcaggtgc acattttac     180 cccgactctg tcaagggcag gttcaccatc tctcaggata atgccaagat gacagtgtac     240
ttgcagatga actccctgaa atctgaggat accgctatgt attactgtgc cgcagtgcgc     300
aagaccgatt cttacctgtt cgacgctcag agttttacct actggggcca gggcactcag     360
gtcaccgtca gcagc                                                      375

<210> SEQ ID NO 74
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
caggtgcagt tgcaggagtc cggcgggggt tccgtgcaag caggcggatc tctgcgcctg      60
tcctgcgtgg cctctcgtta tttgtatagc accaactaca tggcttggtt ccgtcagtcc     120
ccaggcaaag agcgcgaagc cgtagccgta atctatacgg cctctgggc aacactctat      180 accgactcag tgaagggacg cttcacgatt tcccaagaca atgcaaagat gaccgtgtac     240
ttgcagatga accgcctgaa gagcgaggac acggctatgt attactgcgc agccgtgcgc     300
aagaccgact cctacttgtt tgacgctcag tccttcactt attggggcca gggtacacag     360
gtcaccgtga gcagt                                                      375

<210> SEQ ID NO 75
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
caagtacagc tccaggagag cggcggtgga tctatccaag caggggtag ccttaggttg       60 tcctgtgtgg cgtccagata cctgtatagc acgaactaca tggcatggtt cagacagtcc     120
```

```
ccaggcaagg aacgcgaggc agtcgccgtt atttacactg catctggggc caccctctat    180
acggacagcg tgaagggaag gtttacaatc tcccaggaca acgcgaagat gaccgtgtac    240
cttcagatga accgcctgaa gtccgaggac accgccatgt attactgtgc agcggtgcgc    300
aagaccgaca gctatctgtt cgacgcgcag tcattcactt attggggcca aggaacccaa    360
gtgaccgtca gctca                                                     375
```

```
<210> SEQ ID NO 76
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
```

```
caggtgcagc tccaagagtc cggggaggc tctatccagg cggaggcag tctgcgcttg     60 tcctgcgccg caagtcgtta tctgtactcc attgattaca tggcatggtt ccgccagtcc    120
ccaggtaagg aacgtgaacc tgccgctgtg atctacaccg cttctggagc aaccttttat    180
cctgatagcg ttaagggtcg cttcaccatc tctcaggata acgccaaaat gacagtgtac    240
ctccagatga acagcctgaa gtctgaggac actgccatgt actattgtgc ggctgtgcgc    300
aagaccgact cctatctgtt tgatgcacag agctttacct attggggtca gggcacccag    360
gtgactgtgt ctagc                                                     375
```

```
<210> SEQ ID NO 77
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
```

```
caggtccagt tgcaggagtc cggtggaggt tccatccagg cgggtgggtc ccttcgtctc     60
tcctgcgtgg cctctaagta cctgtattca accaactaca tggcatggtt cagacagtct    120
cccggcaaag agcgtgaggc agtggccgcg atctatacag cttctggggc caccctgtac    180
tctgattcca ataaggggaag gttcactatc tcacaggata acgccaaaat gaccgtctac    240
cttcagatga acagcctcaa gtctgaagac acggcaatgt attactgtgc agccgtgcgc    300
aaaactggga gctacctgtt tgacgctcag tctttcactt attggggcca gggtacgcag    360
gtgacagtct cttct                                                     375
```

```
<210> SEQ ID NO 78
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
```

```
caggtgcaac tccaggagag cggaggcggt tctgttcagg caggaggttc cctgagactg     60
tcctgtgccg cgtctcgctt tacgtattca tcctactgca tgggatggtt cagacaagcg    120
ccggggaaag aagggaagg cgtggcctcc attgactccg acggctcaac ttcatacact    180
gatagcgtga aaggccggtt caccatctct aaggacaacg cgaagaacac cctgtatctc    240
```

| cagatgaaca gcctcaagcc tgaggatact gccatgtact attgcgcact cgacctgatg | 300 |
|---|---|
| tctactgtgg tcccaggctt ctgcgggttc ctgctctctg ctggcatgga ctactggggg | 360 |
| aagggcactc aggtaacggt tagctcc | 387 |

<210> SEQ ID NO 79
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

| caggtgcagc ttcaggaatc tggcggggc tccgtgcagg ccggggctc cctcagactt | 60 |
|---|---|
| tcctgtgccg tctccggtta cacatttaac agtaactgta tgggctggtt ccgccaggca | 120 |
| ccaggcaagg agagggaagg tgtggccaca atctatactg gtgttgggag tacgtactat | 180 |
| gctgattccg tgaaaggtcg cttcacaatt tcccaggaca acgcgaagaa cactgtgtac | 240 |
| ttgcagatga atagcctgaa gcctgaagat accgcaatgt attactgcgc tgccgagcca | 300 |
| ctctcccgcg tatatggtgg aagttgcccc accccacttt cggttactg gggccagggc | 360 |
| actcaagtga ccgtgtcctc t | 381 |

<210> SEQ ID NO 80
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

| caggttcagc ttcaggagtc tgggggcggt tcagtgcagg ctggcggttc tctccgcctg | 60 |
|---|---|
| tcctgcgctg ccagcggcta tacttacagc atgtactgca tgggctggtt ccggcaagcc | 120 |
| cccggcaaag agcgtgaggg cgtcgctcaa atcaacagcg acgggtcaac cagctacgcc | 180 |
| gattctgtca agggcagatt tactatcagc aaggacaacg ccaaaaacac actgtacctc | 240 |
| cagatgaact ctttgaagcc tgaggacacc gcgatgtatt actgcgccgc tgacagccgc | 300 |
| gtgtacggtg gcagctggta tgagaggctg tgcggcccgt acacctacga gtacaactat | 360 |
| tggggacagg gcacgcaggt gacagttagc tcc | 393 |

<210> SEQ ID NO 81
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

| caggtgcaac tgcaagagag tggcggaggc tccgtccagg ctggaggttc cctgcggctg | 60 |
|---|---|
| tcttgcgccg tcagcggcta cgcatattcc acttactgta tgggttggtt ccgccaggcc | 120 |
| cctggaaagg aacgcgaggg tgttgccgct attgatagcg gaggctccac atcctatgcg | 180 |
| gactccgtga aggtcgtttt caccatctcc aaggataacg ccaagaacac tctgtacctg | 240 |
| cgcatgaact ctctgaagcc tgaggacact gccatgtatt actgcgccgc tgtgccccct | 300 |
| ccacccgacg ggggctcttg tctgtttctt ggcccggaga tcaaggtgtc caaggctgat | 360 | ttccgttatt ggggccaggg aactcaagtc accgtgtctt cc    402

<210> SEQ ID NO 82
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
caggtccagc tccaggagtc cggtggaggc tccgttcagg ccggtggcag cttgcgtctg    60
agctgcgcgg cttcaagata cctgtactcc attgattaca tggcatggtt ccgtcagtct   120
cctggcaagg agcgcgagcc cgtcgctgtg atctataccg ccagcggagc cacgttctac   180
cctgattccg tcaagggccg cttcaccatt agccaagaca acgctaagat gacggtgtac   240
ctccaaatga atagcctgaa aagcgaggac acagcgatgt attactgcgc cgctgttagg   300
aaaactgata gttacctgtt cgatgcacag tctttcactt actgggggca gggcacccaa   360
gttaccgtct cctct                                                    375

<210> SEQ ID NO 83
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
caggtgcagc tccaggaatc tggaggggc agtgtgcagg ccggggggctc cctgcgcttg    60
agctgtggag ccagccgcta cacgtattcc agttactgta tgggctggtt cagacaagct   120
ccgggtaagg agagagaggg agttgccgta attgattctg acgggtccac tagctatgcg   180
gattcagtca agggccggtt caccatcagc aaggacaatg gtaagaacac actgtacctg   240
caaatgaaca gcctgaagcc cgaggacacc gccatgtact attgtgccgc tgatctcgga   300
cattaccgcc ctccctgcgg tgtgctctat ctcgggatgg actattgggg taagggcacc   360
caggtgaccg tgtcctct                                                 378

<210> SEQ ID NO 84
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
caggtgcagc tccaggaaag cggcgggggt agcgttcaag caggtgggtc cctgcgcttg    60
agctgtactg tgtccggcta cacctactca agcaactgca tgggatggtt ccgtcaggcc   120
cctggcaagg aacgcgaagg cgtggctact atctacaccg gcggtggcaa cacttattac   180
gccgactccg ttaaggggcg tttcactatc agccaagaca cgccaagaa caccgtgtat   240
ctgcaaatga ataacctgaa gcctgaagac accgccatgt attactgtgc tgccgagccc   300
cttttcccgcg tttacggcgg ttcttgtcct accccctacct ttgactactg ggtcaggga   360
acacaggtga cagtgtccag t                                             381

<210> SEQ ID NO 85
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

| caagtccaac tccaggaatc tgggggaggc tccgtacagg ctggcggttc ccttcgtctg | 60 |
| tcctgtgctg tgtcagggta ctcctactcc agtaactgta tgggctggtt ccggcaagcc | 120 |
| cccggaaagg agcgcgaggg cgtggctacc atccacacag ggggcggttc cacatattac | 180 |
| gccgatagtg tcaagggccg cttcaccatt agtcaggaca acgccaagaa taccgtttac | 240 |
| cttcaaatga actctttgaa acctgaggac actgcgatgt attactgtgc ggcagagcct | 300 |
| ttgtcccgcc tgtacggggg atcttgtccg accccgactt tcgggtactg gggacagggc | 360 |
| acccaggtga cagtgtcctc c | 381 |

<210> SEQ ID NO 86
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86

| caggtgcagt tgcaggaaag cggggtggc agcgtccaag ccggtggcag cctgcgtctg | 60 |
| tcctgcggtg cctccggcta tacttactcc agctattgca tgggttggtt ccgccaagtg | 120 |
| ccaggaaagg agcgtgaggg ggtggctgta attgattcag atgggtcaac aagctacgct | 180 |
| gacagcgtta aggtcgctt caccatcagt aaggacaacg gcaagaacac cctctacctg | 240 |
| caaatgaact ccctgaagcc ggaggatacc gcaatgtatt actgtgccgc tgacttggga | 300 |
| cactaccgcc ctccgtgcgg tgtgctttat ctgggcatgg attactgggg taagggaacc | 360 |
| caagtgacgg tgtcttct | 378 |

<210> SEQ ID NO 87
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87

| caggtacaac tccaggagtc tggcggtggg tccgtgcagg caggtggcag ccttcgcctc | 60 |
| tcctgcgggg cctccgggta cacctatagt ggctactgca tgggtggtt caggcaagcc | 120 |
| cccggtaagg aacgtgaggg agttgctgtg attgattcag atgggtccac gagttacgct | 180 |
| gactccgtga aggtaggtt cacaatctcc aaagataatg gcaagaacac cctctacctt | 240 |
| cagatgaata gcctgaagcc agaagacacc gccatgtatt actgtgctgc cgacctggga | 300 |
| cactatcgcc ctccgtgcgg ggtcctgtac ttgggcatgg actattgggg caaggggacc | 360 |
| caggtgactg tgtcctct | 378 |

<210> SEQ ID NO 88
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

| caggtgcagt tgcaggaatc cggtggaggc tctgttcagg ccgggggctc tctccgcctg | 60 |
| gcctgcgcag cctccaggta tacttacagc aactactgca tggggtggtt tcgccaggct | 120 |
| ccgggcaaag agcgtgaggg agtggctact attgattccg atggaaacac cagctacgcc | 180 |
| gatagcgtga aggcagatt tactatcagc agagataacg ctaaaaacac gttgtacctc | 240 |
| cagatgaact cactcaagcc gggggacaca gctatgtatt actgcgcagc cgatctgggt | 300 |
| cactaccgcc cgccctgcgg cgcatattac tatggcatgg actactgggg caagggcacc | 360 |
| caggtgaccg tgtccagt | 378 |

<210> SEQ ID NO 89
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89

| caggtgcagc tccaagagtc tggcgggggt tccgtgcaag ccggtggctc actcaggttg | 60 |
| agttgcgcag ccagcggcta tagcaactgt tcctatgaca tgacttggta tcgccaggcc | 120 |
| cctggcaaag agcgtgagtt cgtgtcagct attcactccg acggctccac tcgttatgcg | 180 |
| gactctgtga agggccggtt tttcatctcc caggacaacg ctaaaaacac tgtctatttg | 240 |
| cagatgaact ctctgaaacc cgaagatacc gccatgtact attgcaaaac cgatcctctg | 300 |
| cattgtcgcg cccacggcgg gagttggtac tctgtgcggg ccaactattg gggccagggc | 360 |
| acccaggtca ccgtgtcctc a | 381 |

<210> SEQ ID NO 90
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

| caggtacaac tccaggagtc tggcggtggc agcgtgcagg caggcggaag cctgaggctg | 60 |
| tcctgcgctg tatctggcta cacttataat tccaactgca tgggttggtt tcggcaggct | 120 |
| ccaggtaagg agcgcgaggg cgtcgccacc atttatacag gtgttggcag cacatattac | 180 |
| gccgacagcg tgaagggaag gttcaccatc tcccaagaca atgcgaaaaa cacagtgtat | 240 |
| ctccagatga atagcctgaa gcccgaggac acggctatgt attactgcgc tgccgagcca | 300 |
| ctgagcagag tgtatgggg cagctgtcct acacccactt tcggctattg gggtcaaggc | 360 |
| acccaggtta cagtcagctc c | 381 |

<210> SEQ ID NO 91
<211> LENGTH: 578
<212> TYPE: PRT
<213> ORGANISM: Homo sapiens

<400> SEQUENCE: 91

Met Leu Pro Cys Leu Val Val Leu Leu Ala Ala Leu Leu Ser Leu Arg

-continued

```
1               5                   10                  15
Leu Gly Ser Asp Ala His Gly Thr Glu Leu Pro Ser Pro Ser Val
                20                  25                  30

Trp Phe Glu Ala Glu Phe Phe His Ile Leu His Trp Thr Pro Ile
                35                  40                  45

Pro Asn Gln Ser Glu Ser Thr Cys Tyr Glu Val Ala Leu Leu Arg Tyr
50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
                100                 105                 110

Val Thr Asn Thr Arg Phe Ser Val Asp Glu Val Thr Leu Thr Val Gly
                115                 120                 125

Ser Val Asn Leu Glu Ile His Asn Gly Phe Ile Leu Gly Lys Ile Gln
130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
                180                 185                 190

Leu Thr Ser Gly Glu Val Gly Glu Phe Cys Val Gln Val Lys Pro Ser
                195                 200                 205

Val Ala Ser Arg Ser Asn Lys Gly Met Trp Ser Lys Glu Glu Cys Ile
210                 215                 220

Ser Leu Thr Arg Gln Tyr Phe Thr Val Thr Asn Val Ile Ile Phe Phe
225                 230                 235                 240

Ala Phe Val Leu Leu Leu Ser Gly Ala Leu Ala Tyr Cys Leu Ala Leu
                245                 250                 255

Gln Leu Tyr Val Arg Arg Arg Lys Lys Leu Pro Ser Val Leu Leu Phe
                260                 265                 270

Lys Lys Pro Ser Pro Phe Ile Phe Ile Ser Gln Arg Pro Ser Pro Glu
                275                 280                 285

Thr Gln Asp Thr Ile His Pro Leu Asp Glu Glu Ala Phe Leu Lys Val
                290                 295                 300

Ser Pro Glu Leu Lys Asn Leu Asp Leu His Gly Ser Thr Asp Ser Gly
305                 310                 315                 320

Phe Gly Ser Thr Lys Pro Ser Leu Gln Thr Glu Glu Pro Gln Phe Leu
                325                 330                 335

Leu Pro Asp Pro His Pro Gln Ala Asp Arg Thr Leu Gly Asn Arg Glu
                340                 345                 350

Pro Pro Val Leu Gly Asp Ser Cys Ser Ser Gly Ser Ser Asn Ser Thr
                355                 360                 365

Asp Ser Gly Ile Cys Leu Gln Glu Pro Ser Leu Ser Pro Ser Thr Gly
                370                 375                 380

Pro Thr Trp Glu Gln Gln Val Gly Ser Asn Ser Arg Gly Gln Asp Asp
385                 390                 395                 400

Ser Gly Ile Asp Leu Val Gln Asn Ser Glu Gly Arg Ala Gly Asp Thr
                405                 410                 415

Gln Gly Gly Ser Ala Leu Gly His His Ser Pro Pro Glu Pro Glu Val
                420                 425                 430
```

```
Pro Gly Glu Glu Asp Pro Ala Ala Val Ala Phe Gln Gly Tyr Leu Arg
        435                 440                 445

Gln Thr Arg Cys Ala Glu Lys Ala Thr Lys Thr Gly Cys Leu Glu
450                 455                 460

Glu Glu Ser Pro Leu Thr Asp Gly Leu Gly Pro Lys Phe Gly Arg Cys
465                 470                 475                 480

Leu Val Asp Glu Ala Gly Leu His Pro Ala Leu Ala Lys Gly Tyr
                485                 490                 495

Leu Lys Gln Asp Pro Leu Glu Met Thr Leu Ala Ser Ser Gly Ala Pro
                500                 505                 510

Thr Gly Gln Trp Asn Gln Pro Thr Glu Glu Trp Ser Leu Leu Ala Leu
                515                 520                 525

Ser Ser Cys Ser Asp Leu Gly Ile Ser Asp Trp Ser Phe Ala His Asp
                530                 535                 540

Leu Ala Pro Leu Gly Cys Val Ala Ala Pro Gly Gly Leu Leu Gly Ser
545                 550                 555                 560

Phe Asn Ser Asp Leu Val Thr Leu Pro Leu Ile Ser Ser Leu Gln Ser
                565                 570                 575

Ser Glu

<210> SEQ ID NO 92
<211> LENGTH: 214
<212> TYPE: PRT
<213> ORGANISM: Homo sapiens

<400> SEQUENCE: 92

His Gly Thr Glu Leu Pro Ser Pro Pro Ser Val Trp Phe Glu Ala Glu
1               5                   10                  15

Phe Phe His His Ile Leu His Trp Thr Pro Ile Pro Asn Gln Ser Glu
                20                  25                  30

Ser Thr Cys Tyr Glu Val Ala Leu Leu Arg Tyr Gly Ile Glu Ser Trp
            35                  40                  45

Asn Ser Ile Ser Asn Cys Ser Gln Thr Leu Ser Tyr Asp Leu Thr Ala
        50                  55                  60

Val Thr Leu Asp Leu Tyr His Ser Asn Gly Tyr Arg Ala Arg Val Arg
65                  70                  75                  80

Ala Val Asp Gly Ser Arg His Ser Asn Trp Thr Val Thr Asn Thr Arg
                85                  90                  95

Phe Ser Val Asp Glu Val Thr Leu Thr Val Gly Ser Val Asn Leu Glu
                100                 105                 110

Ile His Asn Gly Phe Ile Leu Gly Lys Ile Gln Leu Pro Arg Pro Lys
            115                 120                 125

Met Ala Pro Ala Asn Asp Thr Tyr Glu Ser Ile Phe Ser His Phe Arg
130                 135                 140

Glu Tyr Glu Ile Ala Ile Arg Lys Val Pro Gly Asn Phe Thr Phe Thr
145                 150                 155                 160

His Lys Lys Val Lys His Glu Asn Phe Ser Leu Leu Thr Ser Gly Glu
                165                 170                 175

Val Gly Glu Phe Cys Val Gln Val Lys Pro Ser Val Ala Ser Arg Ser
                180                 185                 190

Asn Lys Gly Met Trp Ser Lys Glu Glu Cys Ile Ser Leu Thr Arg Gln
            195                 200                 205

Tyr Phe Thr Val Thr Asn
            210
```

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 93

His His His His His His
1               5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 94

His His His His His His His His
1               5

<210> SEQ ID NO 95
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-10 "Gly Gly Gly
      Ser" repeating units

<400> SEQUENCE: 95

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 96
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(50)
<223> OTHER INFORMATION: This sequence may encompass 1-10 "Gly Gly Gly
      Ser Gly" repeating units

<400> SEQUENCE: 96

Gly Gly Gly Ser Gly Gly Gly Gly Ser Gly Gly Gly Ser Gly Gly
1               5                   10                  15

Gly Gly Ser Gly Gly Gly Gly Ser Gly Gly Gly Ser Gly Gly Gly
            20                  25                  30

Gly Ser Gly Gly Gly Gly Ser Gly Gly Gly Ser Gly Gly Gly Gly
        35                  40                  45

```
<210> SEQ ID NO 97
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-10 "Gly Gly Ser
      Gly" repeating units

<400> SEQUENCE: 97

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly
        35                  40

<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: SITE
<222> LOCATION: (1)..(6)
<223> OTHER INFORMATION: This sequence may encompass 3-6 residues

<400> SEQUENCE: 98

His His His His His His
1               5
```